(12) United States Patent
Knerr et al.

(10) Patent No.: US 11,779,648 B2
(45) Date of Patent: Oct. 10, 2023

(54) CO-AGONISTS AT GLP-1 AND GIP RECEPTORS SUITABLE FOR ORAL DELIVERY

(71) Applicant: Novo Nordisk A/S, Bagsvaerd (DK)

(72) Inventors: Patrick James Knerr, Plainfield, IN (US); Brian Finan, Indianapolis, IN (US); Richard Dimarchi, Carmel, IN (US)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 17/574,079

(22) Filed: Jan. 12, 2022

(65) Prior Publication Data

US 2022/0125940 A1 Apr. 28, 2022

Related U.S. Application Data

(63) Continuation of application No. PCT/EP2021/070485, filed on Jul. 22, 2021.

(60) Provisional application No. 63/156,988, filed on Mar. 5, 2021, provisional application No. 63/055,026, filed on Jul. 22, 2020.

(30) Foreign Application Priority Data

Aug. 24, 2020 (EP) .................... 20192414

(51) Int. Cl.
| | | |
|---|---|---|
| *A61K 47/64* | (2017.01) | |
| *A61K 47/54* | (2017.01) | |
| *A61K 38/26* | (2006.01) | |
| *C07K 14/605* | (2006.01) | |
| *A61K 38/00* | (2006.01) | |

(52) U.S. Cl.
CPC .............. *A61K 47/64* (2017.08); *A61K 38/26* (2013.01); *A61K 47/542* (2017.08); *C07K 14/605* (2013.01); *A61K 38/00* (2013.01)

(58) Field of Classification Search
CPC ....... A61K 38/26; A61K 47/542; A61K 47/64
See application file for complete search history.

(56) References Cited

U.S. PATENT DOCUMENTS

| | | | |
|---|---|---|---|
| 8,507,428 | B2 | 8/2013 | Dimarchi et al. |
| 9,745,360 | B2 | 8/2017 | Haack et al. |
| 9,758,561 | B2 * | 9/2017 | Bossart .................. A61K 38/28 |
| 9,868,772 | B2 | 1/2018 | Dimarchi et al. |
| 10,604,555 | B2 | 3/2020 | Hogendorf et al. |
| 2014/0162945 | A1 | 6/2014 | Ma et al. |
| 2014/0357552 | A1 | 12/2014 | Asami et al. |
| 2015/0031606 | A1 | 1/2015 | Vilhelmsen |
| 2016/0015788 | A1 | 1/2016 | Holscher |
| 2016/0280754 | A1 | 9/2016 | Shelton et al. |
| 2017/0112897 | A1 | 4/2017 | Talbot et al. |
| 2019/0202883 | A1 | 7/2019 | Asami et al. |
| 2020/0023040 | A1 | 1/2020 | Benson et al. |
| 2020/0079832 | A1 | 3/2020 | Holscher |

FOREIGN PATENT DOCUMENTS

| | | |
|---|---|---|
| CN | 110642935 | 1/2020 |
| CN | 110684082 | 1/2020 |
| WO | 2010011439 A2 | 1/2010 |
| WO | 2010071807 A1 | 6/2010 |
| WO | 10080605 A1 | 7/2010 |
| WO | 2010148089 A1 | 12/2010 |
| WO | 2011080103 A1 | 7/2011 |
| WO | 11162968 A1 | 12/2011 |
| WO | 11163012 A2 | 12/2011 |
| WO | 2012080471 A1 | 6/2012 |
| WO | 2012088379 A2 | 6/2012 |
| WO | 2013164483 A1 | 11/2013 |
| WO | 2013189988 A1 | 12/2013 |
| WO | 2014152460 A2 | 9/2014 |
| WO | 2014177683 A1 | 11/2014 |
| WO | 2014192284 A1 | 12/2014 |
| WO | 2015022420 A1 | 2/2015 |
| WO | 2015035419 | 3/2015 |
| WO | 2015067715 A2 | 5/2015 |
| WO | 2015086728 | 6/2015 |
| WO | 2015086729 A1 | 6/2015 |
| WO | 2016049174 A1 | 3/2016 |
| WO | 2016077220 | 5/2016 |
| WO | 2016084826 | 6/2016 |
| WO | 2016111971 | 7/2016 |
| WO | 2016131893 | 8/2016 |
| WO | 2018181864 | 10/2018 |
| WO | 2019149880 A1 | 8/2019 |
| WO | 2020023386 | 1/2020 |
| WO | 2020023388 | 1/2020 |
| WO | WO 2020/207477 | * 10/2020 |
| WO | 2021068251 | 4/2021 |
| WO | 2022018186 A1 | 1/2022 |

OTHER PUBLICATIONS

Bastin et al. "'Dual GIP-GLP1-Receptor Agonists in the Treatment of Type 2 Diabetes: A Short Review on Emerging Data and Therapeutic Potential.'" Diabetes, metabolic syndrome and obesity: targets and therapy, Sep. 2019, vol. 12, pp. 1973-1985.

Buckley, Stephen T. et al., "Transcellular stomach absorption of a derivatized glucagon-like peptide-1 receptor agonist" Science Translational Medicine, Nov. 14, 2018, vol. 10, No. 467, eaar7047 pp. 1-13.

Coskun et al., "LY3298176, a novel dual GIP and GLP-1 receptor agonist for the treatment of type 2 diabetes mellitus: From discovery to clinical proof of concept," Molecular Metabolism, 2018, vol. 18, pp. 3-14.

(Continued)

*Primary Examiner* — Gyan Chandra
(74) *Attorney, Agent, or Firm* — Leon Y. Lum

(57) ABSTRACT

Peptide co-agonists of the human GLP-1 and GIP receptors suitable for oral delivery, including long-acting derivatives, and their medical use in treatment and/or prevention of obesity, diabetes, and/or liver diseases are described.

1 Claim, No Drawings

Specification includes a Sequence Listing.

(56) References Cited

OTHER PUBLICATIONS

Feng et al., Two novel dual GLP-1/GIP receptor agonists are neuroprotective in the MPTP mouse model of Parkinson's disease. Neuropharmacology, vol. 133, 2018, pp. 385-394.

Finan et al., "Unimolecular Dual Incretins Maximize Metabolic Benefits in Rodents, Monkeys, and Humans." Sci Transl Med, Oct. 2013, vol. 5, No. 209, p. 209ra151.

Finan et al.,"Reappraisal of GIP Pharmacology for Metabolic Diseases," Feature Review. Trends in Molecular Medicine, May 2016, vol. 22, No. 5, pp. 359-376.

Frias et al., "Efficacy and safety of LY3298176, a novel dual GIP and GLP-1 receptor agonist, in patients with type 2 diabetes: a randomised, placebo-controlled and active comparator-controlled phase 2 trial." Lancet, Nov. 2018, vol. 392, No. 10160, pp. 2180-2193.

Frias et al.,"The Sustained Effects of a Dual GIP/GLP-1 Receptor Agonist, NNC0090-2746, in Patients with Type 2 Diabetes." Cell Metab. Aug. 2017, vol. 26, No. 2, pp. 343-352.e2.

Hedrington et al., ""Oral semaglutide for the treatment of type 2 diabetes"" Expert Opin Pharmacother, Feb. 2019, vol. 20, No. 2, pp. 133-141.

Killion et al. "Glucose-dependent insulinotropic polypeptide receptor therapies for the treatment of obesity, do agonists= antagonists?." Endocrine reviews, Feb. 2020, vol. 41, No. 1, pp. 1-21.

Knerr et al. "Selection and progression of unimolecular agonists at the GIP, GLP-1, and glucagon receptors as drug candidates." Peptides, Mar. 2020, vol. 125, No. 170225, p. 1-12.

Mroz et al., "Optimized GIP analogs promote body weight lowering in mice through GIPR agonism not antagonism," Feb. 2019, vol. 20, pp. 51-62.

Norregaard et al., "A novel GIP analogue, ZP4165, enhances glucagon-like peptide-1-induced body weight loss and improves glycaemic control in rodents." Diabetes Obes Metab., Jan. 2018, vol. 20, No. 1, pp. 60-68.

Schmitt et al. "Pharmacodynamics, pharmacokinetics and safety of multiple ascending doses of the novel dual glucose?dependent insulinotropic polypeptide/glucagon?like peptide?1 agonist RG 7697 in people with type 2 diabetes mellitus." Diabetes, Obesity and Metabolism, Jul. 2017, vol. 19, No. 10 , pp. 1436-1445.

Arnab et al., ""Synthesis and Characterization of Ester-Based Prodrugs of Glucagon-Like Peptide 1"", Peptide Science, Jun. 2010, vol. 94, No. 4, Special Issue SI, pp. 448-456.

Baggio et al., "Glucagon-like peptide-1 receptor co-agonists for treating metabolic disease", Molecular Metabolism, Sep. 2020, vol. 46, pp. 1-14.

Coskun et al., "LY3298176, a novel dual GIP and GLP-1 receptor agonist for the treatment of type 2 diabetes mellitus: From discovery to clinical proof of concept," Molecular Metabolism, Oct. 2018, vol. 18, pp. 3-14.

Frias et al., "Tirzepatide versus Semaglutide Once Weekly in Patients with Type 2 Diabetes", The New England Journal of Medicine, Aug. 5, 2021, vol. 385, pp. 503-515.

Gault et al., "Administration of an acylated GLP-1 and GIP preparation provides added beneficial glucose-lowering and insulinotropic actions over single incretins in mice with Type 2 diabetes and obesity", Clinical Science, Apr. 2011, vol. 121, No. 3, pp. 107-117.

Hornigold et al., "A GLP-1:CCK fusion peptide harnesses the synergistic effects on metabolism of CCK-1 and GLP-1 receptor agonism in mice", Appetite, May 2018, vol. 127, pp. 334-340.

Lafferty et al., "Proglucagon-Derived Peptides as Therapeutics", Frontiers in Endocrinology, May 18, 2021, vol. 12, pp. 1-29.

Nauck et al., "Additive insulinotropic effects of exogenous synthetic human gastric inhibitory polypeptide and glucagon-like peptide-1-(7-36) amide infused at near-physiological insulinotropic hormone and glucose concentrations", J Clin Endocrinol Metab, Apr. 1993, vol. 76, No. 4, pp. 912-917.

Nauck et al., "The evolving story of incretins (GIP and GLP-1) in metabolic and cardiovascular disease: A pathophysiological update", Diabetes, Obesity & Metabolism, Jul. 2021, vol. 23, No. S3, pp. 5-29.

PCT Application No. PCT/EP2021/068985, filed Jul. 8, 2021.

Rosenstock et al., "Efficacy and safety of a novel dual GIP and GLP-1 receptor agonist tirzepatide in patients with type 2 diabetes (SURPASS-1): a double-blind, randomised, phase 3 trial", Lancet, Jul. 2021, vol. 398, No. 10295, pp. 143-155.

Salama et al., "The Impact of ?G on the Oral Bioavailability of Low Bioavailable Therapeutic Agents", Journal of Pharmacology and Experimental Therapeutics, Feb. 2005, vol. 312, pp. 199-205.

Testa et al., "Introduction: Metabolic Hydrolysis and Prodrug Design", 2003, pp. 1-9.

Thomas et al., "Dual GIP and GLP-1 Receptor Agonist Tirzepatide Improves Beta-cell Function and Insulin Sensitivity in Type 2 Diabetes", JCEM, Feb. 2021, vol. 106, No. 2, pp. 388-396.

Yu et al., "The effect of food on the relative bioavailability of rapidly dissolving immediate-release solid oral products containing highly soluble drugs", Molecular Pharmaceutics, Aug. 2004, vol. 1, No. 5, pp. 357-362.

Gomes et al., "Cyclization-activated Prodrugs", Molecules, Nov. 2007, vol. 12, No. 11, pp. 2484-2506.

* cited by examiner

CO-AGONISTS AT GLP-1 AND GIP RECEPTORS SUITABLE FOR ORAL DELIVERY

CROSS-REFERENCE TO RELATED APPLICATIONS

This application is a Continuation of International Application No. PCT/EP2021/070485, filed Jul. 22, 2021 and claims priority under 35 U.S.C. § 119 to U.S. Provisional Application 63/156,988, filed Mar. 5, 2021, U.S. Provisional Application 63/055,026, filed Jul. 22, 2020 and European Patent Application 20192414.9, filed Aug. 24, 2020; the contents of which are incorporated herein by reference.

TECHNICAL FIELD OF THE INVENTION

The present invention relates to novel compounds that are agonists of the glucagon-like peptide 1 (GLP-1) receptor and the glucose-dependent insulinotropic polypeptide (GIP) receptor with a protracted profile of action, suitable for oral administration to humans.

INCORPORATION-BY-REFERENCE OF THE SEQUENCE LISTING

The instant application contains a Sequence Listing which has been submitted in ASCII format via EFS-Web and is hereby incorporated by reference in its entirety. Said ASCII copy, created on Jan. 7, 2021, is named "200018_sequence_listing_NEW_ST25", and is 27 kilobytes in size.

BACKGROUND

Glucagon-like peptide 1 (GLP-1) is a gut enteroendocrine cell-derived hormone and one of two prominent endogenous physiological incretins. GLP-1 improves glycemic control by stimulating glucose-dependent insulin secretion in response to nutrients (glucose), inhibits glucagon secretion from the pancreatic alpha-cells, slows gastric emptying, and induces body weight loss primary by decreasing food consumption. Glucose-dependent insulinotropic polypeptide (GIP), the other prominent incretin, improves glycemic control by stimulation of insulin secretion in response to nutrients (fat, glucose). Furthermore, GIP appears to improve plasma lipid profile and to stimulate calcium accumulation in bones. In contrast to GLP-1, the incretin effect of GIP is severely reduced in type 2 diabetes patients, though recent studies suggest that GIP efficiency can be regained in these patients after treatment to improve glucose control. Nonetheless, the role of GIP to regulate systemic metabolism beyond its direct effect at the endocrine pancreas remains controversial, particularly as it relates to GIP action to promote gain in fat mass in animal models. These results have fostered beliefs that GIPR antagonism can improve body weight. Thus, employment of compounds acting at GIP receptors, and specifically whether to agonize or antagonize, as a strategy to improve body weight remains a contentious subject of intense scientific investigation (Finan et al, TRENDS Mol Med, 2016, 22 (5): 359-376; Killion et al, Endo Rev, 2020, 41 (1): 1-21).

Protracted GIP analogs have been shown to lower body weight and improve glycemic control, though comparatively less potent than GLP-1 analogs to lower body weight in rodent models (Mroz et al, Mol Metab, 2019, 20: 51-62). Moreover, GIP analogs induce body weight loss by additive/synergistic action with GLP-1 analogs in dual administration (Finan et al, Sci Transl Med, 2013, 5 (209): 209ra151; Norregaard et al, Diabetes Obes Metab, 2018, 20 (1): 60-68), and as such represent suitable candidates for amplification of GLP-1-based pharmacology. GIPR agonism can be recruited as a non-redundant partner to GLP-1 R agonism as a single molecule co-agonist to amplify GLP-1 metabolic benefits, as has been shown in preclinical animal models, most notably body weight loss and glycemic control (Finan et al, Sci Transl Med, 2013, 5 (209): 209ra151; Coskun et al, Mol Metab, 2018, 18: 3-14). Two different peptides with high potency dual incretin receptor agonism have advanced to multi-dose clinical studies. The clinical results have demonstrated improvements in glycemic control and body weight that exceeds what is achieved with comparable dosing of benchmark GLP-1 specific agonists (Frias et al, Cell Metab, 2017, 26 (2): 343-352; Frias et al, Lancet, 2018, 392 (10160): 2180-2193), demonstrating the translational aspects and therapeutic benefits of co-targeting GLP-1 and GIP receptors.

Oral delivery of GLP-1 derivatives has been investigated clinically in the form of a once-daily tablet of semaglutide and the permeation enhancer sodium N-[8-(2-hydroxybenzoyl)amino]caprylate (SNAC) (Hedrington & Davis, Exp. Opin. Pharmacother. 2019, 20 (2): 133-141) to improve the very low typical exposure and bioavailability of GLP-1 derivatives following oral administration.

GLP-1/GIP co-agonists and their potential medical uses are described in several patent applications such as WO 2010/011439, WO 2013/164483, WO 2014/192284, WO 2015/067715, WO 2015/022420, WO 2015/086728, WO 2015/086729, WO 2016/111971, WO 2020/023386, U.S. Pat. No. 9,745,360, US 2014/162945, and US 2014/0357552. Patent applications disclosing oral delivery of GLP-1 derivatives are described in e.g. WO 2011/080103, WO 2012/080471, WO 2013/189988, and WO 2019/149880.

However, no co-agonistic products have so far obtained market approval.

SUMMARY

The present invention relates to single molecule co-agonists comprising a peptide and a substituent, which react with both the human GLP-1 and GIP receptors with high potency and are suitable for daily oral administration to humans. This is achieved by the combination of certain peptide sequence variants with substituents via a single site acylation with a diacid based fatty acid.

An aspect of the invention relates to a peptide having the amino acid sequence (SEQ ID NO.: 36)
$YX_2EGTX_6TSDYSX_{12}X_{13}LEX_{16}QAAX_{20}X_{21}FX_{23}X_{24}WLLX_{28}GGPX_{32}X_{33}$
$X_{34}X_{35}X_{36}X_{37}X_{38}X_{39}$ with an optional amide modification of the C-terminus; wherein
$X_2$ is Aib or A
$X_6$ is F or V
$X_{12}$ is I or Y
$X_{13}$ is Y, A, L or I
$X_{16}$ is K or E
$X_{20}$ is Q, R, E, H
$X_{21}$ is A or E
$X_{23}$ is I or V
$X_{24}$ is E, Q or N $X_{28}$ is A or R
$X_{32}$ is E, S or absent
$X_{33}$ is S, K or absent
$X_{34}$ is G or absent
$X_{35}$ is A or absent
$X_{36}$ is P or absent
$X_{37}$ is P or absent
$X_{38}$ is P or absent
$X_{39}$ is S or absent.

In another aspect, the invention relates to a peptide having the amino acid sequence (SEQ ID NO.: 36)
YX$_2$EGTX$_6$TSDYSX$_{12}$X$_{13}$LEX$_{16}$QAAX$_{20}$X$_{21}$FX$_{23}$X$_{24}$WLLX$_{28}$GGPX$_{32}$X$_{33}$X$_{34}$X$_{35}$X$_{36}$X$_{37}$X$_{38}$X$_{39}$ with an optional amide modification of the C-terminus, wherein
$X_2$ is Aib or A
$X_6$ is F or V
$X_{12}$ is I or Y
$X_{13}$ is Y, A, L or I
$X_{16}$ is K or E
$X_{20}$ is Q, R, E, H
$X_{21}$ is A or E
$X_{23}$ is I or V
$X_{24}$ is E, Q or N
$X_{28}$ is A or R
$X_{32}$ is E, S or absent
$X_{33}$ is S, K or absent
$X_{34}$ is G or absent
$X_{35}$ is A or absent
$X_{36}$ is P or absent
$X_{37}$ is P or absent
$X_{38}$ is P or absent
$X_{39}$ is S or absent;
and a substituent attached to the peptide via Lysine (K) at position 16 or 33;
or a pharmaceutically acceptable salt hereof.

A further aspect of the invention relates to a method for preparing the GLP-1/GIP co-agonists described herein.

In a further aspect the invention relates to a pharmaceutical composition comprising the GLP-1/GIP co-agonists compounds described herein.

A further aspect of the invention relates to medical use of the GLP-1/GIP co-agonists described herein.

In one aspect the invention relates to use of the GLP-1/GIP co-agonists described herein for prevention or treatment of diabetes, obesity, and/or liver diseases.

DESCRIPTION

In what follows, Greek letters may be represented by their symbol or the corresponding written name, for example: α=alpha; β=beta; ε=epsilon; γ=gamma; ω=omega; etc. Also, the Greek letter of μ may be represented by "u", e.g. in μl=ul, or in μM=uM.

GLP-1/GIP Receptor Co-Agonist

The present invention relates to compounds that are GLP-1 receptor and the GIP receptor agonists, also referred to as GLP-1/GIP receptor co-agonists or simply co-agonists.

The term "compound" is used herein to refer to a molecular entity, and "compounds" may thus have different structural elements besides the minimum element defined for each compound or group of compounds. It follows that a compound may be a peptide or a derivative thereof, as long as the compound comprises the defined structural and/or functional elements.

The term "compound" is also meant to cover pharmaceutically relevant forms hereof, i.e. a compound as defined herein or a pharmaceutically acceptable salt, amide, or ester thereof.

The term "analogue" generally refers to a peptide, the sequence of which has one or more amino acid changes when compared to a reference amino acid sequence. An "analogue" may also include amino acid elongations in the N-terminal and/or C-terminal positions and/or truncations in the N-terminal and/or C-terminal positions.

In general, amino acid residues may be identified by their full name, their one-letter code, and/or their three-letter code. These three ways are fully equivalent.

Amino acids are molecules containing an amino group and a carboxylic acid group, and, optionally, one or more additional groups, often referred to as a side chain.

The term "amino acid" includes proteinogenic (or natural) amino acids (amongst those the 20 standard amino acids), as well as non-proteinogenic (or non-natural) amino acids. Proteinogenic amino acids are those which are naturally incorporated into proteins. The standard amino acids are those encoded by the genetic code. Non-proteinogenic amino acids are either not found in proteins, or not produced by standard cellular machinery (e.g., they may have been subject to post-translational modification). Non-limiting examples of non-proteinogenic amino acids are Aib (a-aminoisobutyric acid, or 2-aminoisobutyric acid), norleucine, norvaline as well as the D-isomers of the proteinogenic amino acids.

In what follows, each amino acid of the peptides for which the optical isomer is not stated is to be understood to mean the L-isomer (unless otherwise specified).

The GLP-1/GIP receptor co-agonists described herein comprise or consist of a peptide and a substituent as defined below. In some embodiments, the peptide is a synthetic peptide created to optimize the activity at the GLP-1 and GIP receptors. Compounds having a suitable receptor binding activity towards both the GLP-1 receptor and the GIP receptor have been identified as demonstrated in the examples herein.

The compounds further display an extended half-life gained by the substituent comprising a fatty acid group.

In some embodiments, the carboxy terminus of a peptide holds a —COON group. In some embodiments, the compounds may optionally include an amide group (C(=O)—NH$_2$) at the C-terminus, which is a naturally occurring modification substituting —OH with —NH$_2$, such as seen with native Exendin-4.

Peptide

The GLP-1/GIP receptor co-agonists described herein comprise a peptide and a substituent as defined below, in which the substituent is attached to the peptide backbone via an amino acid residue.

In some embodiments, the amino acid sequence of the peptide is (SEQ ID NO.: 47)
YX$_2$EGTX$_6$TSDYSX$_{12}$X$_{13}$LEX$_{16}$QAAX$_{20}$X$_{21}$FX$_{23}$X$_{24}$WLLX$_{28}$GX$_{30}$X$_{31}$X$_{32}$X$_{33}$X$_{34}$X$_{35}$X$_{36}$X$_{37}$X$_{38}$X$_{39}$ with an optional amide modification of the C-terminus; wherein
$X_2$ is Aib or A
$X_6$ is F or V $X_{12}$ is I or Y
$X_{13}$ is Y, A, L or I
$X_{16}$ is K or E
$X_{20}$ is Q, R, E, H
$X_{21}$ is A or E
$X_{23}$ is I or V
$X_{24}$ is E, Q or N
$X_{28}$ is A or R
$X_{30}$ is G or absent
$X_{31}$ is P or absent
$X_{32}$ is E, S or absent
$X_{33}$ is S, K or absent
$X_{34}$ is G or absent
$X_{35}$ is A or absent
$X_{36}$ is P or absent
$X_{37}$ is P or absent
$X_{38}$ is P or absent
$X_{39}$ is S or absent.

In some embodiments, the amino acid sequence of the peptide is (SEQ ID NO.: 36)
$YX_2EGTX_6TSDYSX_{12}X_{13}LEX_{16}QAAX_{20}X_{21}FX_{23}X_{24}WLLX_{28}GGPX_{32}X_{33}X_{34}X_{35}X_{36}X_{37}X_{38}X_{39}$ with an optional amide modification of the C-terminus; wherein
$X_2$ is Aib or A
$X_6$ is F or V
$X_{12}$ is I or Y
$X_{13}$ is Y, A, L or I
$X_{16}$ is K or E
$X_{20}$ is Q, R, E, H
$X_{21}$ is A or E
$X_{23}$ is I or V
$X_{24}$ is E, Q or N
$X_{28}$ is A or R
$X_{32}$ is E, S or absent
$X_{33}$ is S, K or absent
$X_{34}$ is G or absent
$X_{35}$ is A or absent
$X_{36}$ is P or absent
$X_{37}$ is P or absent
$X_{38}$ is P or absent
$X_{39}$ is S or absent.

In one embodiment, $X_{39}$ is absent. In one embodiment, $X_{38}$ and $X_{39}$ are absent. In one embodiment, $X_{37}$, $X_{38}$ and $X_{39}$ are absent. In one embodiment, $X_{36}$, $X_{37}$, $X_{38}$ and $X_{39}$ are absent. In one embodiment, $X_{35}$, $X_{36}$, $X_{37}$, $X_{38}$ and $X_{39}$ are absent. In one embodiment, $X_{34}$, $X_{35}$, $X_{36}$, $X_{37}$, $X_{38}$ and $X_{39}$ are absent. In one embodiment, $X_{33}$, $X_{34}$, $X_{35}$, $X_{36}$, $X_{37}$, $X_{38}$ and $X_{39}$ are absent. In one embodiment, $X_{32}$, $X_{33}$, $X_{34}$, $X_{35}$, $X_{36}$, $X_{37}$, $X_{38}$ and $X_{39}$ are absent. In one embodiment, $X_{31}$, $X_{32}$, $X_{33}$, $X_{34}$, $X_{35}$, $X_{36}$, $X_{37}$, $X_{38}$ and $X_{39}$ are absent. In one embodiment, $X_{30}$, $X_{31}$, $X_{32}$, $X_{33}$, $X_{34}$, $X_{35}$, $X_{36}$, $X_{37}$, $X_{38}$ and $X_{39}$ are absent. In further such embodiments, $X_{32}X_{33}X_{34}X_{35}$ is SSGA (SEQ ID NO.: 40). In further such embodiments, $X_{32}X_{33}X_{34}X_{35}$ is ESGA (SEQ ID NO.: 41). In further such embodiments, $X_{32}X_{33}X_{34}X_{35}$ is SKGA (SEQ ID NO.: 42). In a further embodiment thereof, the peptide has an amide modification of the C-terminus.

In one embodiment, the amino acid sequence of the peptide is (SEQ ID NO.: 37)
$YX_2EGTX_6TSDYSX_{12}X_{13}LEX_{16}QAAX_{20}X_{21}FX_{23}X_{24}WLLX_{28}GGPSSGAPPPS$ wherein
$X_2$ is Aib or A
$X_6$ is F or V
$X_{12}$ is I or Y
$X_{13}$ is Y, A, L or I
$X_{16}$ is K or E
$X_{20}$ is Q, R, E, H
$X_{21}$ is A or E
$X_{23}$ is I or V
$X_{24}$ is E, Q or N
$X_{28}$ is A or R.

In one embodiment, the amino acid seauence of the peptide is (SEQ ID NO.: 38)
$YX_2EGTX_6TSDYSX_{12}X_{13}LEX_{16}QAAX_{20}X_{21}FX_{23}X_{24}WLLX_{28}GGPESGAPPPS$ wherein
$X_2$ is Aib or A
$X_6$ is F or V
$X_{12}$ is I or Y
$X_{13}$ is Y, A, L or I
$X_{16}$ is K or E
$X_{20}$ is Q, R, E, H
$X_{21}$ is A or E
$X_{23}$ is I or V
$X_{24}$ is E, Q or N
$X_{28}$ is A or R.

In one embodiment, the amino acid sequence of the peptide is (SEQ ID NO.: 39)
$YX_2EGTX_6TSDYSX_{12}X_{13}LEX_{16}QAAX_{20}X_{21}FX_{23}X_{24}WLLX_{28}GGPSKGAPPPS$ wherein
$X_2$ is Aib or A
$X_6$ is F or V
$X_{12}$ is I or Y
$X_{13}$ is Y, A, L or I
$X_{16}$ is K or E
$X_{20}$ is Q, R, E, H
$X_{21}$ is A or E
$X_{23}$ is I or V
$X_{24}$ is E, Q or N
$X_{28}$ is A or R.

In one embodiment, $X_2$ is Aib. In one embodiment, $X_2$ is A. In one embodiment, $X_6$ is F. In one embodiment, $X_6$ is V. In one embodiment, $X_{12}$ is I. In one embodiment, $X_{12}$ is Y. In one embodiment, $X_{13}$ is Y. In one embodiment, $X_{13}$ is A. In one embodiment, $X_{13}$ is L. In one embodiment, $X_{13}$ is I. In one embodiment, $X_{16}$ is K. In one embodiment, $X_{16}$ is E. In one embodiment, $X_{20}$ is Q. In one embodiment, $X_{20}$ is R. In one embodiment, $X_{20}$ is E. In one embodiment, $X_{20}$ is H. In one embodiment, $X_{21}$ is A. In one embodiment, $X_{21}$ is E. In one embodiment, $X_{23}$ is I. In one embodiment, $X_{23}$ is V. In one embodiment, $X_{24}$ is E. In one embodiment, $X_{24}$ is Q. In one embodiment, $X_{24}$ is N. In one embodiment, $X_{28}$ is A. In one embodiment, $X_{28}$ is R. In one embodiment, $X_{30}$ is G. In one embodiment, $X_{31}$ is P.

In one embodiment, $X_{13}LEX_{16}QAAX_{20}X_{21}FX_{23}X_{24}$ is selected from the group consisting of:

LLEKQAAREFIN, (SEQ ID NO.: 43)

LLEKQAAREFIE, (SEQ ID NO.: 44)

LLEKQAAQEFIE (SEQ ID NO.: 45)
and

LLEEQAAREFIE. (SEQ ID NO.: 46)

In one embodiment,
$X_{13}LEX_{16}QAAX_{20}X_{21}FX_{23}X_{24}$ is LLEKQAAREFIN. (SEQ ID NO.: 43)

In one embodiment,
$X_{13}LEX_{16}QAAX_{20}X_{21}FX_{23}X_{24}$ is LLEKQAAREFIE. (SEQ ID NO.: 44)

In one embodiment,
$X_{13}LEX_{16}QAAX_{20}X_{21}FX_{23}X_{24}$ is LLEKQAAQEFIE. (SEQ ID NO.: 45)

In one embodiment,
$X_{13}LEX_{16}QAAX_{20}X_{21}FX_{23}X_{24}$ is LLEEQAAREFIE. (SEQ ID NO.: 46)

In a further embodiment, the amino acid sequence of the peptide is any one of SEQ ID NO.: 1, 2, 3, 4, 5, 6, 7, 8, 9, 10, 11, 12, 13, 14, 15, 16, 17, 18, 19, 20, 21, 22, 23, 24, 25, 26, 27, 33, 34 and 35.

In one embodiment, the amino acid sequence of the peptide is any one of SEQ ID NO.: 10, 22 or 25.

In one embodiment, the amino acid sequence of the peptide is SEQ ID NO.: 25.

In one embodiment, the amino acid sequence of the peptide is any one of SEQ ID NO.: 18, 20, 23, 24.

In one embodiment, the amino acid sequence of the peptide is SEQ ID NO.: 33, 34 or 35.

In further such embodiments, the peptide has an amide modification of the C-terminus.

Derivatives

In some embodiments, the GLP-1 and GIP receptor agonists comprise or consist of a substituent as defined below covalently linked to a peptide.

Such compounds may be referred to as derivatives of the peptide, as they are obtained by covalently linking a substituent to a peptide backbone.

An aspect of the invention relates to a compound comprising a peptide and a substituent; wherein the amino acid sequence of the peptide is:

$YX_2EGTX_6TSDYSX_{12}X_{13}LEX_{16}QAAX_{20}X_{21}FX_{23}X_{24}WLLX_{28}GX_{30}X_{31}X_{32}$
$X_{33}X_{34}X_{35}X_{36}X_{37}X_{38}X_{39}$ (SEQ ID NO.: 47)

with an optional amide modification of the C-terminus, wherein
$X_2$ is Aib or A
$X_6$ is F or V
$X_{12}$ is I or Y
$X_{13}$ is Y, A, L or I
$X_{16}$ is K or E
$X_{20}$ is Q, R, E, H
$X_{21}$ is A or E
$X_{23}$ is I or V
$X_{24}$ is E, Q or N
$X_{28}$ is A or R
$X_{30}$ is G or absent
$X_{31}$ is P or absent
$X_{32}$ is E, S or absent
$X_{33}$ is S, K or absent
$X_{34}$ is G or absent
$X_{35}$ is A or absent
$X_{36}$ is P or absent
$X_{37}$ is P or absent
$X_{38}$ is P or absent
$X_{39}$ is S or absent;
and wherein the substituent is attached to the peptide Lysine (K) at position 16 or 33;
or a pharmaceutically acceptable salt hereof.

An embodiment of the invention relates to a compound comprising a peptide and a substituent; wherein the amino acid sequence of the peptide is:

$YX_2EGTX_6TSDYSX_{12}X_{13}LEX_{16}QAAX_{20}X_{21}FX_{23}X_{24}WLLX_{28}GGPX_{32}X_{33}$
$X_{34}X_{35}X_{36}X_{37}X_{38}X_{39}$ (SEQ ID NO.: 36)

with an optional amide modification of the C-terminus, wherein
$X_2$ is Aib or A
$X_6$ is F or V
$X_{12}$ is I or Y
$X_{13}$ is Y, A, L or I
$X_{16}$ is K or E
$X_{20}$ is Q, R, E, H
$X_{21}$ is A or E
$X_{23}$ is I or V
$X_{24}$ is E, Q or N
$X_{28}$ is A or R
$X_{32}$ is E, S or absent
$X_{33}$ is S, K or absent
$X_{34}$ is G or absent
$X_{35}$ is A or absent
$X_{36}$ is P or absent
$X_{37}$ is P or absent
$X_{38}$ is P or absent
$X_{39}$ is S or absent;
and wherein the substituent is attached to the peptide via Lysine (K) at position 16 or 33;
or a pharmaceutically acceptable salt hereof.

In further embodiments, the peptide may be defined as described herein above.

Substituent

In one embodiment, the substituents described herein are attached to the peptide described herein via a lysine (K) residue in position 16 or 33.

In one embodiment, the substituent is attached to the peptide via the epsilon-amino group of a Lysine (K) when said Lysine is included at position 16 or 33.

In one embodiment, the substituent is a chemical structure covalently attached to the peptide that is capable of forming non-covalent complexes with plasma albumin, thereby promoting the circulation of the co-agonist with the blood stream, and also having the effect of protracting the time of action of the co-agonist, due to the fact that the complex of the co-agonist and albumin is only slowly removed by renal clearance.

In one embodiment, the substituent comprises a fatty acid group. In such embodiment, the fatty acid group comprises a carbon chain which contains at least 8 consecutive —CH$_2$— groups. In one embodiment, the fatty acid group comprises at least 10 consecutive —CH$_2$— groups, such as least 12 consecutive —CH$_2$— groups, at least 14 consecutive —CH$_2$— groups, at least 16 consecutive —CH$_2$— groups, or such as at least 18 consecutive —CH$_2$— groups.

In one embodiment, the fatty acid group comprises 8-20 consecutive —CH$_2$— groups. In one embodiment, the fatty acid group comprises 10-18 consecutive —CH$_2$— groups. In one embodiment, the fatty acid group comprises 12-18 consecutive —CH$_2$— groups. In one embodiment, the fatty acid group comprises 14-18 consecutive —CH$_2$— groups.

In some embodiments, the substituent consists of several elements, such as a protractor element and one or more linker elements. In one embodiment, the term "protractor" is used to describe the fatty acid group which is the terminal part of the substituent responsible for extending half-life of the compound. In one embodiment, the protractor (Prot) may be defined by:

Chem. 1: HOOC—(CH$_2$)$_n$—CO—* wherein n is an integer in the range of 8-20, which may also be referred to as a C(n+2) diacid or as Chem. 1 b:

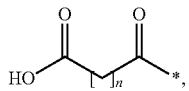

wherein n is an integer in the range of 8-20.

In one embodiment, the substituent further comprises one or more linker elements.

In some embodiments, the linker elements are linked to each other and the protractor by amide bonds and referred to as "Z" (see further below).

As further defined herein below the number of linker elements may be at most 3, referred to as -Z1-Z2-Z3- where Z1 is connected with the protractor (Prot) and the last Z element is connected with the peptide, in which case the substituent may be referred to as Prot-Z1-Z2-Z3-. The symbol * above thus indicates the attachment point to Z1, which when bound via an amide bond is a nitrogen. In an embodiment, where Z1 is a bond (see below), the symbol * indicates the attachment point to the nitrogen of the neighbouring Z element.

In one embodiment, the substituent is defined by: Prot-Z1-Z2-Z3- wherein Prot- is selected from Chem1, Chem 1 b, and wherein n is an integer in the range of 16-20.

In a particular embodiment, n is 14, 15, 16, 17, 18, 19 or 20 in Chem. 1 or Chem. 1b.

In a particular embodiment, n is 14, 15, 16, 17, or 18 in Chem. 1 or Chem. 1 b.

In a particular embodiment, n is 14, 16, or 18 in Chem. 1 or Chem. 1 b.

In a particular embodiment, n is 16, 17, 18, 19 or 20 in Chem. 1 or Chem. 1 b.

In a particular embodiment, n is 16, 18 or 20 in Chem. 1 or Chem. 1b.

In a particular embodiment, n is 18 or 20 in Chem. 1 or Chem. 1 b.

In a particular embodiment, the protractor (Prot) is a C16 diacid or a C18 diacid.

In a particular embodiment, the protractor (Prot) is a C18 diacid or a C20 diacid.

In a particular embodiment, the protractor (Prot) is a C16, C18 diacid or a C20 diacid.

The term "bond" as used here means a covalent bond. When a linker element of Z1-Z3 is defined as a bond, it is equivalent to a situation wherein said linker element is absent. The indication herein below that any of Z1-Z3 is a bond may also be read as any of Z1-Z3 being absent, so that the previous Z element is covalently linked to the next Z element that is not "a bond" (or absent).

In some embodiments, the linker elements Z1-Z3 are individually selected from chemical moieties capable of forming amide bonds, including amino acid like moieties, such as Glu, γGlu (also termed gamma Glu or gGlu and defined by *—NH—CH—(COOH)—CH$_2$—CH$_2$—CO—*), ε-Lys (also termed epsilon Lys or eLys and defined by *—NH—(CH$_2$)$_4$—CH(NH$_2$)—CO—*), Ser, Ala, Thr, Ado, Aeep and Aeeep and further moieties as described below.

In one embodiment, Z1 is selected from γGlu, Glu, or a bond. In one embodiment, Z1 is γGlu.

In one embodiment, Z2 and Z3, are selected, independently of each other, from Glu, ε-Lys, γGlu, Gly, Ser, Ala, Thr, Ado, Aeep, Aeeep and a bond.

Glu, Gly, Ser, Ala, Thr are amino acid residues well known in the art.

ε-Lys is defined by Chem. 2: *—NH—(CH$_2$)$_4$—CH(NH$_2$)—CO—* which may also be described by Chem. 2b:

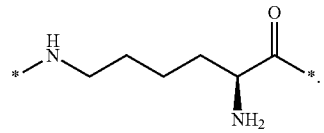

γGlu is defined by Chem. 3: *—NH—CH(COOH)—(CH$_2$)$_2$—CO—* which may also be described by Chem. 3b:

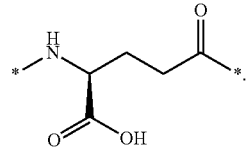

Ado is defined by Chem. 4: *—NH—(CH$_2$)$_2$—O—(CH$_2$)$_2$—O—CH$_2$—CO—* may also be referred to as 8-amino-3,6-dioxaoctanoic acid and which may also be described by

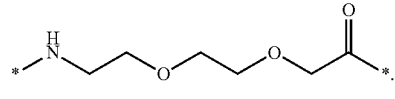

Chem. 4b:
Aeep is defined by Chem. 5: *NH—CH$_2$CH$_2$OCH$_2$CH$_2$OCH$_2$CH$_2$CO*, which may also be described by Chem. 5b:

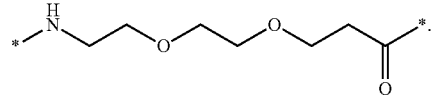

Aeeep is defined of Chem. 6: *NH—CH$_2$CH$_2$OCH$_2$CH$_2$OCH$_2$CH$_2$OCH$_2$CH$_2$CO*, which may also be described by Chem. 6b:

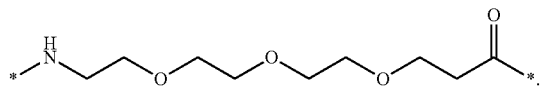

In one embodiment, Z2 and Z3 are selected, independently of each other, from Glu, ε-Lys, γGlu, Gly, Ala, Ado, Aeep, Aeeep and a bond.

In one embodiment, Z2 and Z3 are selected, independently of each other, from Glu, ε-Lys, γGlu, Gly, Ala, Ado and a bond.

In one embodiment, Z2 and Z3 are selected, independently of each other, from Glu, ε-Lys, εGlu, Gly, Ado and a bond.

In one embodiment, Z2 and Z3 are selected, independently of each other, from ε-Lys, γGlu, Gly, Ado and a bond.

In one embodiment, Z2 and Z3 are selected, independently of each other, from ε-Lys, γGlu, Ado and a bond.

In one embodiment, Z2 and Z3 are ε-Lys or Ado.

In one embodiment, Z2 and Z3 are Ado.

In one embodiment, Z2 and Z3 are ε-Lys.

In one embodiment, the substituent is selected from substituents A, B, C, D, and E defined as below.

In one embodiment, the substituent is selected from substituents A, B and C defined as follows:

| Substituent # | Prot | Z1 | Z2 | Z3 |
|---|---|---|---|---|
| A | C18 diacid | γGlu | Ado | Ado |
| B | C18 diacid | γGlu | εLys | εLys |
| C | C20 diacid | γGlu | εLys | εLys |
| D | C16 diacid | γGlu | Ado | Ado |
| E | C16 diacid | γGlu | εLys | εLys |

In some embodiments, the substituent is covalently attached to a lysine residue of the co-agonist by acylation, i.e. via an amide bond formed between a carboxylic acid group of the substituent and the epsilon-amino group of the lysine residue.

In one embodiment, the substituent is covalently attached to a lysine residue in position 16 of the peptide backbone by acylation, i.e., via an amide bond formed between a carboxylic acid group of the substituent and the epsilon amino group of the lysine residue.

In one embodiment, the substituent is covalently attached to a lysine residue in position 33 of the peptide backbone by acylation, i.e., via an amide bond formed between a carboxylic acid group of the substituent and the epsilon amino group of the lysine residue.

The co-agonists may exist in different stereoisomeric forms having the same molecular formula and sequence of bonded atoms but differing only in the three-dimensional orientation of their atoms in space. The stereoisomerism of the exemplified co-agonists is indicated in the experimental section, in the names as well as the structures, using standard nomenclature. Unless otherwise stated the invention relates to all stereoisomeric forms of the embodied derivative.

Functional Receptor Activation Activity

The functional activity of the GLP-1/GIP receptor agonists as described herein can be tested in vitro as described herein in Example 2.

The term half maximal effective concentration (EC$_{50}$) generally refers to the concentration which induces a response halfway between the baseline and maximum, by reference to the dose response curve. EC$_{50}$ is used as a measure of the potency of a compound and represents the concentration where 50% of its maximal effect is observed. The in vitro potency of compounds may thus be determined as described herein and the EC$_{50}$ determined. The lower the EC$_{50}$ value, the better the potency.

In order to characterize such compounds, it may further be relevant to consider the in vitro potencies relative to the native hormones of each receptor.

The in vitro potency may, e.g., be determined in a medium containing membranes expressing the appropriate GLP-1 and/or GIP receptor, and/or in an assay with whole cells expressing the appropriate GLP-1 and/or GIP receptor.

For example, the functional response of the human GLP-1 and/or GIP receptor may be measured in a reporter gene assay, e.g. in a stably transfected BHK cell line that expresses the human GLP-1 and/or GIP receptor and contains the DNA for the cAMP response element (CRE) coupled to a promoter and the gene for firefly luciferase (CRE luciferase). When cAMP is produced as a result of activation of the GLP-1 and/or GIP receptor, this in turn results in luciferase being expressed. Luciferase may be determined by adding luciferin, which by the enzyme is converted to oxyluciferin and produces bioluminescence, which is measured as a reporter of the in vitro potency. One example of such an assay is described in Example 2 as described herein. Since the compounds may include a substituent designed to bind albumin, it is also important to note that the receptor activity may be affected by the presence or absence of human serum albumin (HSA) in the assay medium. A decrease in potency of the compound in the presence of HSA, indicated by an increase in EC$_{50}$ compared to the EC$_{50}$ in the absence of HSA, indicates interaction of the compounds with HSA and predicts a protracted time of action in vivo.

In one embodiment, the compounds have potent in vitro effects to activate the human GLP-1 and GIP receptors.

In one embodiment, the compounds are capable of activating the human GLP-1 and GIP receptors in vitro with an EC$_{50}$ of less than 20 pM in CRE luciferase reporter assays as described in Example 2 herein, when performed without HSA.

In one embodiment, the compounds have an in vitro potency at the human GLP-1 and GIP receptors determined using the method of Example 2 corresponding to an EC$_{50}$ at or below 100 pM, more preferably below 50 pM, or most preferably below 20 pM.

In one embodiment, the EC$_{50}$ in human GLP-1 and GIP receptors assays are both 1-25 pM, such as 1-20 pM, such as 1-15 pM or such as 1-10 pM.

Pharmacokinetics Properties

The pharmacokinetic properties of the co-agonistic compounds may further be determined in vivo via pharmacokinetic (PK) studies. Animal models such as the mouse, rat, monkey, dog, or pig may be used to perform this characterization.

In such studies, animals are typically administered with a single dose of the drug, either intravenously, subcutaneously (s.c.), or orally (p.o.) in a relevant formulation. Blood samples are drawn at predefined time points after dosing, and samples are analysed for concentration of drug with a relevant quantitative assay. Based on these measurements, time-plasma concentration profiles for the compound of study are plotted and a so-called non-compartmental pharmacokinetic analysis of the data is performed. An important parameter is the terminal half-life as a long half-life indicates that less frequent administration of a compound may be possible. The terminal half-life (t½) in vivo may be measured using a suitable model, such as after i.v. administration in minipigs described in Example 3; or after p.o administration in dogs described in Example 4.

In one embodiment, the terminal half-life is half-life (t½) in vivo in minipigs after i.v. administration, e.g. as described in Example 3 herein.

In one embodiment, the terminal half-life in minipigs is at least 24 hours, such as at least 30 hours, or such as at least 40 hours.

In one embodiment, the terminal half-life is half-life (t½) in vivo in dogs after p.o. administration, e.g. as described in Example 4 herein.

In one embodiment, the terminal half-life in dogs is at least 24 hours, such as at least 40 hours, or such as at least 50 hours.

Pharmaceutically Acceptable Salts

In some embodiments, the co-agonists as described herein are in the form of a pharmaceutically acceptable salt. Salts are e.g. formed by a chemical reaction between a base and an acid, e.g.: $2NH_3+H_2SO_4 \rightarrow (NH_4)_2SO_4$. The salt may be a basic salt, an acid salt, or it may be neither (i.e. a neutral salt). Basic salts produce hydroxide ions and acid salts hydronium ions in water. The salts of the co-agonists may be formed with added cations or anions between anionic or cationic groups, respectively. These groups may be situated in the peptide and/or in the substituent of the derivatives. Non-limiting examples of anionic groups include any free carboxylic acid groups in the substituent, if any, as well as in the peptide. The peptide may include a free carboxylic acid group at the C-terminus, if present, as well as any free carboxylic acid group of internal acidic amino acid residues such as Asp and Glu.

Non-limiting examples of cationic groups include any free amino groups in the substituent, if any, as well as in the peptide. The peptide may include a free amino group at the N-terminus, if present, as well as any free imidazole or amino group of internal basic amino acid residues such as His, Arg, and Lys.

In a particular embodiment, the peptide or derivative is in the form of a pharmaceutically acceptable salt.

Production Processes

The co-agonists may for instance be produced by classical peptide synthesis, e.g. solid phase peptide synthesis using t-Boc or Fmoc chemistry or other well established techniques, see e.g. Greene and Wuts, "Protective Groups in Organic Synthesis", John Wiley & Sons, 1999; Florencio Zaragoza Dörwald, "Organic Synthesis on Solid Phase", Wiley-VCH Verlag GmbH, 2000; and "Fmoc Solid Phase Peptide Synthesis", Edited by W. C. Chan and P. D. White, Oxford University Press, 2000.

Alternatively, the compounds may be produced by recombinant methods, e.g. by culturing a host cell containing a DNA sequence encoding the peptide sequence and capable of expressing the peptide, in a suitable nutrient medium under conditions permitting the expression of the peptide. Non-limiting examples of host cells suitable for expression of these peptides are: Escherichia coli, Saccharomyces cerevisiae, as well as mammalian BHK or CHO cell lines.

The co-agonists that include non-natural amino acids and/or covalently attached substituents may be produced as described in the experimental part.

Specific examples of methods of preparing a number of co-agonists are included in the experimental part.

A further aspect of the invention relates to a method for preparing the peptides described herein.

A further aspect of the invention relates to a method for preparing the GLP-1/GIP co-agonists described herein.

In one embodiment, the method for preparing a compound as described herein comprises a step of solid phase peptide synthesis. The substituent may be built sequentially as part of the solid phase peptide synthesis or produced separately and attached via the lysine residue after peptide synthesis.

In one embodiment, the compounds are produced by a two-step process whereby two peptide fragments are ligated after attachment of the substituent to one of the peptide fragments.

Pharmaceutical Compositions

In a further aspect the invention relates to a pharmaceutical composition comprising a GLP-1/GIP receptor co-agonist as described herein. Compositions comprising the compound or a pharmaceutically acceptable salt hereof, and optionally one or more a pharmaceutically acceptable excipients may be prepared as is known in the art.

The term "excipient" broadly refers to any component other than the active therapeutic ingredient(s). The excipient may be an inert substance, an inactive substance, and/or a not medicinally active substance. The excipient may serve various purposes, e.g. as a carrier, vehicle, filler, binder, lubricant, glidant, disintegrant, flow control agent, crystallization inhibitor, solubilizer, stabilizer, coloring agent, flavoring agent, surfactant, emulsifier or combinations thereof and/or to improve administration, and/or to improve absorption of the active substance. The amount of each excipient used may vary within ranges conventional in the art. Techniques and excipients which may be used to formulate oral dosage forms are described in Handbook of Pharmaceutical Excipients (e.g. 8th edition, Sheskey et al., Eds., American Pharmaceuticals Association and Pharmaceutical Press, publications department of the Royal Pharmaceutical Society of Great Britain (2017), and any later editions); and Remington: The Science and Practice of Pharmacy (e.g. 22nd edition, Remington and Allen, Eds., Pharmaceutical Press (2013), and any later editions).

In one embodiment, the pharmaceutical composition may be a solid formulation, e.g. a freeze-dried or spray-dried composition, which may be used as is, or whereto the physician or the patient adds solvents, and/or diluents prior to use. In a further embodiment, the pharmaceutical composition may be a solid formulation consisting of the active ingredient, a salt of N-[8-(2-hydroxybenzoyl)amino]caprylate, and one or more further excipients as is known in the art, e.g. using any one or more of the formulations described in WO 2012/080471, WO 2013/189988, or WO 2019/149880.

Alternatively, the pharmaceutical composition is a liquid formulation, such as an aqueous formulation. Liquid compositions, suitable for injection, can be prepared using conventional techniques of the pharmaceutical industry which involve dissolving and mixing the ingredients as appropriate to give the desired end product. Thus, according to one procedure, a GLP-1/GIP co-agonist as described herein is dissolved in a suitable buffer at a suitable pH. The composition may be sterilized, for example, by sterile filtration.

Pharmaceutical Indications

A further aspect of the invention relates to the use of GLP-1/GIP receptor co-agonist compounds as described herein as a medicament.

In one embodiment, the compounds described herein are for use in the following medical treatments:

(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(iv) weight maintenance after successful weight loss (either drug induced or by diet and exercise)—i.e. prevention of weight gain after successful weight loss.

(v) prevention and/or treatment of liver disorders, such as hepatic steatosis, non-alcoholic fatty liver disease (NAFLD), non-alcoholic steatohepatitis (NASH), liver inflammation or fatty liver.

In one embodiment, the compounds are for use in a method for prevention and/or treatment of diabetes and/or obesity.

In one embodiment, the compounds are for use in a method for treatment of diabetes and/or obesity.

In one embodiment, the compounds are for use in a method for treatment or prevention of type 2 diabetes.

In one embodiment, the compounds are for use in a method for treatment of type 2 diabetes.

In one embodiment, the compounds are for use in a method for treatment or prevention of obesity.

In one embodiment, the compounds are for use in a method for treatment of obesity.

In one embodiment, the compounds are for use in a method for weight management. In one embodiment, the compounds are for use in a method for reduction of appetite. In one embodiment, the compounds are for use in a method for reduction of food intake.

EMBODIMENTS

1. A compound comprising a peptide and a substituent; wherein the amino acid sequence of the peptide is (SEQ ID NO.: 47)
$YX_2EGTX_6TSDYSX_{12}X_{13}LEX_{16}QAAX_{20}X_{21}FX_{23}X_{24}WLLX_{28}GX_{30}X_{31}X_{32}$
$X_{33}X_{34}X_{35}X_{36}X_{37}X_{38}X_{39}$ with an optional amide modification of the C-terminus, wherein $X_2$ is Aib or A
$X_6$ is F or V
$X_{12}$ is I or Y
$X_{13}$ is Y, A, L or I
$X_{16}$ is K or E
$X_{20}$ is Q, R, E, H
$X_{21}$ is A or E
$X_{23}$ is I or V
$X_{24}$ is E, Q or N
$X_{28}$ is A or R
$X_{30}$ is G or absent
$X_{31}$ is P or absent
$X_{32}$ is E, S or absent
$X_{33}$ is S, K or absent
$X_{34}$ is G or absent
$X_{35}$ is A or absent
$X_{36}$ is P or absent
$X_{37}$ is P or absent
$X_{38}$ is P or absent
$X_{39}$ is S or absent;

and wherein the substituent is attached to the peptide via Lysine (K) at position 16 or 33;

or a pharmaceutically acceptable salt hereof.

2. The compound according to embodiment 1, comprising a peptide and a substituent; wherein the amino acid sequence of the peptide is (SEQ ID NO.: 36)
$YX_2EGTX_6TSDYSX_{12}X_{13}LEX_{16}QAAX_{20}X_{21}FX_{23}X_{24}WLLX_{28}GGPX_{32}X_{33}$
$X_{34}X_{35}X_{36}X_{37}X_{38}X_{39}$ with an optional amide modification of the C-terminus, wherein $X_2$ is Aib or A
$X_6$ is F or V
$X_{12}$ is I or Y
$X_{13}$ is Y, A, L or I
$X_{16}$ is K or E
$X_{20}$ is Q, R, E, H
$X_{21}$ is A or E
$X_{23}$ is I or V
$X_{24}$ is E, Q or N
$X_{28}$ is A or R
$X_{32}$ is E, S or absent
$X_{33}$ is S, K or absent
$X_{34}$ is G or absent
$X_{35}$ is A or absent
$X_{36}$ is P or absent
$X_{37}$ is P or absent
$X_{38}$ is P or absent
$X_{39}$ is S or absent;

and wherein the substituent is attached to the peptide via Lysine (K) at position 16 or 33;

or a pharmaceutically acceptable salt hereof.

3. The compound according to embodiment 1, wherein $X_{36}$, $X_{37}$, $X_{38}$ and $X_{39}$ are absent.

4. The compound according to embodiment 1, wherein $X_{34}$, $X_{35}$, $X_{36}$, $X_{37}$, $X_{38}$ and $X_{39}$ are absent.

5. The compound according to embodiment 1, wherein $X_{32}$, $X_{33}$, $X_{34}$, $X_{35}$, $X_{36}$, $X_{37}$, $X_{38}$ and $X_{39}$ are absent.

6. The compound according to embodiment 1, wherein $X_{30}$, $X_{31}$, $X_{32}$, $X_{33}$, $X_{34}$, $X_{35}$, $X_{36}$, $X_{37}$, $X_{38}$ and $X_{39}$ are absent.

7. The compound according to any one of embodiments 1-6, wherein the peptide has the amide modification of the C-terminus.

8. The compound according to any of the previous embodiments 1, 2 or 7, wherein $X_{32}X_{33}X_{34}X_{35}$ is selected from the group consisting of SSGA (SEQ ID NO.: 40), ESGA (SEQ ID NO.: 41) and SKGA (SEQ ID NO.: 42).

9. The compound according to any of the previous embodiments 1, 2 or 7, wherein $X_{32}X_{33}X_{34}X_{36}$SSGA (SEQ ID NO.: 40).

10. The compound according to any of the previous embodiments 1, 2 or 7, wherein $X_{32}X_{33}X_{34}X_{36}$ is ESGA (SEQ ID NO.: 41).

11. The compound according to any of the previous embodiments 1, 2 or 7, wherein $X_{32}X_{33}X_{34}X_{36}$ is SKGA (SEQ ID NO.: 42).

12. The compound according to embodiment 1, wherein the amino acid sequence of the peptide is (SEQ ID NO.: 37)
YX$_2$EGTX$_6$TSDYSX$_{12}$X$_{13}$LEX$_{16}$QAAX$_{20}$X$_{21}$FX$_{23}$X$_{24}$WLLX$_{28}$GGPSSGAPPPS wherein
$X_2$ is Aib or A
$X_6$ is F or V
$X_{12}$ is I or Y
$X_{13}$ is Y, A, L or I
$X_{16}$ is K or E
$X_{20}$ is Q, R, E, H
$X_{21}$ is A or E
$X_{23}$ is I or V
$X_{24}$ is E, Q or N
$X_{28}$ is A or R.

13. The compound according to embodiment 1, wherein the amino acid sequence of the peptide is (SEQ ID NO.: 38)
YX$_2$EGTX$_6$TSDYSX$_{12}$X$_{13}$LEX$_{16}$QAAX$_{20}$X$_{21}$FX$_{23}$X$_{24}$WLLX$_{28}$GGPESGAPPPS wherein
$X_2$ is Aib or A
$X_6$ is F or V
$X_{12}$ is I or Y
$X_{13}$ is Y, A, L or I
$X_{16}$ is K or E
$X_{20}$ is Q, R, E, H
$X_{21}$ is A or E
$X_{23}$ is I or V
$X_{24}$ is E, Q or N
$X_{28}$ is A or R.

14. The compound according to embodiment 1, wherein the amino acid sequence of the peptide is (SEQ ID NO.: 39)
YX$_2$EGTX$_6$TSDYSX$_{12}$X$_{13}$LEX$_{16}$QAAX$_{20}$X$_{21}$FX$_{23}$X$_{24}$WLLX$_{28}$GGPSKGAPPPS wherein
$X_2$ is Aib or A
$X_6$ is F or V
$X_{12}$ is I or Y
$X_{13}$ is Y, A, L or I
$X_{16}$ is K or E
$X_{20}$ is Q, R, E, H
$X_{21}$ is A or E
$X_{23}$ is I or V
$X_{24}$ is E, Q or N
$X_{28}$ is A or R.

15. The compound according to any of the previous embodiments, wherein $X_{13}$LEX$_{16}$QAAX$_{20}$X$_{21}$FX$_{23}$X$_{24}$ is selected from the group consisting of: LLEKQAAREFIN (SEQ ID NO.: 43), LLEKQAAREFIE (SEQ ID NO.: 44), LLEKQAAQEFIE (SEQ ID NO.:45) and LLEEQAAREFIE (SEQ ID NO.: 46).

16. The compound according to embodiment 1, wherein the amino acid sequence of the peptide is any one of SEQ ID NO.: 1-27 or 33-35.

17. The compound according to embodiment 16, wherein the peptide has the amide modification of the C-terminus.

18. The compound according to any of the previous embodiments, wherein the compound activates the human GLP-1 and GIP receptors in vitro with an EC$_{50}$ of less than 20 pM when measured without HSA in CRE luciferase reporter assays as described in Example 2.

19. The compound according to any of the previous embodiments, wherein the compound has a half-life in minipigs of at least 35 hours.

20. The compound according to any of the previous embodiments, wherein the substituent is attached via 16Lys.

21. The compound according to any of the previous embodiments, wherein the substituent is attached via 33Lys.

22. The compound according to any of the previous embodiments, wherein the substituent comprises at least one protractor.

23. The compound according to embodiment 22, wherein the protractor is a fatty acid group.

24. The compound according to embodiment 23, wherein the protractor is a diacid defined by Chem. 1: HOOC—(CH$_2$)$_n$—CO— wherein n is an integer in the range of 8-20, such as n=14, 16 or 18.

25. The compound according to embodiment 23, wherein the protractor is a diacid defined by Chem. 1: HOOC—(CH$_2$)$_n$—CO— wherein n is an integer in the range of 8-20, such as n=16 or 18.

26. The compound according to any of the previous embodiments, wherein the substituent comprises at least one linker element.

27. The compound according to embodiment 26, wherein the substituent comprises at most three linker elements.

28. The compound according to embodiment 27, wherein the substituent comprises at most three linker elements referred to as -Z1-Z2-Z3-, where -Z1- is connected with the protractor and -Z3- is connected to the peptide.

29. The compound according to any of the previous embodiments, wherein the substituent is :

Prot-Z1-Z2-Z3- wherein

Prot is a C16-C20 diacid

Z1 is γGlu or a bond

Z2 is εLys, γGlu or Ado and

Z3 is εLys or Ado.

30. The compound according to embodiment 29, wherein -Z1- is -γGlu-.

31. The compound according to embodiments 29 or 30, wherein -Z2-Z3- and is -Ado-Ado-.

32. The compound according to embodiments 29, 30 or 31, wherein -Z2-Z3- and is -εLys-εLys-.

33. The compound according to any of the embodiments 1-17, wherein the substituent is selected from the group consisting of:
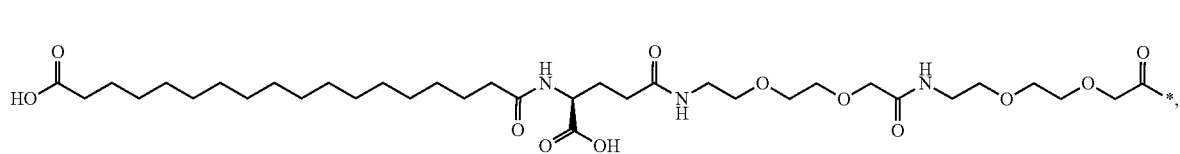
A
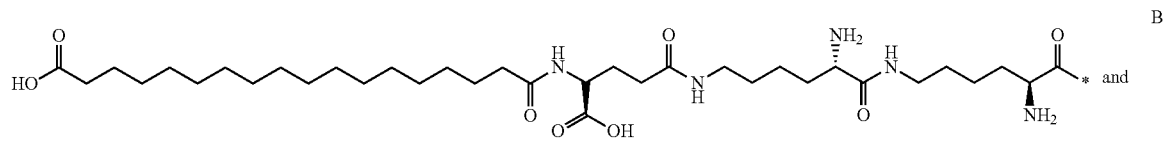
B and
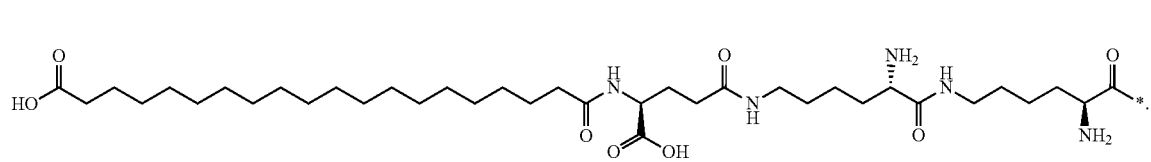
C.
34. The compound according to any of the embodiments 1-17, wherein the substituent is selected from the group consisting of:
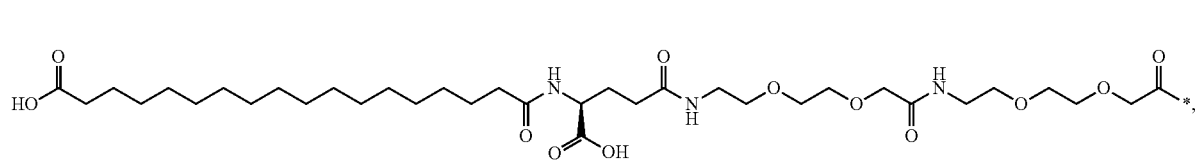
A
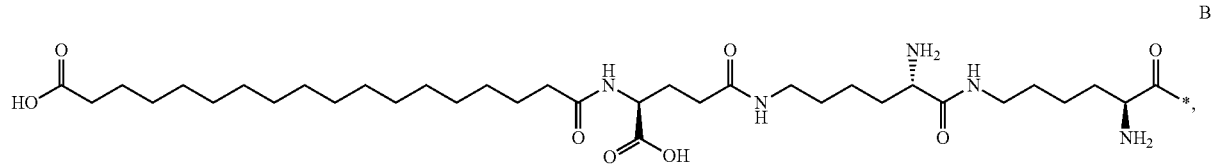
B
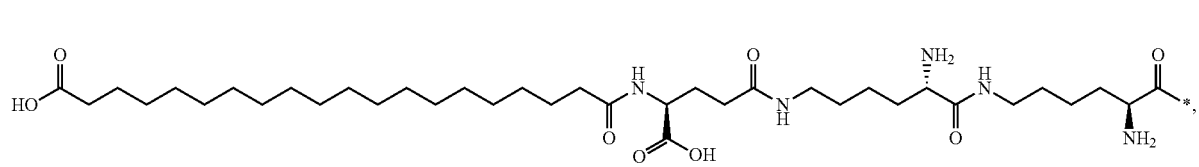
C
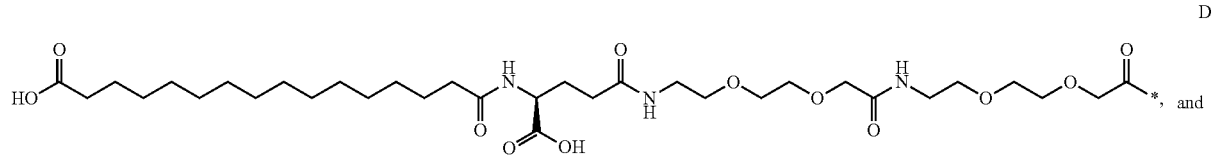
D and
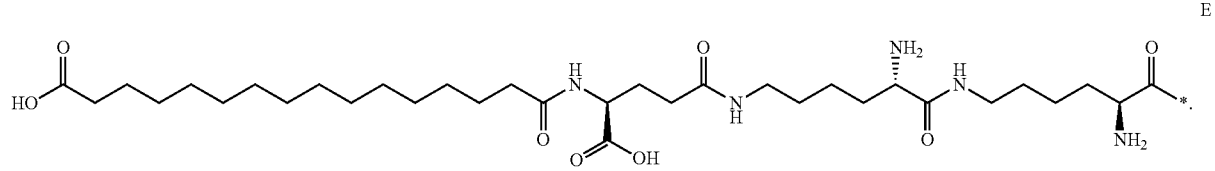
E 35. The compound according to any of the previous embodiments 1-17, wherein the substituent is attached to the peptide via the epsilon-amino group of a Lysine (K).
36. The compound according to embodiment 1, wherein the compound is selected from the group consisting of:
---
Compound No. 1
SEQ ID NO: 1
Substituent: C
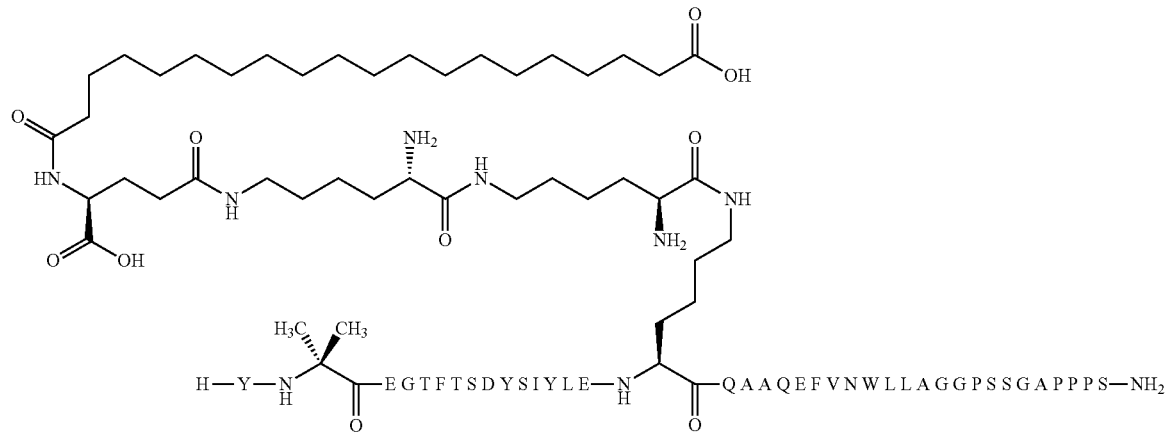
Compound No. 2
SEQ ID NO: 2
Substituent: C
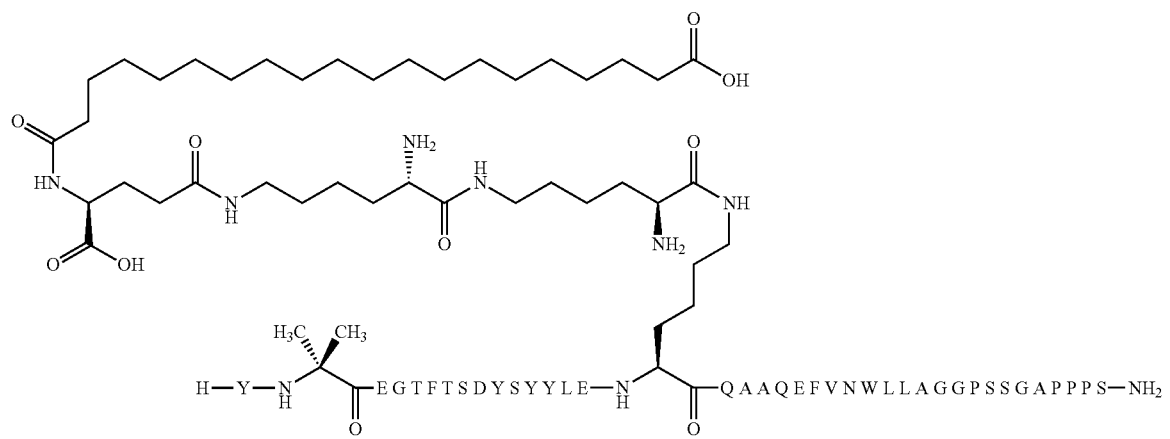
Compound No. 3
SEQ ID NO: 2
Substituent: B
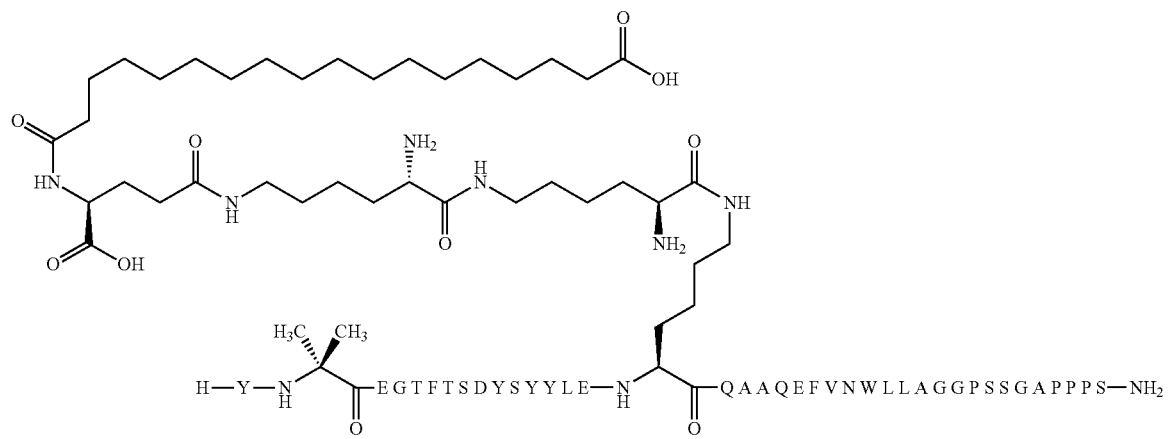

Compound No. 4
SEQ ID NO: 3
Substituent: B
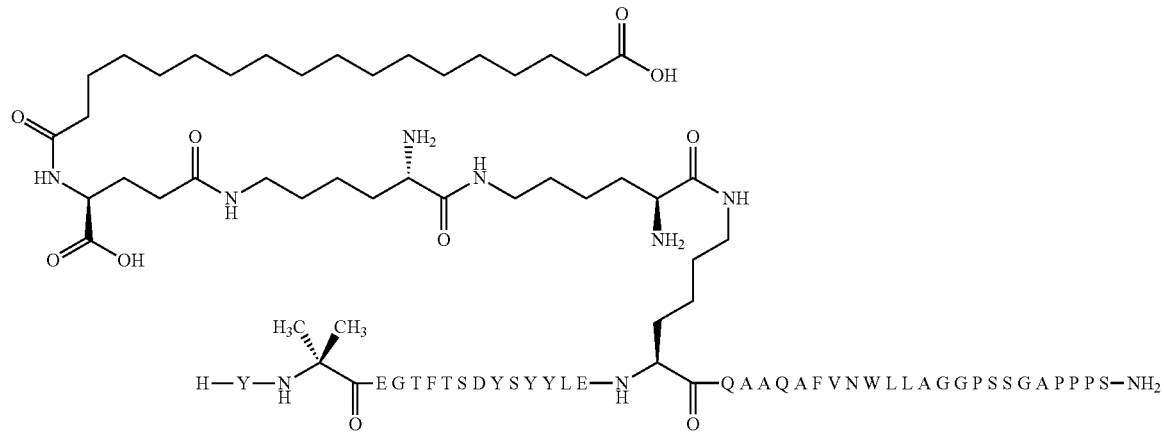
Compound No. 5
SEQ ID NO: 3
Substituent: B
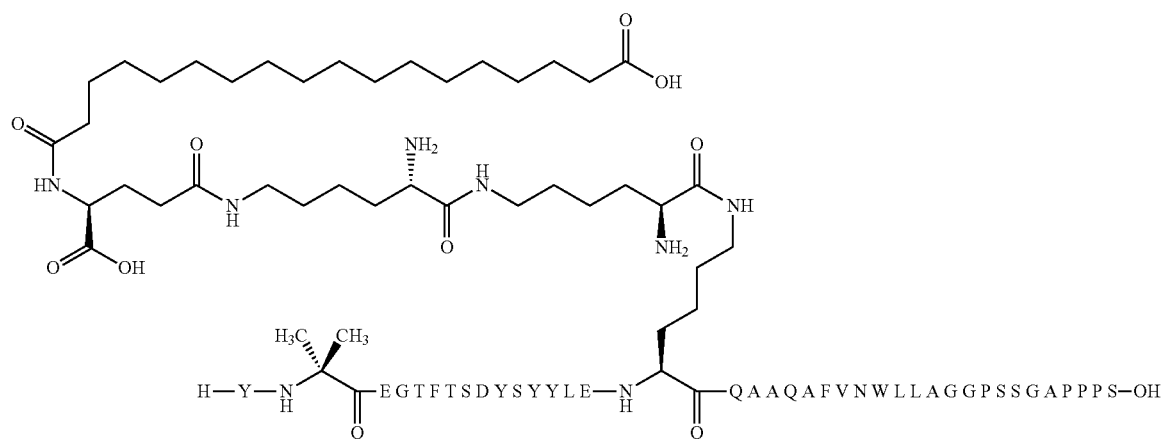
Compound No. 6
SEQ ID NO: 4
Substituent: B
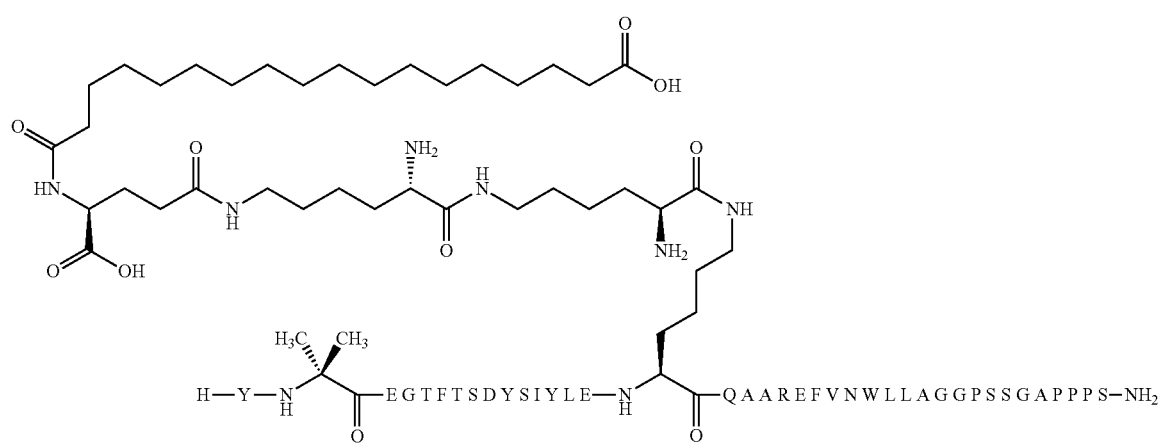

Compound No. 7
SEQ ID NO: 4
Substituent: A
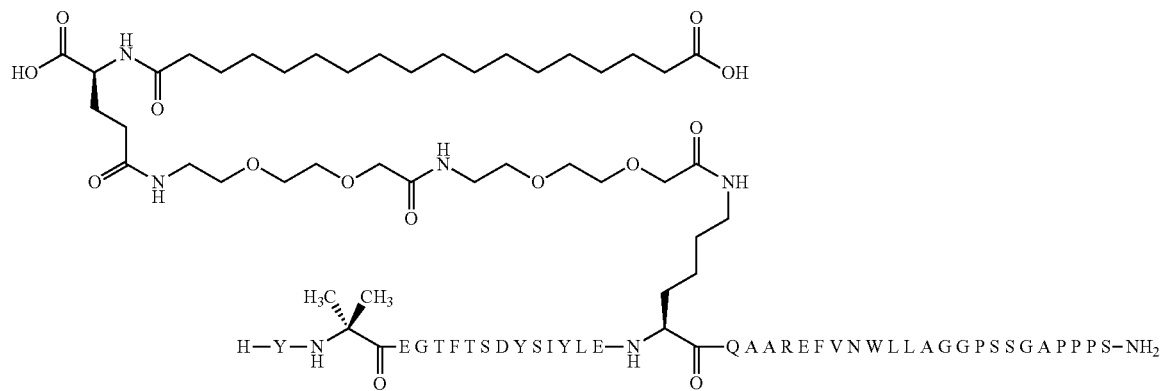
Compound No. 8
SEQ ID NO: 5
Substituent: B
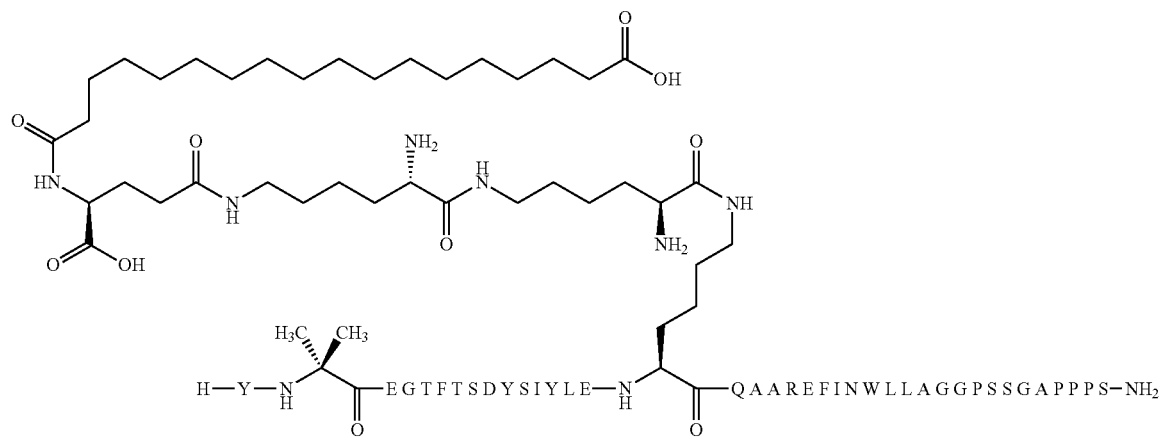
Compound No. 9
SEQ ID NO: 6
Substituent: B
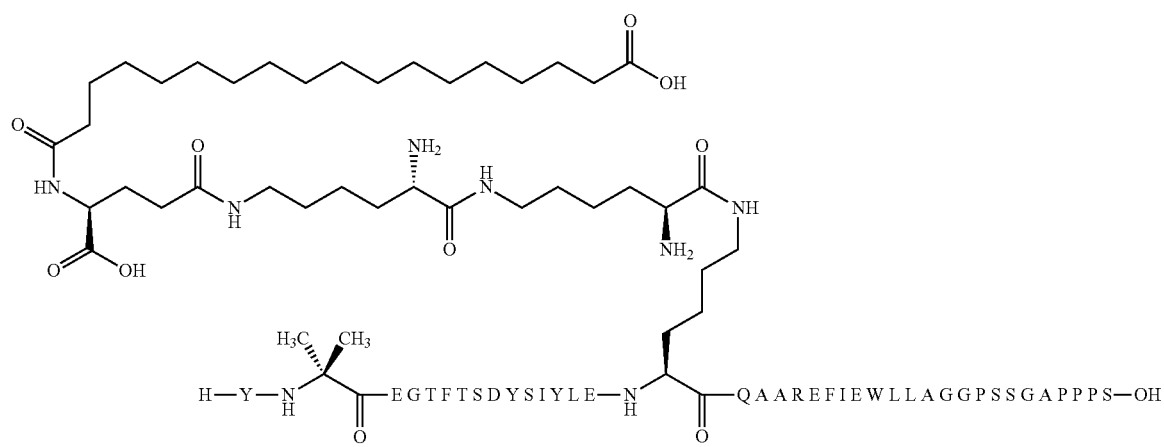

Compound No. 10
SEQ ID NO: 6
Substituent: A
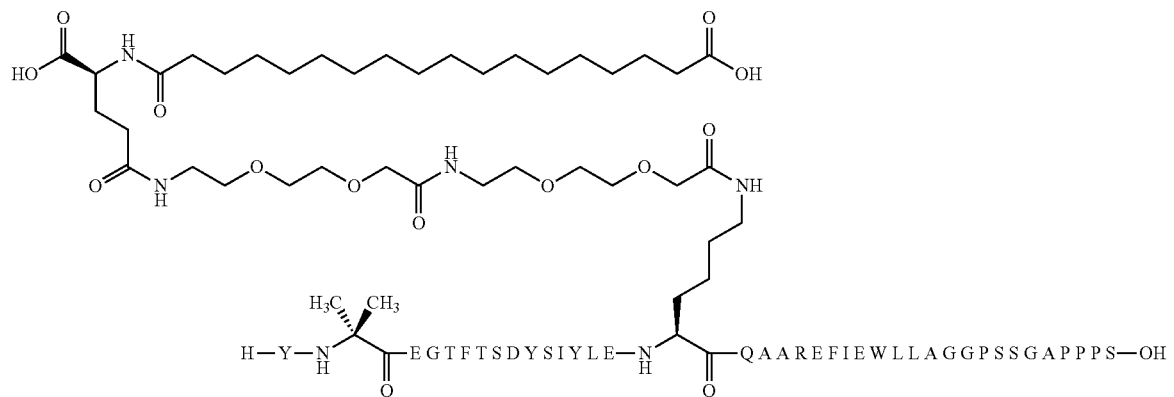
Compound No. 11
SEQ ID NO: 5
Substituent: B
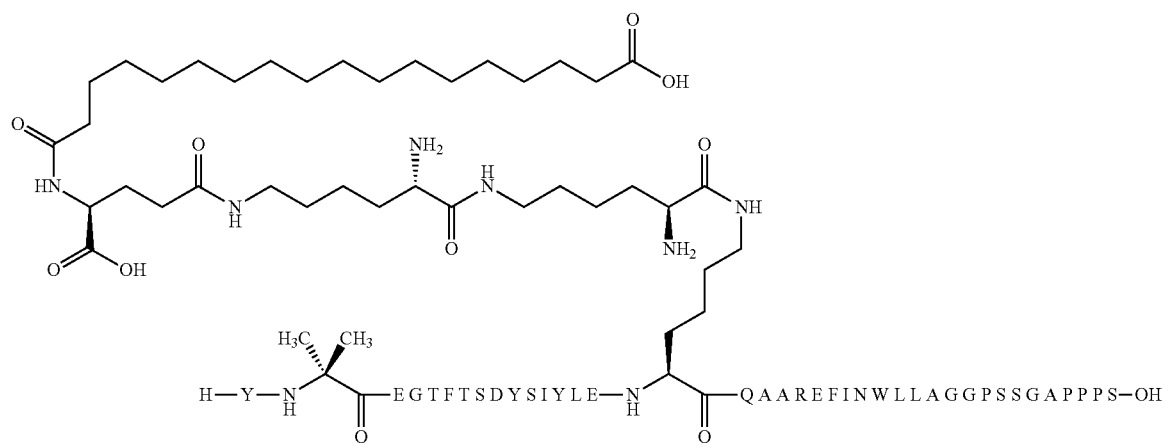
Compound No. 12
SEQ ID NO: 7
Substituent: B
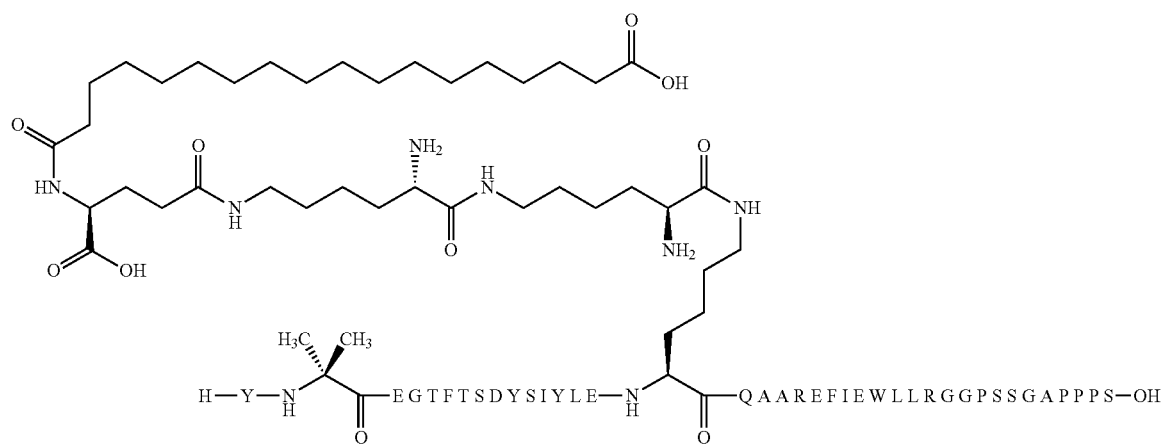

Compound No. 13
SEQ ID NO: 8
Substituent: B
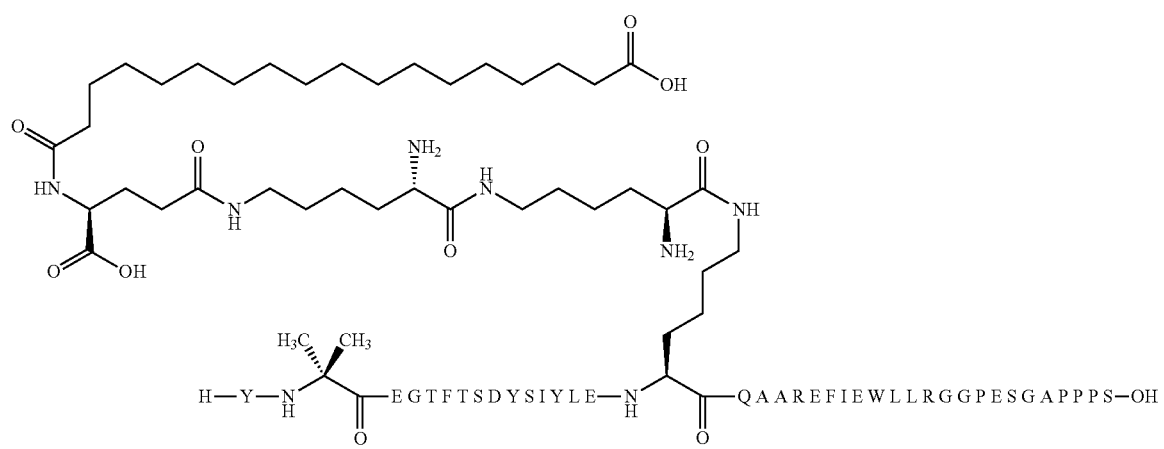
Compound No. 14
SEQ ID NO: 9
Substituent: B
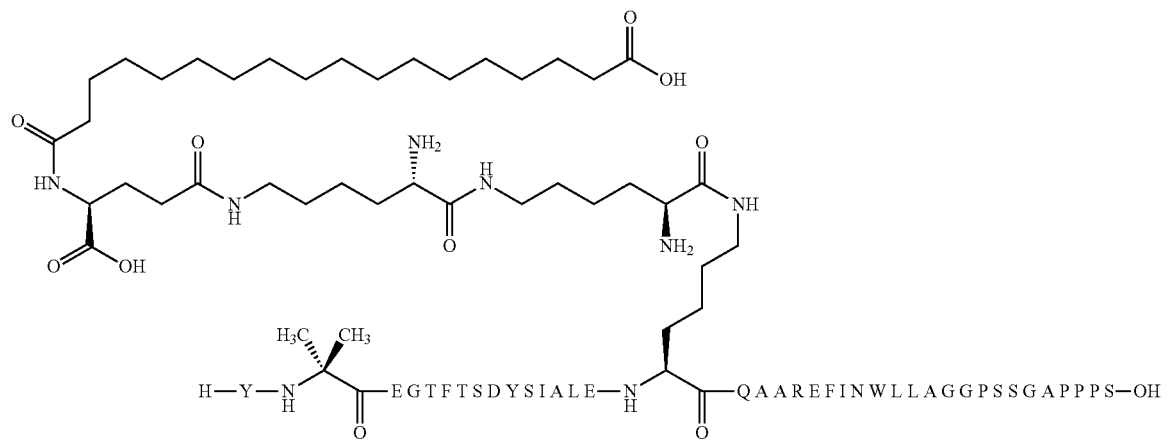
Compound No. 15
SEQ ID NO: 10
Substituent: B
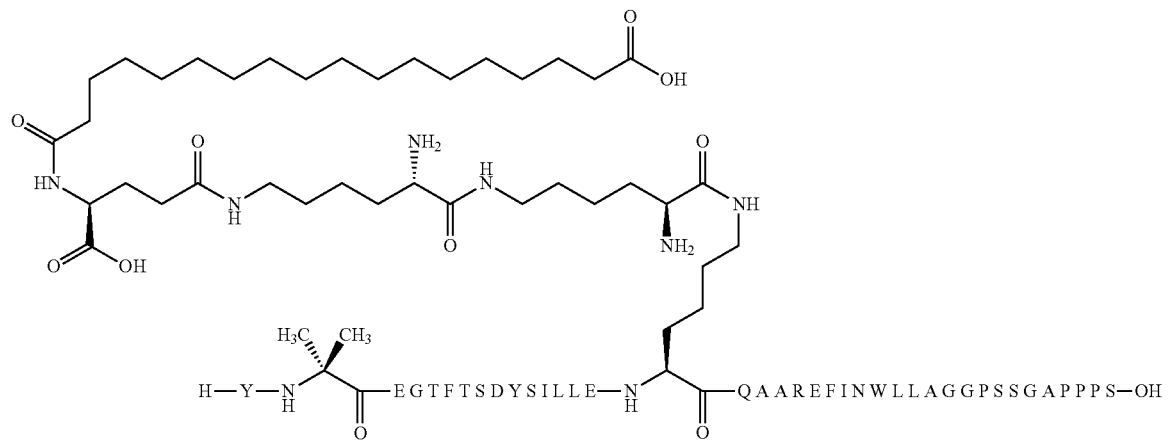

Compound No. 16
SEQ ID NO: 5
Substituent: C
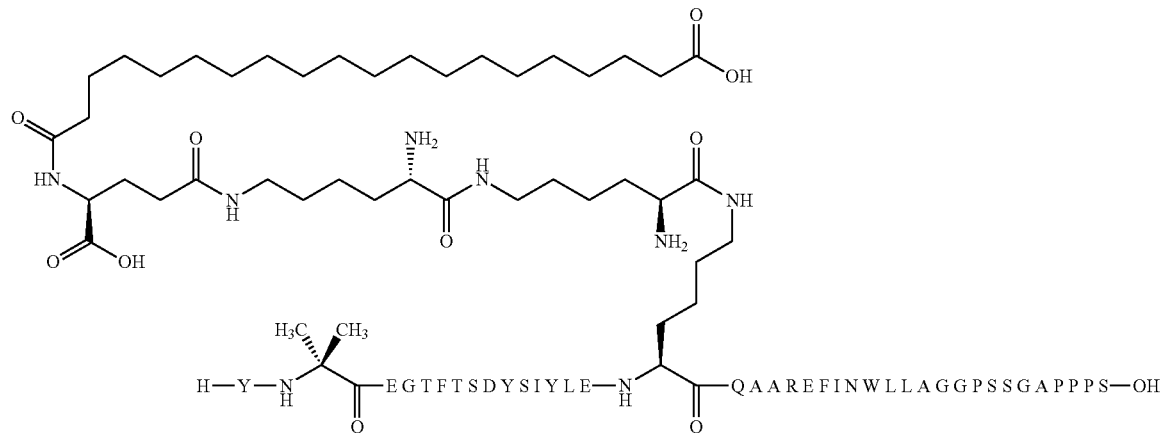
Compound No. 17
SEQ ID NO: 11
Substituent: B
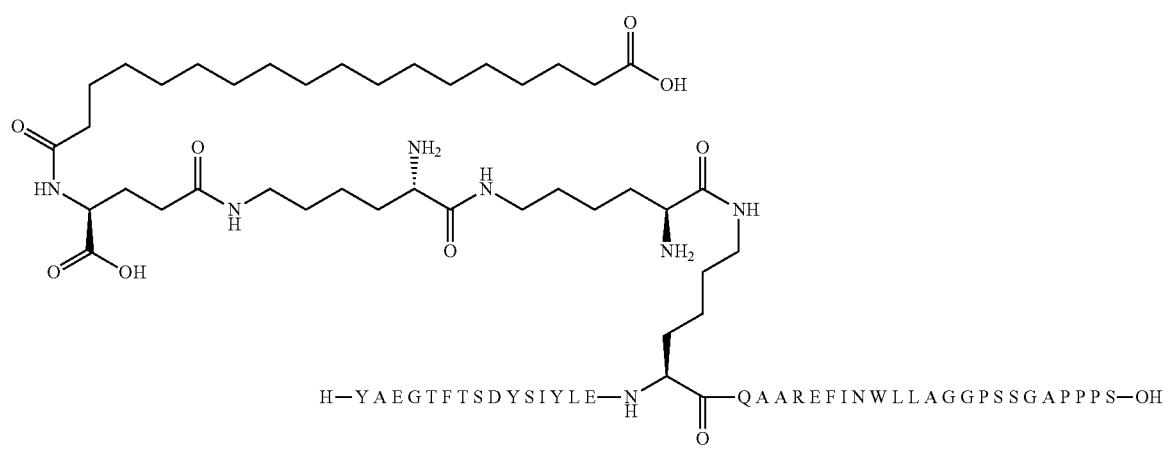
Compound No. 18
SEQ ID NO: 12
Substituent: B
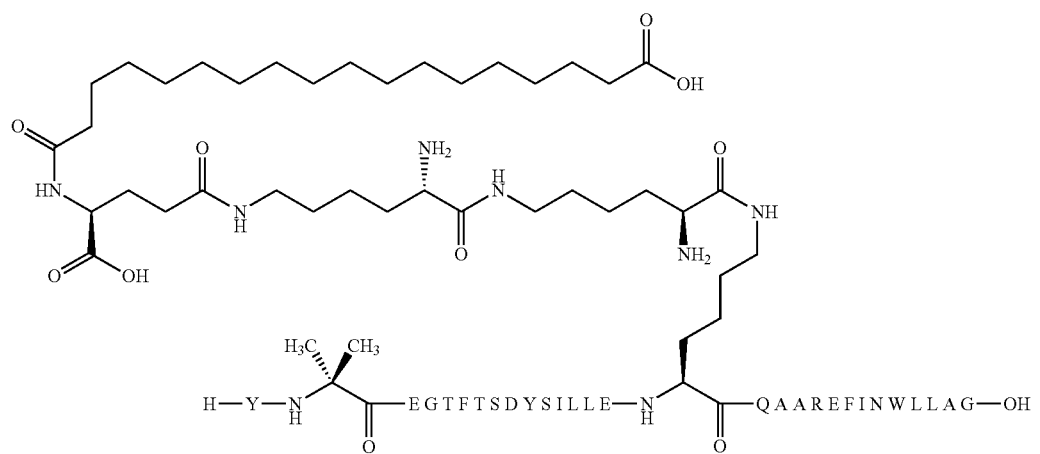

Compound No. 19
SEQ ID NO: 13
Substituent: B
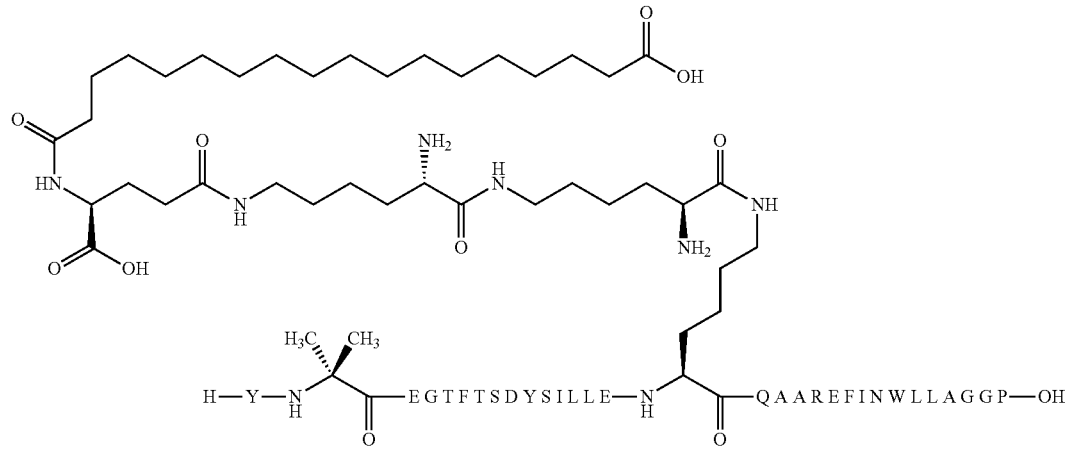
Compound No. 20
SEQ ID NO: 14
Substituent: B
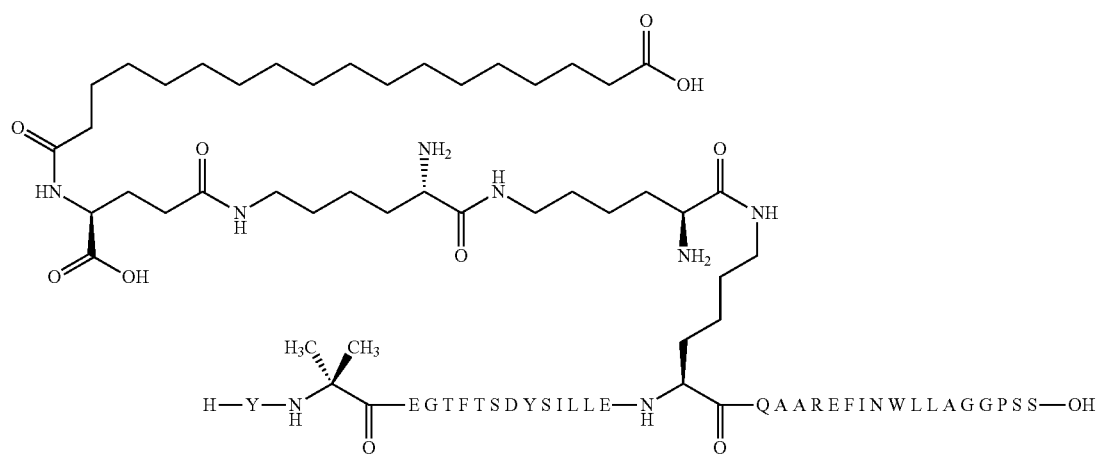
Compound No. 21
SEQ ID NO: 15
Substituent: B
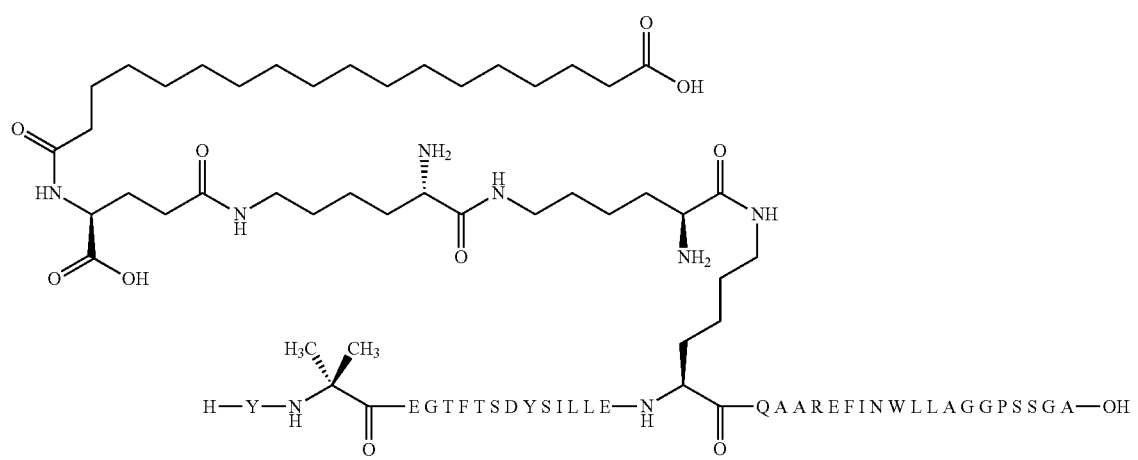

Compound No. 22
SEQ ID NO: 16
Substituent: B
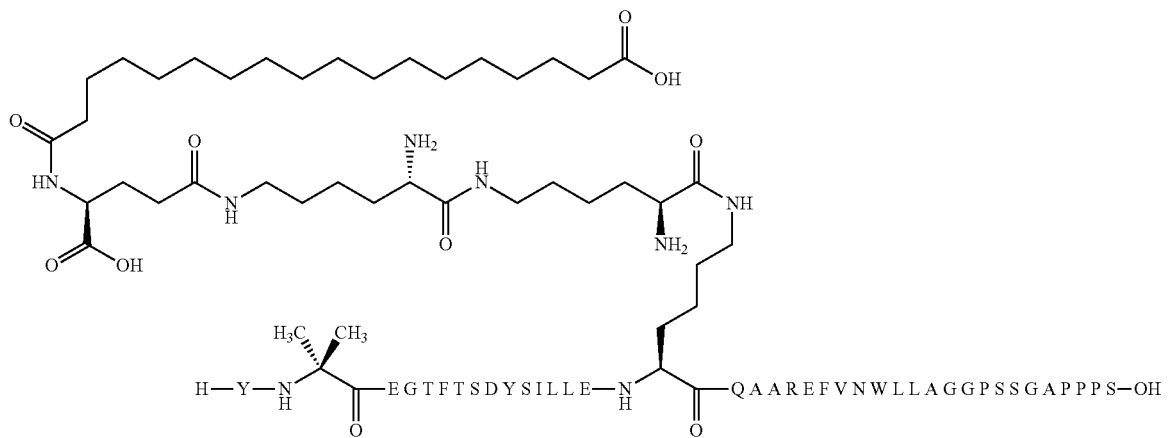
Compound No. 23
SEQ ID NO: 17
Substituent: B
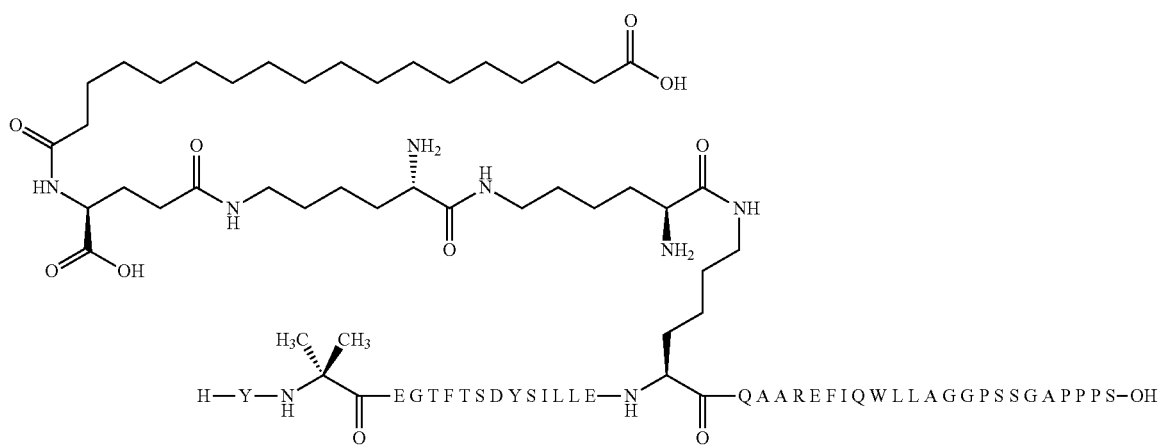
Compound No. 24
SEQ ID NO: 18
Substituent: B
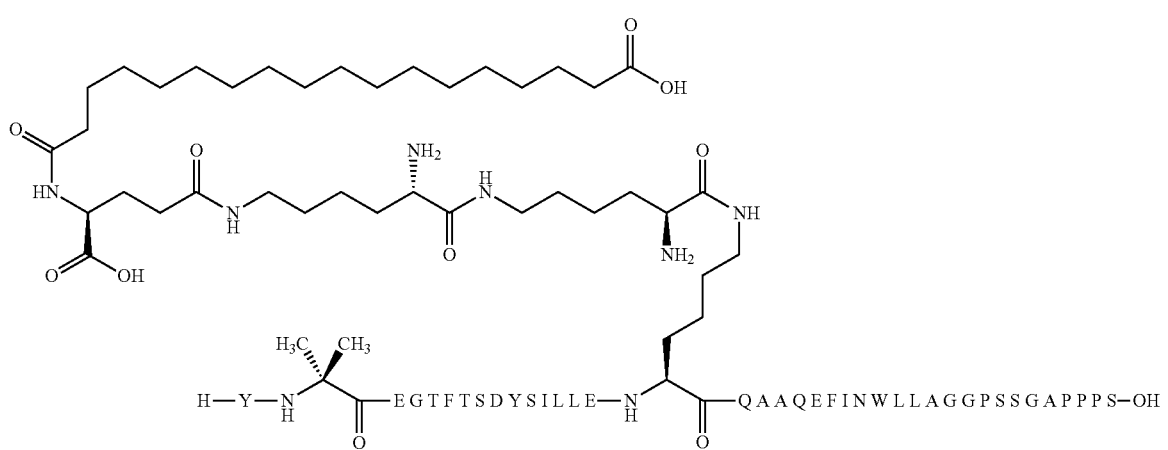

Compound No. 25
SEQ ID NO: 19
Substituent: B
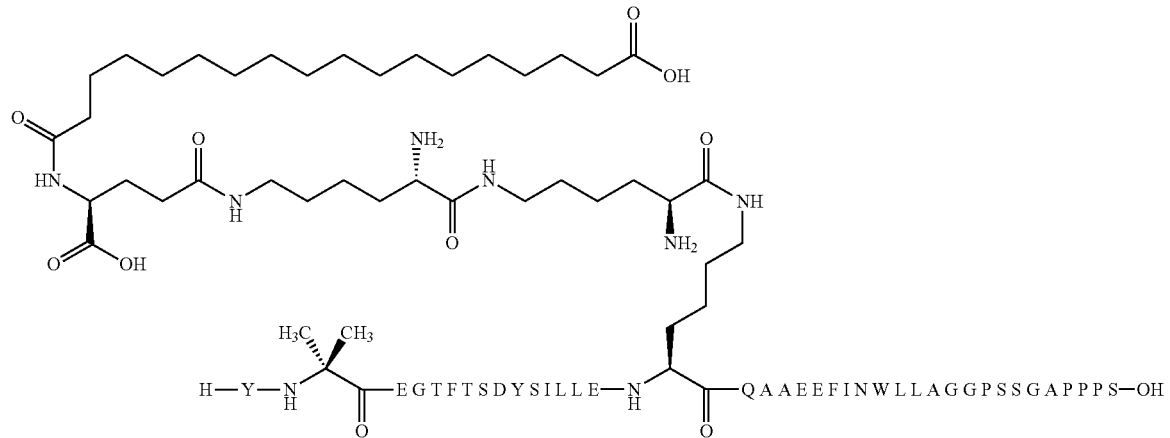
Compound No. 26
SEQ ID NO: 20
Substituent: B
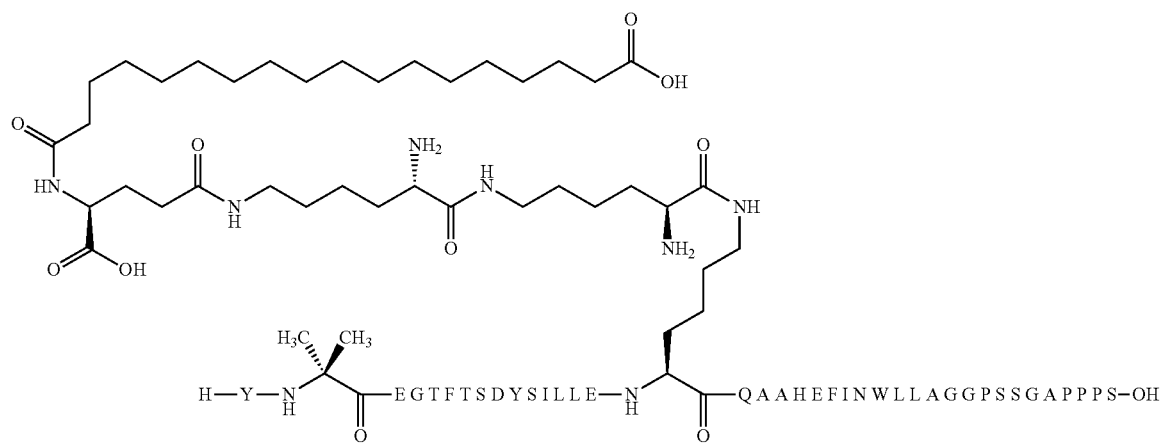
Compound No. 27
SEQ ID NO: 21
Substituent: B
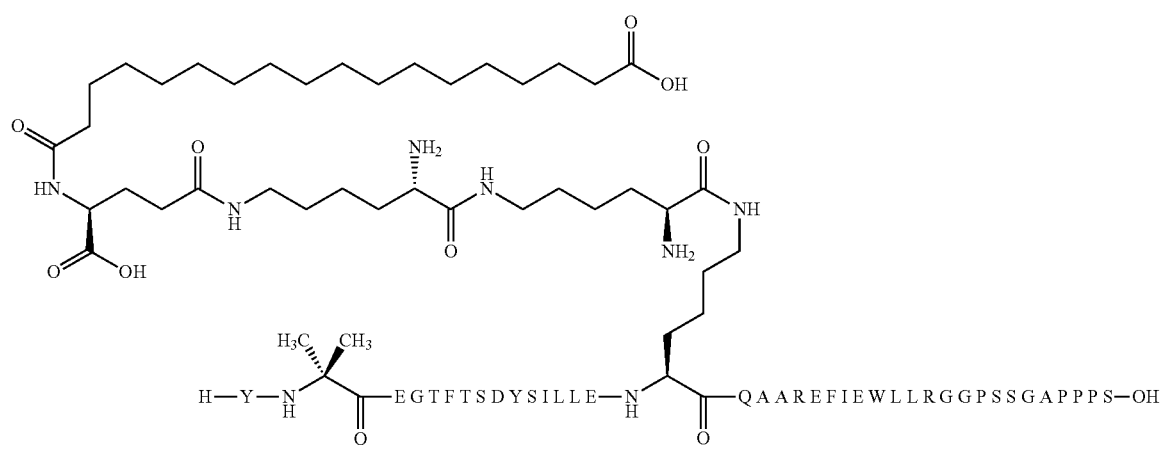

Compound No. 28
SEQ ID NO: 22
Substituent: B
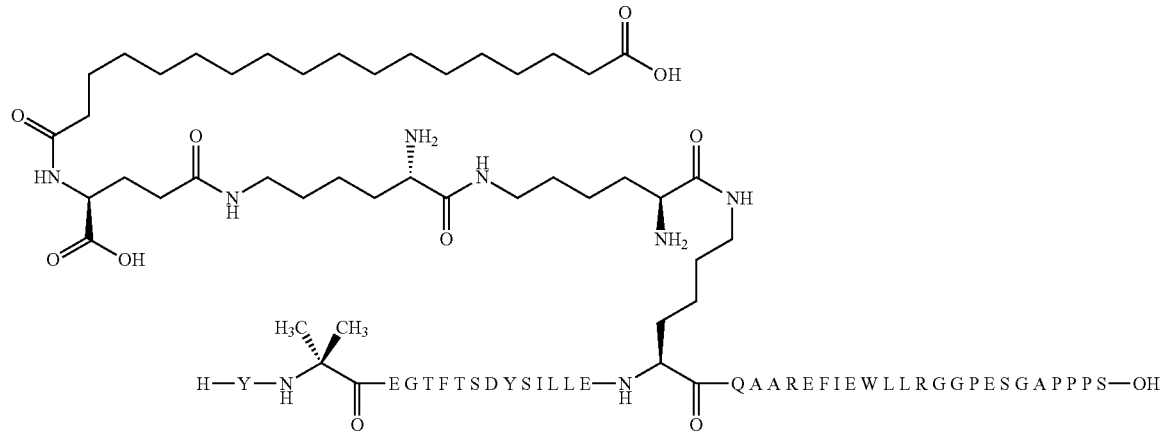
Compound No. 29
SEQ ID NO: 23
Substituent: B
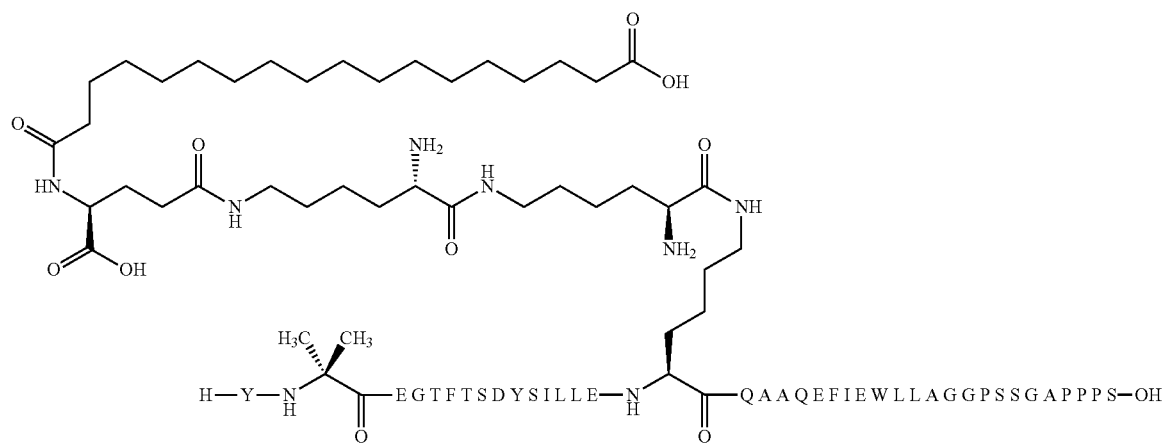
Compound No. 30
SEQ ID NO: 24
Substituent: B
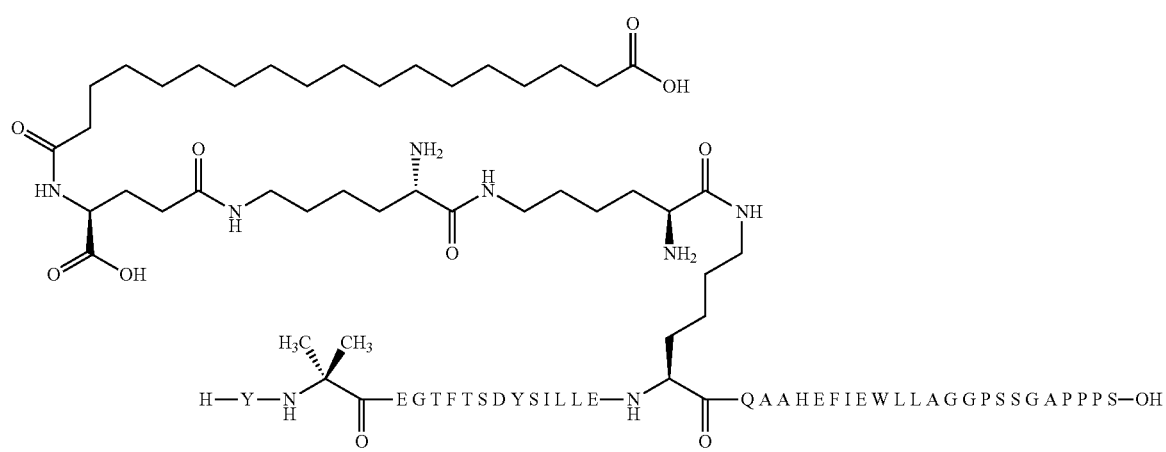

Compound No. 31
SEQ ID NO: 25
Substituent: B
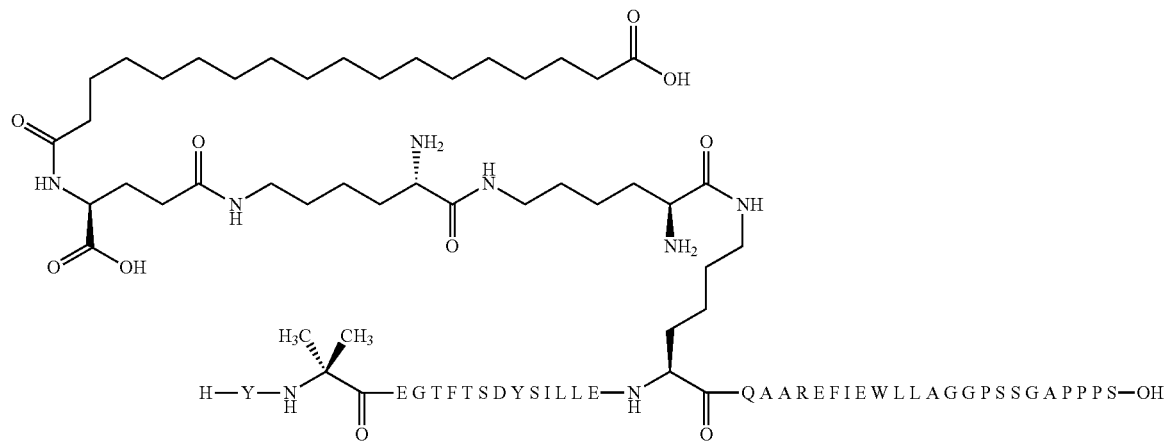
Compound No. 32
SEQ ID NO: 25
Substituent: A
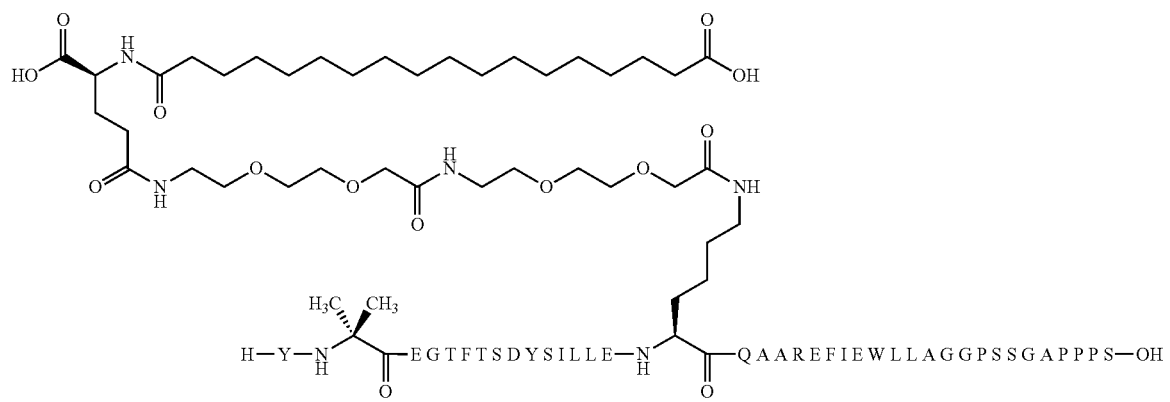
Compound No. 33
SEQ ID NO: 26
Substituent: B
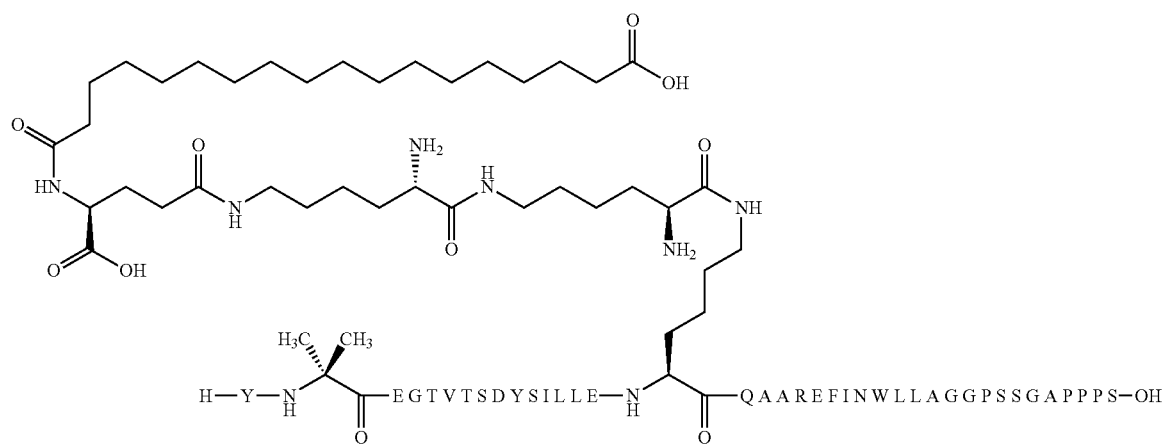

Compound No. 34
SEQ ID NO: 27
Substituent: B
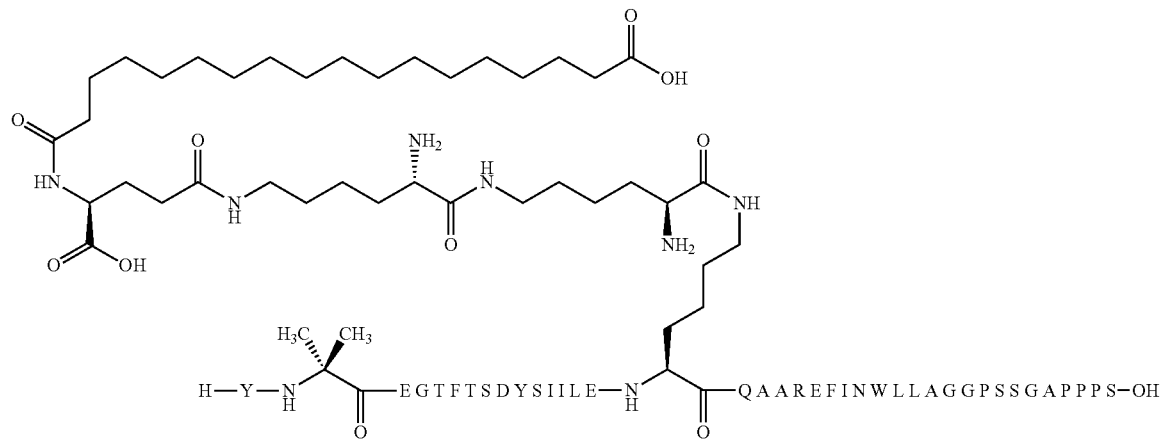
Compound No. 35
SEQ ID NO: 10
Substituent: A
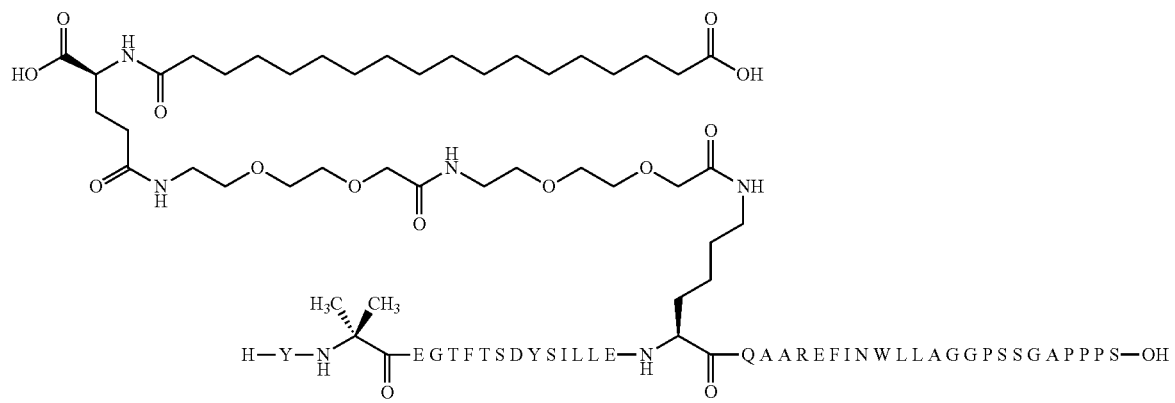
Compound No. 36
SEQ ID NO: 27
Substituent: A
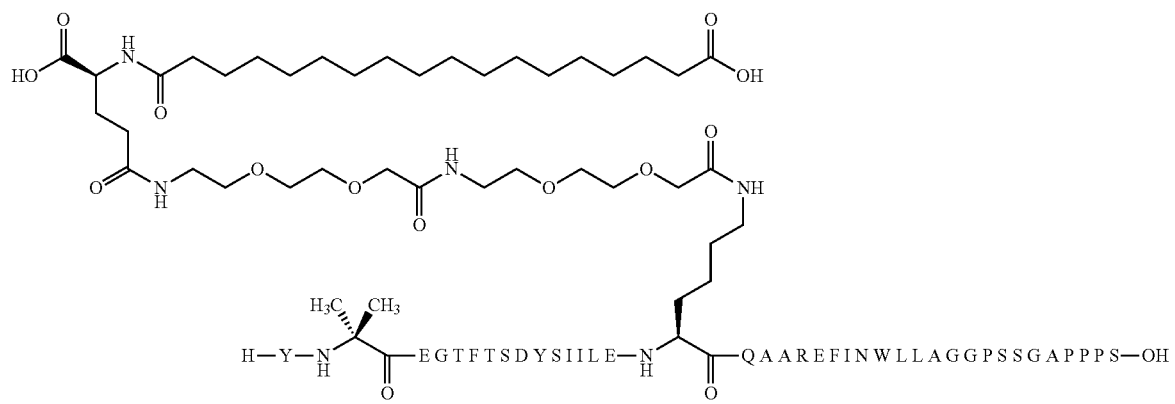

Compound No. 42
SEQ ID NO: 33
Substituent: B
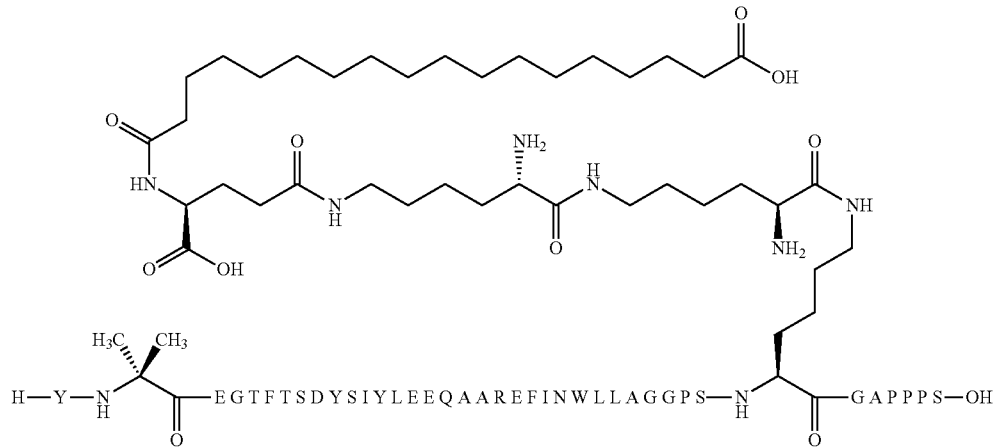
Compound No. 43
SEQ ID NO: 34
Substituent: B
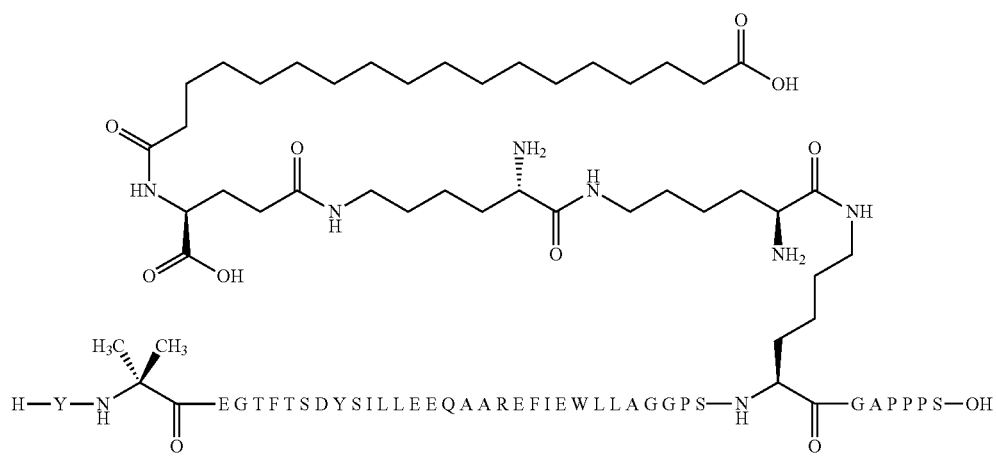
Compound No. 44
SEQ ID NO: 35
Substituent: B
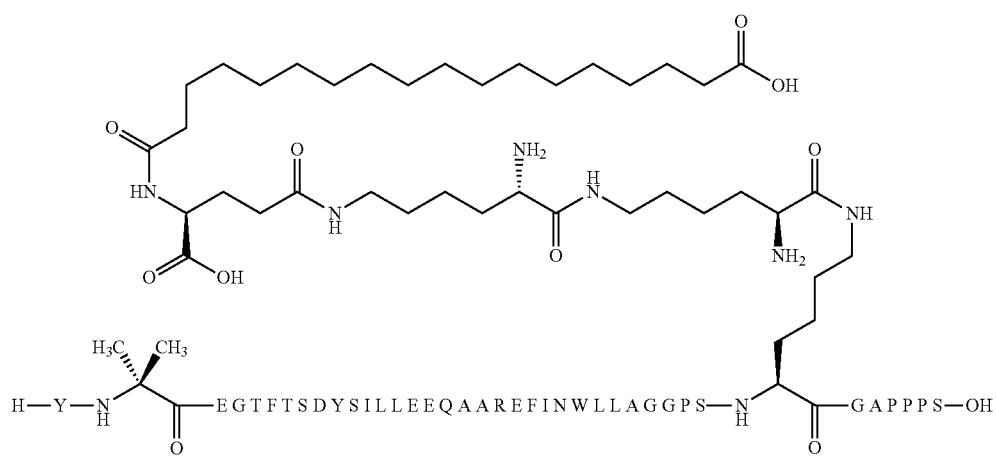

Compound No. 45
SEQ ID NO: 34
Substituent: A
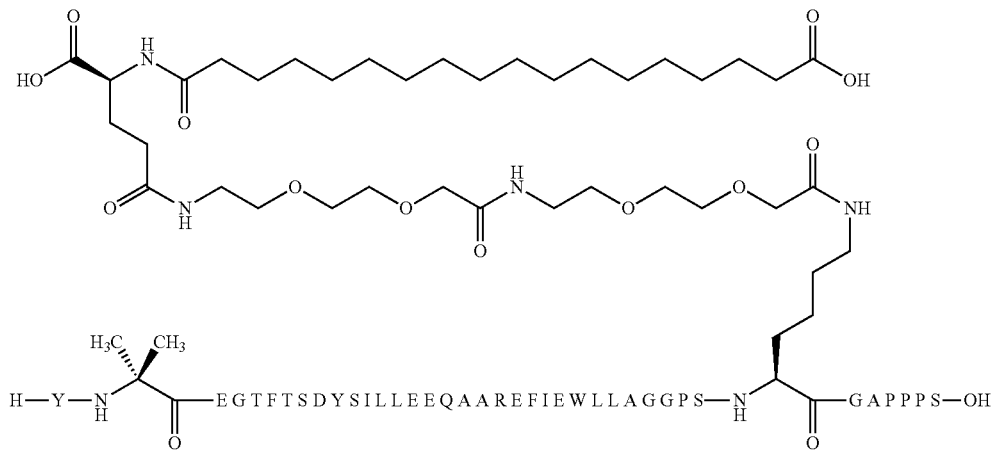
Compound No. 46
SEQ ID NO: 34
Substituent: E
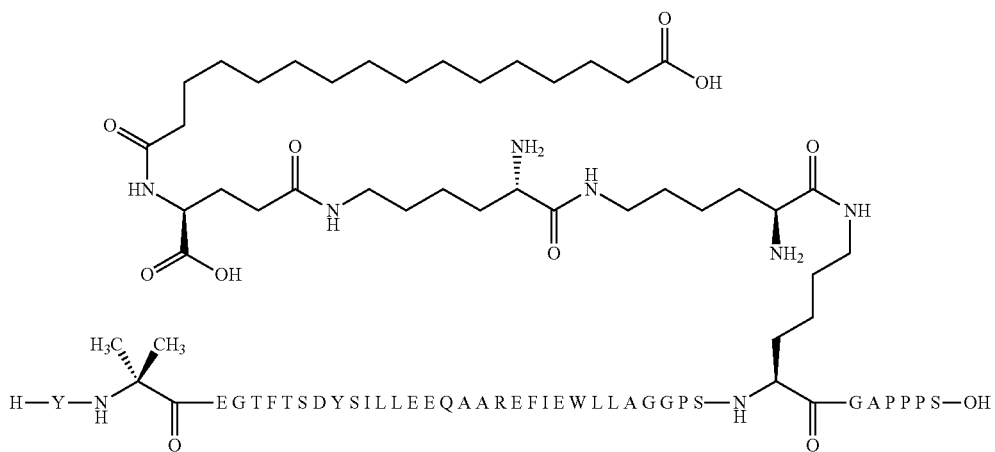
Compound No. 47
SEQ ID NO: 34
Substituent: D
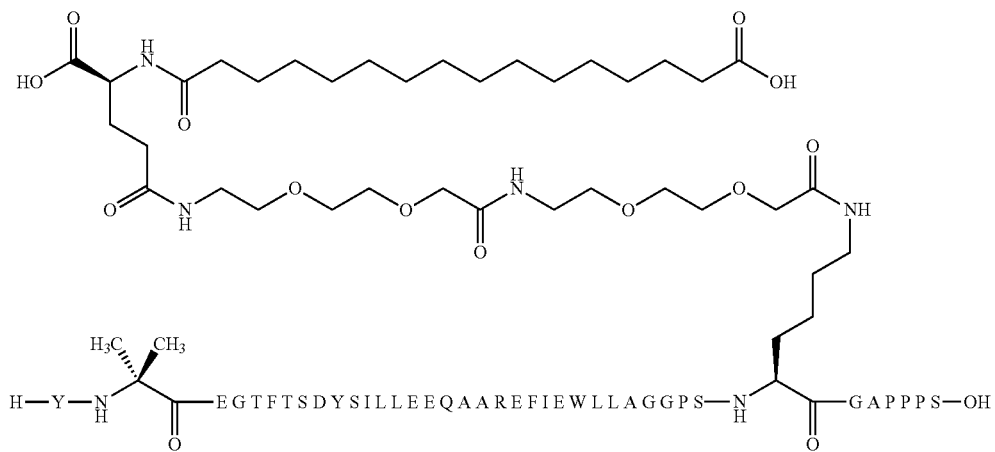

37. The compound according to embodiment 1, wherein the compound is selected from the group consisting of:
---
Compound No. 15
SEQ ID NO: 10
Substituent: B
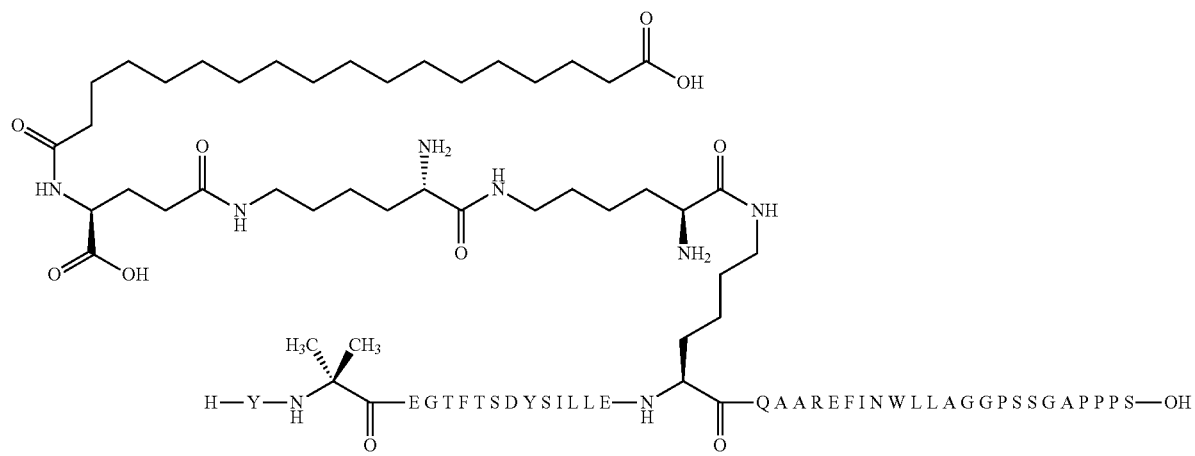
Compound No. 31
SEQ ID NO: 25
Substituent: B
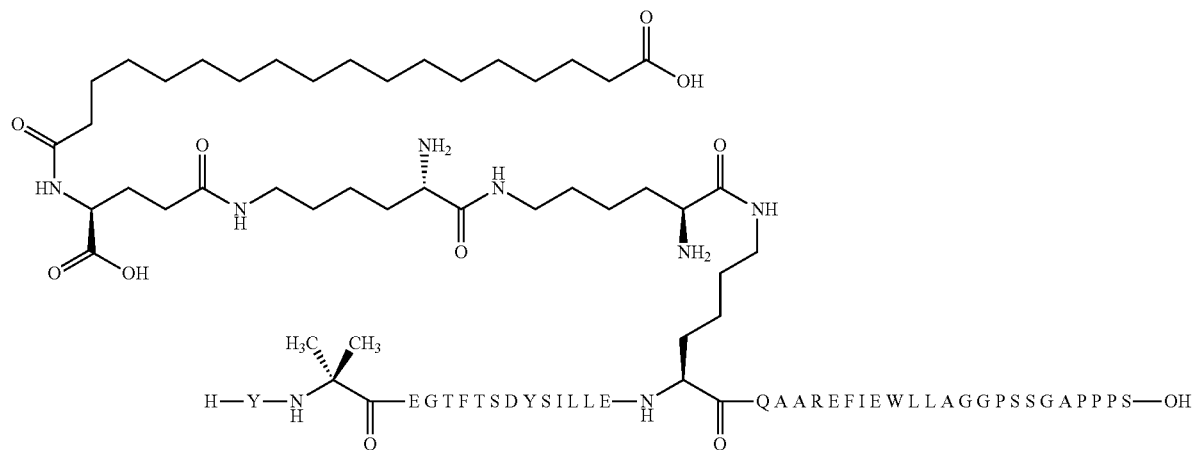
Compound No. 32
SEQ ID NO: 25
Substituent: A
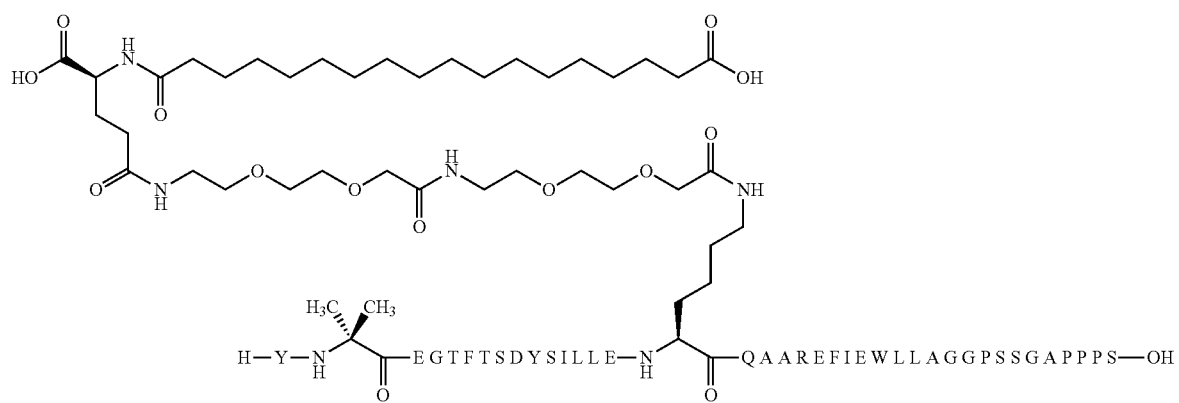

Compound No. 28
SEQ ID NO: 22
Substituent: B
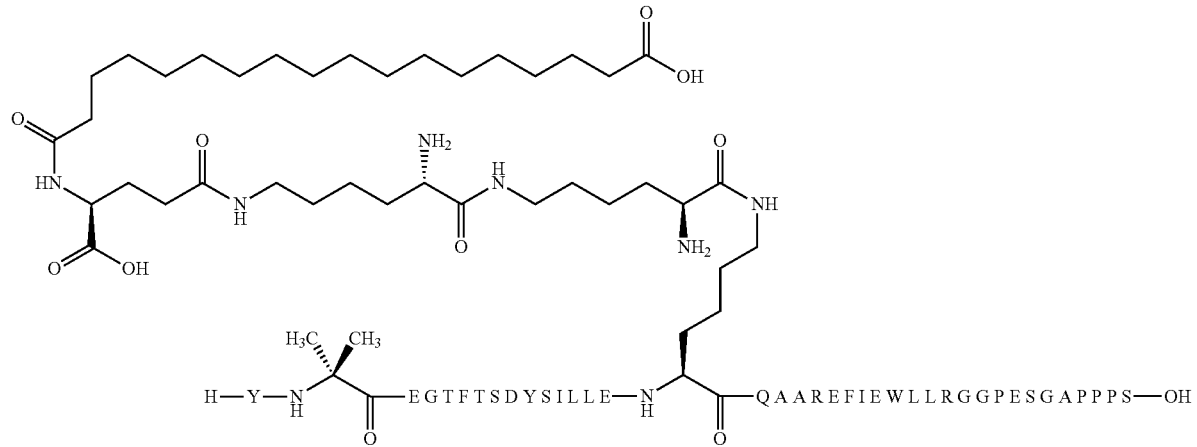
Compound No. 29
SEQ ID NO: 23
Substituent: B
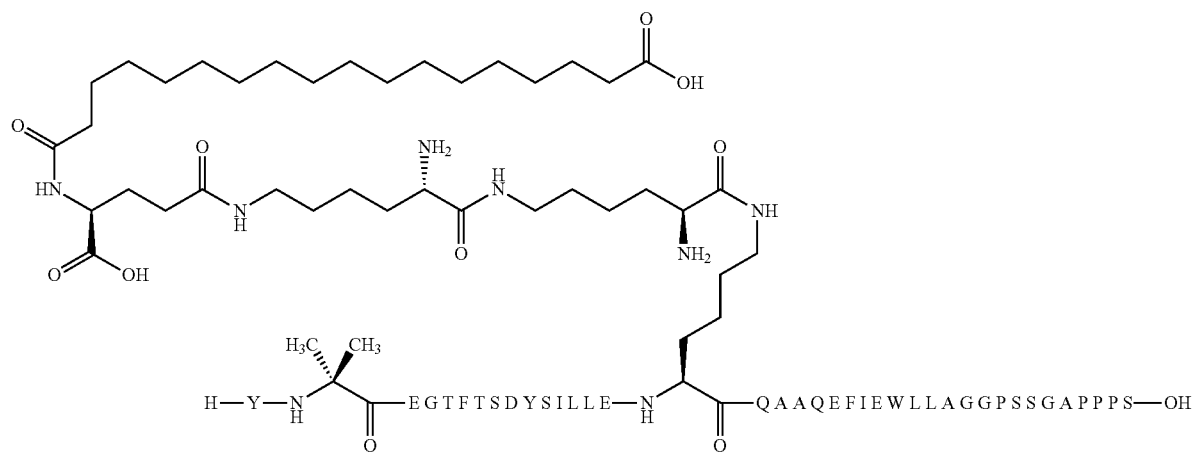
Compound No. 43
SEQ ID NO: 34
Substituent: B
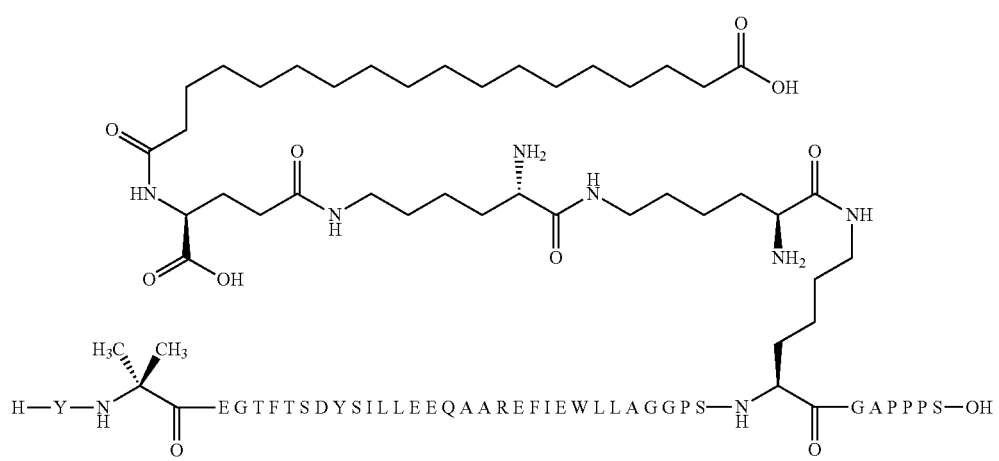

Compound No. 46
SEQ ID NO: 34
Substituent: E
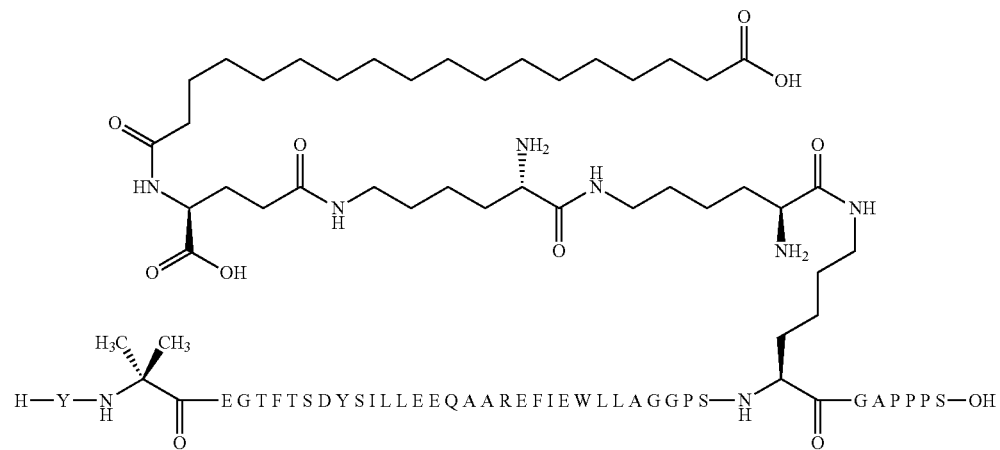
Compound No. 47
SEQ ID NO: 34
Substituent: D
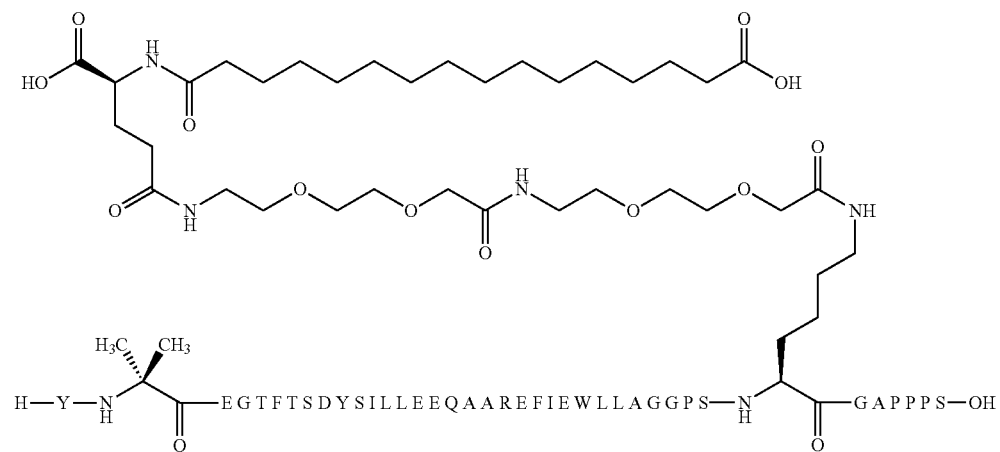

38. The compound according to embodiment 1, wherein the compound is selected from the group consisting of:
Compound No. 15
SEQ ID NO: 10
Substituent: B
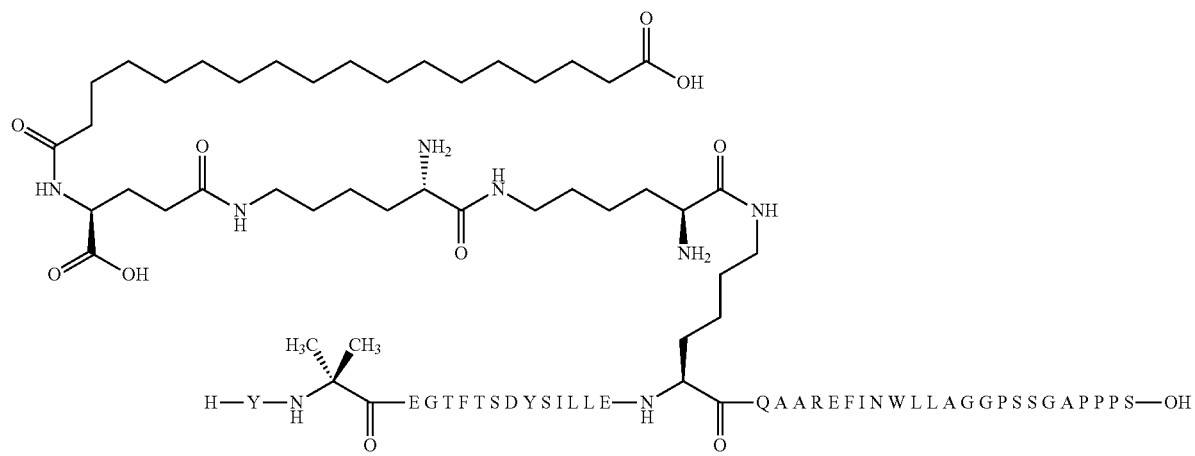
Compound No. 31
SEQ ID NO: 25
Substituent: B
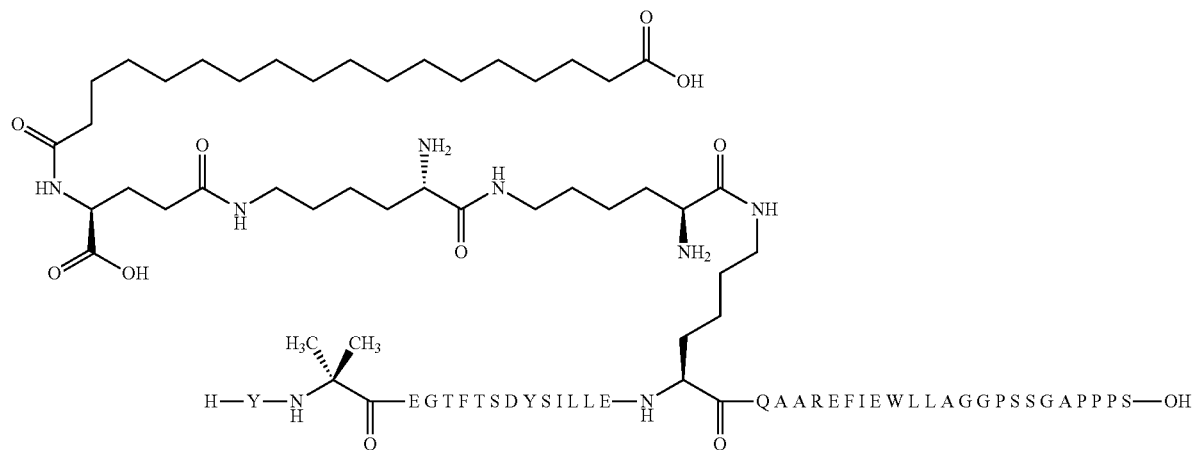
Compound No. 32
SEQ ID NO: 25
Substituent: A
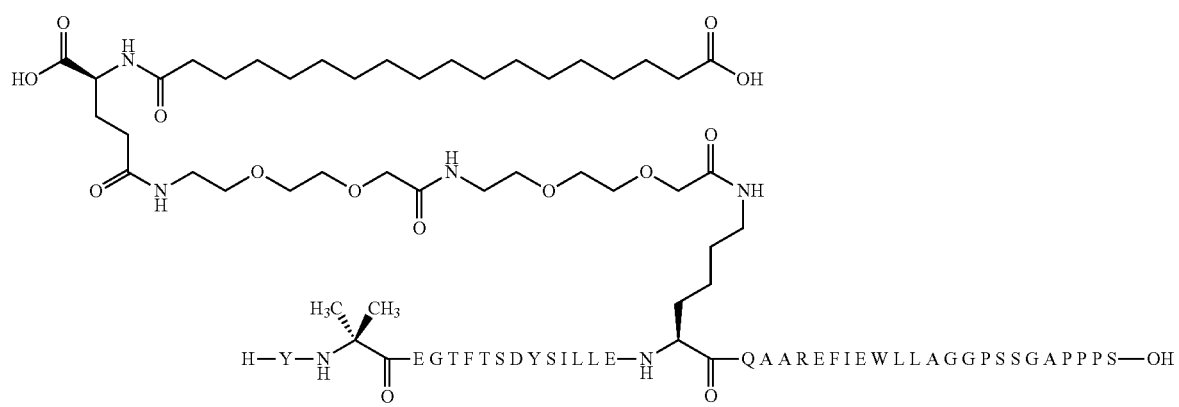

-continued
Compound No. 28
SEQ ID NO: 22
Substituent: B
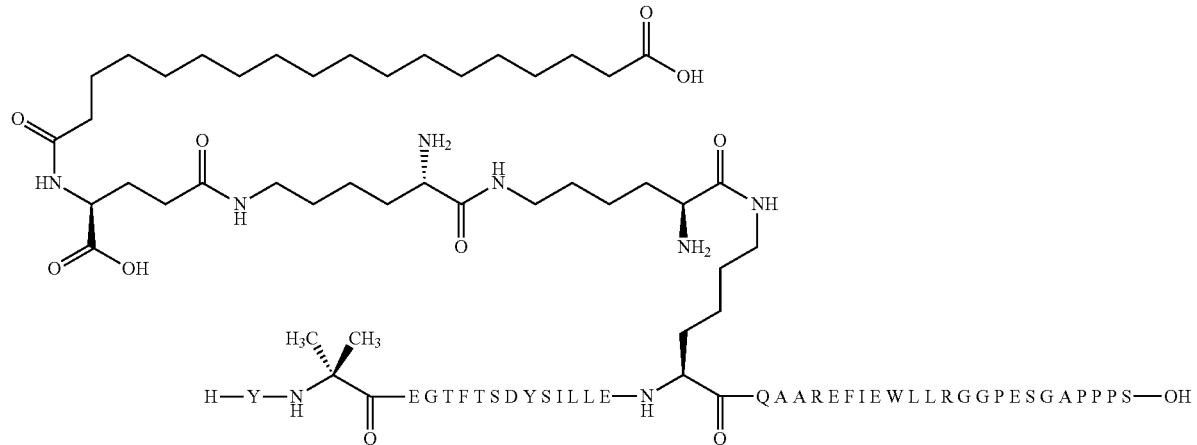
Compound No. 29
SEQ ID NO: 23
Substituent: B
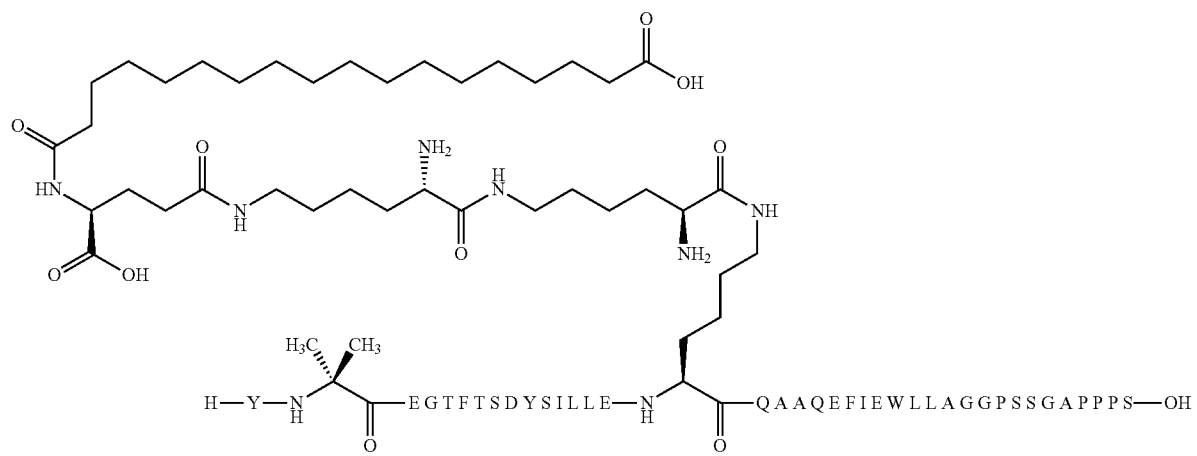
Compound No. 46
SEQ ID NO: 34
Substituent: E
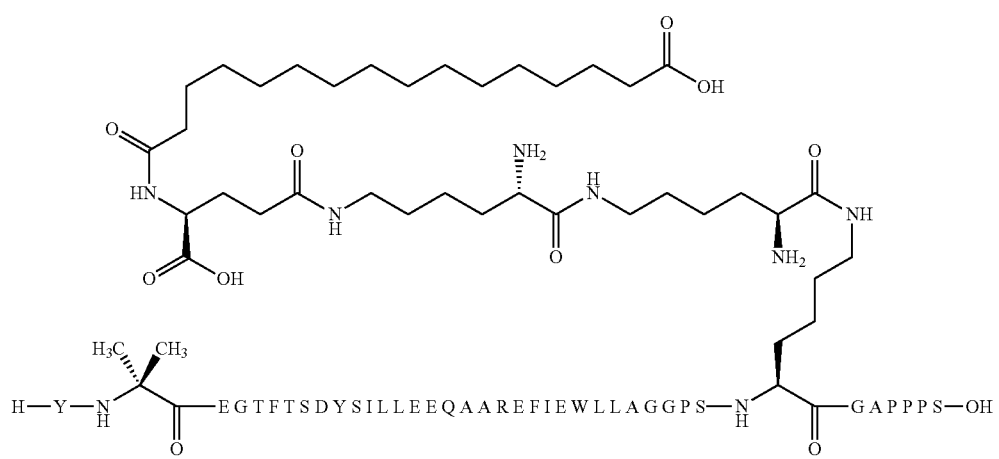

Compound No. 47
SEQ ID NO: 34
Substituent: D
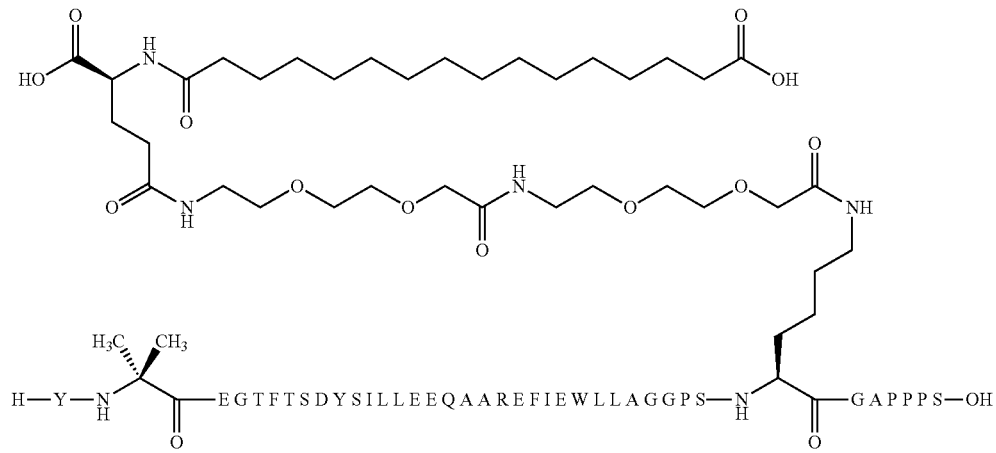
39. The compound according to embodiment 1, wherein the compound is:
Compound No. 43
SEQ ID NO: 34
Substituent: B
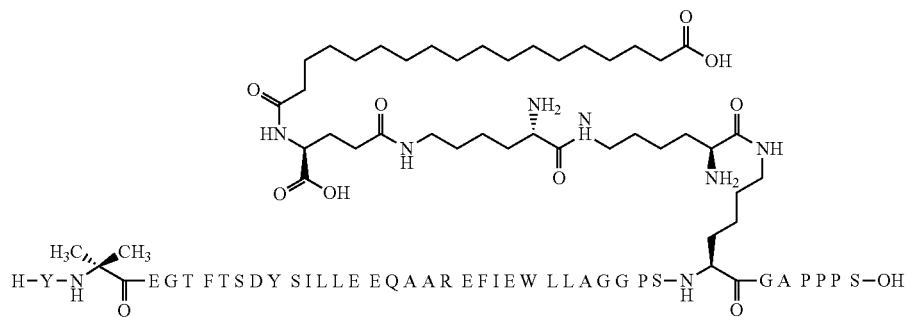
Compound No. 46
SEQ ID NO: 34
Substituent: E
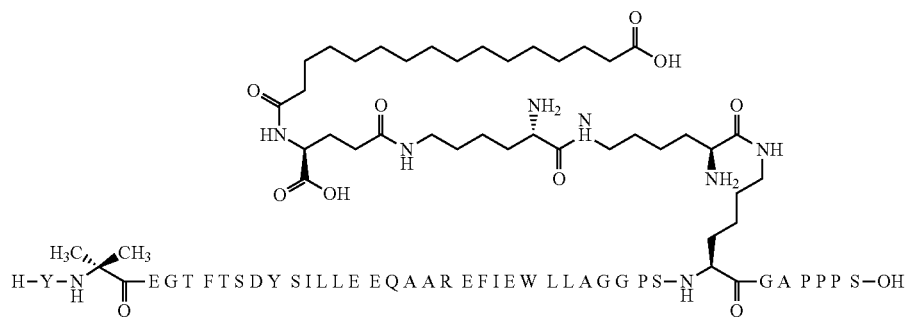

Compound No. 47
SEQ ID NO: 34
Substituent: D

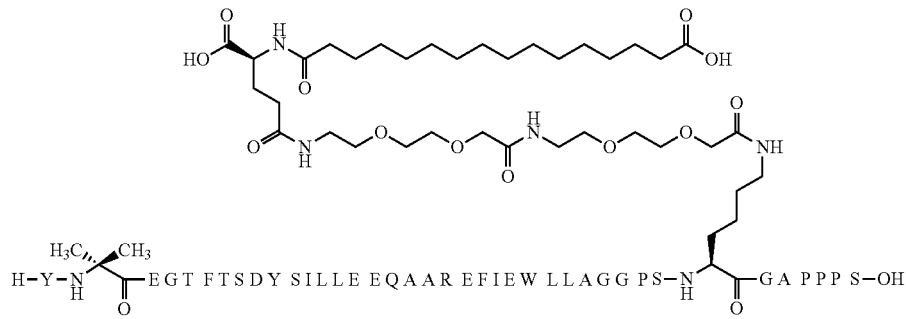

40. The compound according to embodiment 1, wherein the compound is:

Compound No. 31
SEQ ID NO: 25
Substituent: B

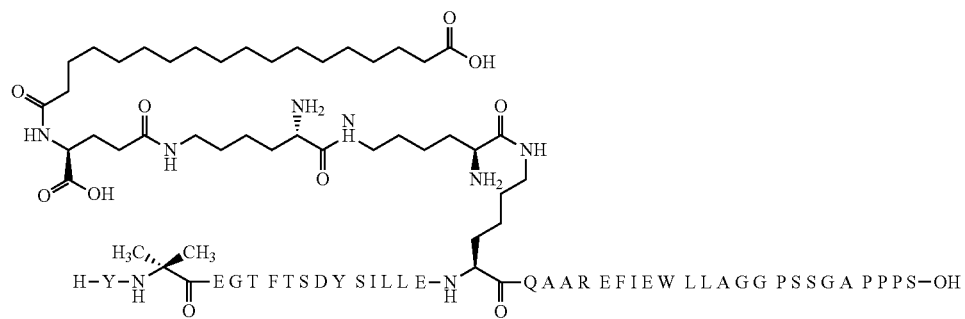

41. A compound according to any of the previous embodiments for use as a medicament.
42. A pharmaceutical composition comprising a compound according to any of the previous embodiments 1-40.
43. The composition according to embodiment 42, wherein said composition is an aqueous liquid.
44. The composition according to embodiment 42, wherein said composition is a solid composition.
45. A pharmaceutical composition according to any of the embodiments 42-44 for prevention and/or treatment of diabetes and/or obesity.
46. A pharmaceutical composition according to any of the embodiments 42-44 for prevention and/or treatment of liver disorders, such as hepatic steatosis, non-alcoholic fatty liver disease (NAFLD), non-alcoholic steatohepatitis (NASH) liver inflammation and/or fatty liver.
47. A method for prevention and/or treatment of diabetes and/or obesity comprising administering to a patient a pharmaceutically active amount of the compound according to any one of embodiments 1-40.
48. A method for prevention and/or treatment of liver disorders, such as hepatic steatosis, non-alcoholic fatty liver disease (NAFLD), non-alcoholic steatohepatitis (NASH) liver inflammation and/or fatty liver comprising administering to a patient a pharmaceutically active amount of the compound according to any one of embodiments 1-40.

49. A nentide. wherein the amino acid sequence of the peptide is (SEQ ID NO.: 47)
$YX_2EGTX_6TSDYSX_{12}X_{13}LEX_{16}QAAX_{20}X_{21}FX_{23}X_{24}WLLX_{28}GX_{30}X_{31}X_{32}$
$X_{33}X_{34}X_{35}X_{36}X_{37}X_{38}X_{39}$ with an optional amide modification of the C-terminus, wherein $X_2$ is Aib or A
$X_6$ is F or V
$X_{12}$ is I or Y
$X_{13}$ is Y, A, L or I
$X_{16}$ is K or E
$X_{20}$ is Q, R, E, H
$X_{21}$ is A or E
$X_{23}$ is I or V
$X_{24}$ is E, Q or N
$X_{28}$ is A or R
$X_{30}$ is G or absent
$X_{31}$ is P or absent
$X_{32}$ is E, S or absent
$X_{33}$ is S, K or absent
$X_{34}$ is G or absent
$X_{35}$ is A or absent $X_{36}$ is P or absent
$X_{37}$ is P or absent
$X_{38}$ is P or absent
$X_{39}$ is S or absent.

50. A peptide, wherein the amino acid sequence of the peptide is (SEQ ID NO.: 36)
YX$_2$EGTX$_6$TSDYSX$_{12}$X$_{13}$LEX$_{16}$QAAX$_{20}$X$_{21}$FX$_{23}$X$_{24}$WLLX$_{28}$GGPX$_{32}$X$_{33}$X$_{34}$X$_{35}$X$_{36}$X$_{37}$X$_{38}$X$_{39}$ with an optional amide modification of the C-terminus, wherein
$X_2$ is Aib or A
$X_6$ is F or V
$X_{12}$ is I or Y
$X_{13}$ is Y, A, L or I
$X_{18}$ is K or E
$X_{20}$ is Q, R, E, H
$X_{21}$ is A or E
$X_{23}$ is I or V
$X_{24}$ is E, Q or N
$X_{28}$ is A or R
$X_{32}$ is E, S or absent
$X_{33}$ is S, K or absent
$X_{34}$ is G or absent
$X_{35}$ is A or absent
$X_{36}$ is P or absent
$X_{37}$ is P or absent
$X_{38}$ is P or absent
$X_{39}$ is S or absent.

51. The peptide according to embodiment 49, wherein $X_{36}$, $X_{37}$, $X_{38}$ and $X_{39}$ are absent.
52. The peptide according to embodiment 49, wherein $X_{34}$, $X_{35}$, $X_{36}$, $X_{37}$, $X_{38}$ and $X_{39}$ are absent.
53. The peptide according to embodiment 49, wherein $X_{32}$, $X_{33}$, $X_{34}$, $X_{35}$, $X_{36}$, $X_{37}$, $X_{38}$ and $X_{39}$ are absent.
54. The peptide according to embodiment 49, wherein $X_{30}$, $X_{31}$, $X_{32}$, $X_{33}$, $X_{34}$, $X_{35}$, $X_{36}$, $X_{37}$, $X_{38}$ and $X_{39}$ are absent.
55. The peptide according to embodiments 49 or 50, wherein $X_{32}X_{33}X_{34}X_{35}$ is selected from the group of: SSGA (SEQ ID NO.: 40), ESGA (SEQ ID NO.: 41) and SKGA (SEQ ID NO.: 42).
56. The peptide according to embodiment 55, wherein $X_{32}X_{33}X_{34}X_{35}$SSGA (SEQ ID NO.: 40).
57. The peptide according to embodiment 55, wherein $X_{32}X_{33}X_{34}X_{35}$ is ESGA (SEQ ID NO.: 41).
58. The peptide according to embodiment 55, wherein $X_{32}X_{33}X_{34}X_{35}$ is SKGA (SEQ ID NO.: 42).
59. The peptide according to any one of embodiments 47-58, wherein the peptide has the amide modification of the C-terminus.
60. The peptide according to embodiment 49, wherein the amino acid sequence of the peptide is (SEQ ID NO.: 37)
YX$_2$EGTX$_6$TSDYSX$_{12}$X$_{13}$LEX$_{16}$QAAX$_{20}$X$_{21}$FX$_{23}$X$_{24}$WLLX$_{28}$GGPSSGAPPPS wherein
$X_2$ is Aib or A
$X_6$ is F or V
$X_{12}$ is I or Y
$X_{13}$ is Y, A, L or I
$X_{18}$ is K or E
$X_{20}$ is Q, R, E, H
$X_{21}$ is A or E
$X_{23}$ is I or V
$X_{24}$ is E, Q or N
$X_{28}$ is A or R.

61. The peptide according to embodiment 48, wherein the amino acid sequence of the peptide is (SEQ ID NO.: 38)
YX$_2$EGTX$_6$TSDYSX$_{12}$X$_{13}$LEX$_{16}$QAAX$_{20}$X$_{21}$FX$_{23}$X$_{24}$WLLX$_{28}$GGPESGAPPPS wherein
$X_2$ is Aib or A
$X_6$ is F or V
$X_{12}$ is I or Y
$X_{13}$ is Y, A, L or I
$X_{18}$ is K or E
$X_{20}$ is Q, R, E, H
$X_{21}$ is A or E
$X_{23}$ is I or V
$X_{24}$ is E, Q or N
$X_{28}$ is A or R.

62. The peptide according to embodiment 49, wherein the amino acid sequence of the peptide is (SEQ ID NO.: 39)
YX$_2$EGTX$_6$TSDYSX$_{12}$X$_{13}$LEX$_{16}$QAAX$_{20}$X$_{21}$FX$_{23}$X$_{24}$WLLX$_{28}$GGPSKGAPPPS wherein
$X_2$ is Aib or A
$X_6$ is F or V
$X_{12}$ is I or Y
$X_{13}$ is Y, A, L or I
$X_{18}$ is K or E
$X_{20}$ is Q, R, E, H
$X_{21}$ is A or E
$X_{23}$ is I or V
$X_{24}$ is E, Q or N
$X_{28}$ is A or R 63. The peptide according to embodiment 49 where the amino acid sequence of the peptide is any one of SEQ ID NO.: 1-27 or 33-35.
64. The peptide according to embodiment 63, wherein the peptide has the amide modification of the C-terminus.
65. The peptide according to any of the previous embodiments 49-64, wherein $X_{13}$LEX$_{16}$QAAX$_{20}$X$_{21}$FX$_{23}$X$_{24}$ is selected from the group consisting of: LLEKQAAREFIN (SEQ ID NO.: 43), LLEKQAAREFIE (SEQ ID NO.: 44), LLEKQAAQEFIE (SEQ ID NO.:45) and LLEEQAAREFIE (SEQ ID NO.: 46).
66. The peptide according to any of the previous embodiments 49-64, wherein the peptide activates the human GLP-1 and GIP receptors in vitro with an $EC_{50}$ of less than 20 pM when measured without HSA in a CRE luciferase reporter assays as described in Example 2.
67. The peptide according to any of the previous embodiments 49-64Error! Reference source not found., wherein $X_{16}$ is K.
68. The peptide according to any of the previous embodiments 49-64, wherein $X_{33}$ is K.
69. A method for preparing a compound according to any of the previous embodiments 1-40.
70. A method for preparing a peptide according to any of the previous embodiments 49-64.

METHODS AND EXAMPLES

LIST OF ABBREVIATIONS

The following abbreviations are used in the following, in alphabetical order:
Ac: acetyl
Ado (also called OEG): 8-amino-3,6-dioxaoctanoic acid
Aib: α-aminoisobutyric acid
API: active pharmaceutical ingredient
AUC: area under the curve
BG: blood glucose
BHK: baby hamster kidney
Boc: tert-butyloxycarbonyl
BW: body weight
CAS: Chemical Abstracts Service
Cl-HOBt: 6-chloro-1-hydroxybenzotriazole
DCM: dichloromethane
DIC: diisopropylcarbodiimide
DIPEA: N,N-diisopropylethylamine
DMEM: Dulbecco's Modified Eagle's Medium
DPBS: Dulbecco's phosphate buffered saline
EDTA: ethylenediaminetetraacetic acid
ELISA: enzyme linked immunosorbent assay
equiv: molar equivalent
FBS: fetal bovine serum
Fmoc: 9-fluorenylmethyloxycarbonyl
GIP: glucose-dependent insulinotropic polypeptide
GIPR: glucose-dependent insulinotropic polypeptide receptor
GLP-1: glucagon-like peptide 1
GLP-1 R: glucagon-like peptide 1 receptor
h: hours
HEPES: 4-(2-hydroxyethyl)-1-piperazineethanesulfonic acid
HFIP: 1,1,1,3,3,3-hexafluoro-2-propanol or hexafluoroisopropanol
HPLC: high performance liquid chromatography
HSA: human serum albumin
i.p.: intraperitoneal
IPGTT: intraperitoneal glucose tolerance test
i.v. intravenously
LCMS: liquid chromatography mass spectroscopy
LYD: Landrace Yorkshire Duroc
MeCN: acetonitrile
MeOH: methanol
mM: millimolar
mmol: millimoles
min: minutes
Mtt: 4-methyltrityl
MW: molecular weight
nM: nanomolar
NMP: 1-methyl-pyrrolidin-2-one
OEG: 8-amino-3,6-dioxaoctanoic acid (also called Ado)
OtBu: tert-butyl ester
Oxyma Pure®: cyano-hydroxyimino-acetic acid ethyl ester
Pbf: 2,2,4,6,7-pentamethyldihydrobenzofuran-5-sulfonyl
PBS: phosphate buffered saline
PD: pharmacodynamic
PK: pharmacokinetic
pM: picomolar
RP: reverse phase
RP-HPLC: reverse phase high performance liquid chromatography
rpm: rounds per minute
RT: room temperature
Rt: retention time
s.c.: subcutaneous
SD: standard deviation
SEC-HPLC: size exclusion high performance liquid chromatography
SEM: standard error of the mean
SNAC: sodium N-[8-(2-hydroxybenzoyl)amino]caprylate
SPPS: solid phase peptide synthesis
tBu: tert-butyl
TFA: trifluoroacetic acid
TIS: triisopropylsilane
Trt: triphenylmethyl or trityl
Trx: tranexamic acid General Methods of Preparation Methods for solid phase peptide synthesis (SPPS methods, including methods for de-protection of amino acids, methods for cleaving the peptide from the resin, and for its purification), as well as methods for detecting and characterising the resulting peptide (LCMS methods) are described here below.

Resins employed for the preparation of C-terminal peptide amides were H-Rink Amide-ChemMatrix resin (loading e.g. 0.5 mmol/g). The Fmoc-protected amino acid derivatives used, unless specifically stated otherwise, were the standard recommended: Fmoc-Ala-OH, Fmoc-Arg(Pbf)-OH, Fmoc-Asn(Trt)-OH, Fmoc-Asp(OtBu)-OH, Fmoc-Cys(Trt)-OH, Fmoc-Gln(Trt)-OH, Fmoc-Glu(OtBu)-OH, Fmoc-Gly-OH, Fmoc-His(Trt)-OH, Fmoc-Ile-OH, Fmoc-Leu-OH, Fmoc-Lys(Boc)-OH, Fmoc-Met-OH, Fmoc-Phe-OH, Fmoc-Pro-OH, Fmoc-Ser(tBu)-OH, Fmoc-Thr(tBu)-OH, Fmoc-Trp(Boc)-OH, Fmoc-Tyr(tBu)-OH, Fmoc-Val-OH, Fmoc-Lys(Mtt)-OH, Fmoc-Aib-OH, etc. supplied from e.g. AAPPTEC, Anaspec, Bachem, ChemImpex, Iris Biotech, Midwest Biotech, Gyros Protein Technologies or Novabiochem. Where nothing else is specified, the natural L-form of the amino acids are used. The N-terminal amino acid was Boc protected at the alpha-amino group, either by using a reagent with the Boc group pre-installed (e.g. Boc-Tyr(tBu)-OH for peptides with Tyr at the N-terminus) or by exchanging the N-terminal Fmoc protective group for the Boc protective group after installation of the amino acid at the peptide N-terminus.

In case of modular albumin binding moiety attachment using SPPS, the following suitably protected building blocks such as but not limited to Fmoc-8-amino-3,6-dioxaoctanoic acid (Fmoc-Ado-OH), Boc-Lys(Fmoc)-OH, Fmoc-Glu-OtBu, hexadecanedioic acid mono-tert-butyl ester, octadecanedioic acid mono-tert-butyl ester, nonadecanedioic acid mono-tert-butyl ester, eicosanedioic acid mono-tert-butyl ester, tetradecanedioic acid mono-tert-butyl ester, or 4-(9-carboxynonyloxy) benzoic acid tert-butyl ester were used. All operations stated below were performed within a 0.1-0.2 mmol synthesis scale range.

1. Synthesis of Resin-Bound Protected Peptide Backbone: Method: SPPS_A

SPPS was performed using Fmoc based chemistry on a Protein Technologies SymphonyX solid phase peptide synthesizer, using the manufacturer supplied protocols with minor modifications. Mixing was accomplished by occasional bubbling with nitrogen. The step-wise assembly was performed using the following steps: 1) pre-swelling of resin in DMF; 2) Fmoc-deprotection by the use of 20% (v/v) piperidine in DMF for two treatments of 10 min each; 3) washes with DMF to remove piperidine; 4) coupling of Fmoc-amino acid by the addition of Fmoc-amino acid (12 equiv) and Oxyma Pure® (12 equiv) as a 0.6 M solution each in DMF, followed by addition of DIC (12 equiv) as a 1.2 M solution in DMF, followed by the addition of DMF to reduce the final concentration of each component to 0.3 M, then mixing for 0.5-4 h; 4) washes with DMF to remove excess reagents; 5) final washes with DCM at the completion of the assembly. Some amino acids such as, but not limited to, those following a sterically hindered amino acid (e.g. Aib) were coupled with an extended reaction time (e.g. 4 h) to ensure reaction completion.

Method: SPPS_B

The protected peptidyl resin was synthesized according to the Fmoc strategy on an Applied Biosystems 431A solid-phase peptide synthesizer using the manufacturer supplied general Fmoc protocols. Mixing was accomplished by vortexing and occasional bubbling with nitrogen. The step-wise assembly was done using the following steps: 1) activation of Fmoc-amino acid by dissolution of solid Fmoc-acid acid (10 equiv) in Cl-HOBt (10 equiv) as a 1 M solution in NMP, then addition of DIC (10 equiv) as a 1 M solution in NMP, then mixing simultaneous to steps 2-3; 2) Fmoc-deprotection by the use of 20% (v/v) piperidine in NMP for one treatment of 3 min then a second treatment of 15 min; 3) washes with NMP to remove piperidine; 4) addition of activated Fmoc-amino acid solution to resin, then mixing for 45-90 min; 4) washes with NMP to remove excess reagents; 5) final washes with DCM at the completion of the assembly. The standard protected amino acid derivatives listed above were supplied in pre-weighed cartridges (from e.g. Midwest Biotech), and non-standard derivatives were weighed by hand. Some amino acids such as, but not limited to, those following a sterically hindered amino acid (e.g. Aib) were "double coupled" to ensure reaction completion, meaning that after the first coupling (e.g. 45 min) the resin is drained, more reagents are added (Fmoc-amino acid, DIC, Cl-HOBt), and the mixture allowed to react again (e.g. 45 min).

Method: SPPS_C

SPPS was performed using Fmoc based chemistry on a PreludeX solid phase peptide synthesizer, using the manufacturer supplied protocols with minor modifications. Mixing was accomplished by shaking at 350 rpm and occasional bubbling with nitrogen. The step-wise assembly was performed using the following steps: 1) pre-swelling of resin in DMF; 2) Fmoc-deprotection by the use of 20% (v/v) piperidine in DMF for one treatment of 3 min at 70° C.; 3) washes with DMF to remove piperidine; 4) coupling of Fmoc-amino acid by the addition of Fmoc-amino acid (12 equiv) and Oxyma Pure® (12 equiv) as a 0.4 M solution each in DMF, followed by addition of DIC (12 equiv) as a 1.2 M solution in DMF, then mixing for 5 min at 70° C.; 4) washes with DMF to remove excess reagents; 5) final washes with DCM at the completion of the assembly. Some amino acids such as, but not limited to, those following a sterically hindered amino acid (e.g. Aib) were coupled with an extended reaction time (e.g. 15 min) to ensure reaction completion.

2. Attachment of substituent to resin-bound protected peptide backbone

Method: SC_A

The N-epsilon-lysine protection Mtt protection group was removed by washing the resin with 30% HFIP in DCM for two treatments of 45 min each, following by washing with DCM and DMF. Acylation was performed on a Protein Technologies SymphonyX solid phase peptide synthesizer using the protocols described in method SPPS_A using stepwise addition of building blocks, such as, but not limited to, Boc-Lys(Fmoc)-OH, Fmoc-8-amino-3,6-dioxaoctanoic acid, Fmoc-Glu-OtBu, hexadecanedioic acid mono-tert-butyl ester, octadecanedioic acid mono-tert-butyl ester, and eicosanedioic acid mono-tert-butyl ester.

Method: SC_B

The N-epsilon-lysine protection Mtt protection group was removed by washing the resin with 30% HFIP in DCM for two treatments of 45 min each, following by washing with DCM and DMF. Acylation was performed on an Applied Biosystems 431A solid-phase peptide synthesizer using the protocols described in method SPPS_B using stepwise addition of building blocks, such as, but not limited to, Boc-Lys(Fmoc)-OH, Fmoc-8-amino-3,6-dioxaoctanoic acid, Fmoc-Glu-OtBu, hexadecanedioic acid mono-tert-butyl ester, octadecanedioic acid mono-tert-butyl ester, and eicosanedioic acid mono-tert-butyl ester.

Method: SC_C

The N-epsilon-lysine protection Mtt protection group was removed by washing the resin with 30% HFIP in DCM for two treatments of 45 min each, following by washing with DCM and DMF. Acylation was performed on a Protein Technologies PreludeX solid phase peptide synthesizer using the protocols described in method SPPS_C using stepwise addition of building blocks, such as, but not limited to, Boc-Lys(Fmoc)-OH, Fmoc-8-amino-3,6-dioxaoctanoic acid, Fmoc-Glu-OtBu, hexadecanedioic acid mono-tert-butyl ester, octadecanedioic acid mono-tert-butyl ester, and eicosanedioic acid mono-tert-butyl ester.

3. Cleavage of resin bound peptide and purification:

Method: CP_A

Following completion of the sidechain synthesis, the peptidyl resin was washed with DCM and dried, then treated with TFA/water/TIS (95:2.5:2.5 v/v/v) for approximately 2 h, followed by precipitation with diethyl ether. The precipitate was washed with diethyl ether, dissolved in a suitable solvent (e.g. 2:1 water/MeCN), and let stand until all labile adducts decomposed. Purification was performed by reversed-phase preparative HPLC (Waters 2545 binary gradient module, Waters 2489 UV/Visible detector, Waters fraction collector III) on a Phenomenex Luna C8(2) column (10 μM particle size, 100 Å pore size, 250×21.2 mm dimensions). Separation of impurities and product elution was accomplished using an increasing gradient of MeCN in water containing 0.1% TFA. Relevant fractions were checked for identity and purity by analytical LCMS. Fractions containing the pure desired product were pooled and freeze-dried to afford the peptide TFA salt as a white solid.

4. Salt exchange from TFA to sodium salt:

Method: SX_A

The freeze-dried peptide isolated from method CP_A was dissolved to 5-20 mg/mL in an appropriate aqueous buffer (e.g. 4:1 water/MeCN, 0.2 M sodium acetate) and adjusted to pH 7-8 with 1 M NaOH if necessary to achieve full solubility. The buffered solutions containing the peptide were salt-exchanged using a Sep-Pak C18 cartridge (0.5-2 g): The cartridge was first equilibrated with 4 column volumes of isopropanol, then 4 column volumes of MeCN, then 8 column volumes of water. The peptide solution was applied to the cartridge, and the flow through was reapplied to ensure complete retention of peptide. The cartridge was washed with 4 column volumes of water, then 10 column volumes of a buffer solution (e.g. pH 7.5) containing such as, but not limited to, $NaHCO_3$, NaOAc, or $Na_2HPO_4$. The column was washed with 4 column volumes of water, and the peptide was eluted with 5-10 column volumes of 50-80% MeCN in water. The peptide-containing eluent was freeze-dried to afford the peptide sodium salt as a white solid, which was used as such.

General Methods of Detection and Characterisation
LCMS methods:
Method: LCMS_A

LCMS_A was performed on a setup consisting of an Agilent 1260 Infinity series HPLC system and an Agilent Technologies 6120 Quadrupole MS. Eluents: A: 0.05% TFA in water; B: 0.05% TFA in 9:1 MeCN/water.

The analysis was performed at RT (column temp 37C) by injecting an appropriate volume of the sample onto the column which was eluted with a gradient of A and B. Column: Phenomenex Kinetex C8, 2.6 μm, 100 Å, 4.6×75 mm. Gradient run time: Linear 10-80% B over 10 min at a flow rate of 1.0 mL/min. Detection: diode array detector set to 214 nm. MS ionisation mode: API-ES, positive polarity. MS scan mass range: 500-2000 amu.

Method: LCMS_B

LCMS_B was performed on a setup consisting of an Agilent 1260 Infinity series HPLC system and an Agilent Technologies 6120 Quadrupole MS. Eluents: A: 0.05% TFA in water; B: 0.05% TFA in 9:1 MeCN/water.

The analysis was performed at RT (column temp 37C) by injecting an appropriate volume of the sample onto the column which was eluted with a gradient of A and B. Column: Phenomenex Kinetex C8, 2.6 μm, 100 Å, 4.6×75 mm. Gradient run time: Linear 20-100% B over 10 min at a flow rate of 1.0 mL/min. Detection: diode array detector set to 214 nm. MS ionisation mode: API-ES, positive polarity. MS scan mass range: 500-2000 amu While certain features of the invention have been illustrated and described herein, many modifications, substitutions, changes, and equivalents will now occur to those of ordinary skill in the art. It is, therefore, to be understood that the appended embodiments are intended to cover all such modifications and changes as fall within the true spirit of the invention.

Example 1

Synthesis of Compounds

The compounds are in the following described using single letter amino acid codes, except for Aib. The substituent is included after the lysine (K) residue to which it is attached.

Compound No. 1

Y-Aib-EGTFTSDYSIYLE-K[(2S)-2-amino-6-[[(2S)-2-amino-6-[[(4S)-4-carboxy-4-(19-carboxynonadecanoy-lamino)butanoyl]amino]hexanoyl]amino]hexanoyl]-QAAQEFVNWLLAGGPSSGAPPPS-NH$_2$

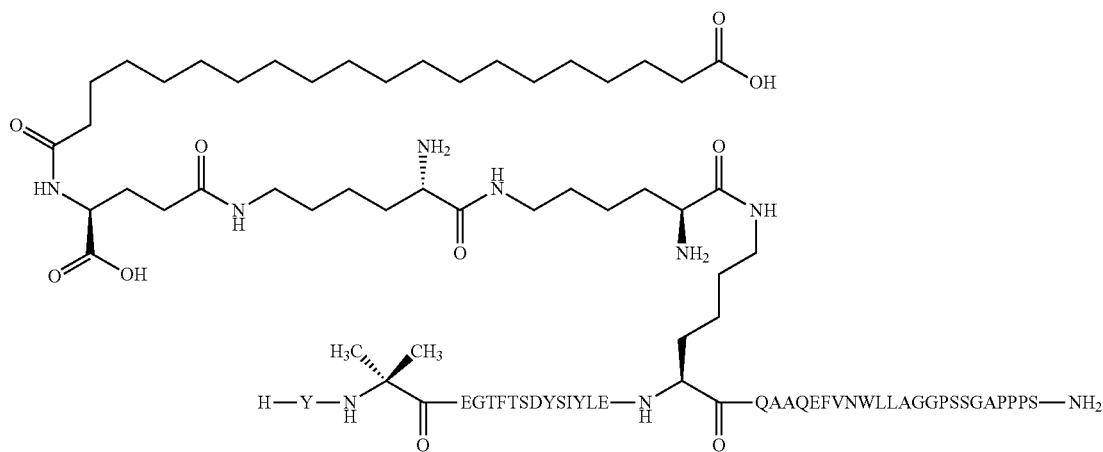

SEQ ID NO: 1 with C-terminal amide modification; Substituent: C; Substituent position: K16

Synthesis methods: SPPS_A; SC_B; CP_A

Molecular weight (average) calculated: 4873.5 Da

LCMS_A: Rt=6.0 min; found [M+3H]$^{3+}$1625.4, [M+4H]$^{4+}$1219.1.

Compound No. 2

Y-Aib-EGTFTSDYSYYLE-K[(2S)-2-amino-6-[[(2S)-2-amino-6-[[(4S)-4-carboxy-4-(19-carboxynonadecanoy-lamino)butanoyl]amino]hexanoyl]amino]hexanoyl]-QAAQEFVNWLLAGGPSSGAPPPS-NH$_2$

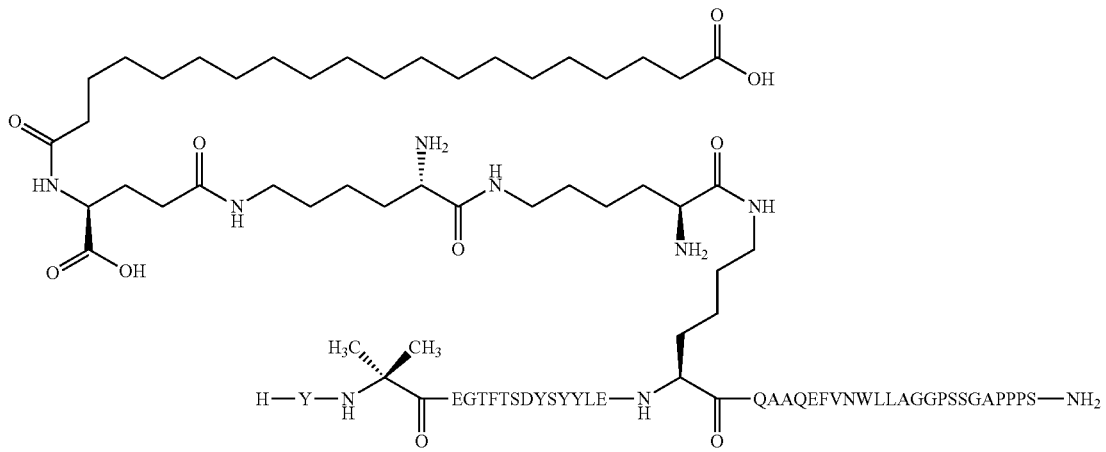
SEQ ID NO: 2 with C-terminal amide modification; Substituent: C; Substituent position: K16
Synthesis methods: SPPS_A; SC_B; CP_A
Molecular weight (average) calculated: 4923.5 Da
LCMS_A: Rt=6.0 min; found [M+3H]$^{3+}$1641.8, [M+4H]$^{4+}$1237.5
Compound No. 3
Y-Aib-EGTFTSDYSYYLE-K[(2S)-2-amino-6-[[(2S)-2-amino-6-[[(4S)-4-carboxy-4-(17-carboxyheptadecanoylamino)butanoyl]amino]hexanoyl]amino]hexanoyl]-QAAQEFVNWLLAGGPSSGAPPPS-NH$_2$
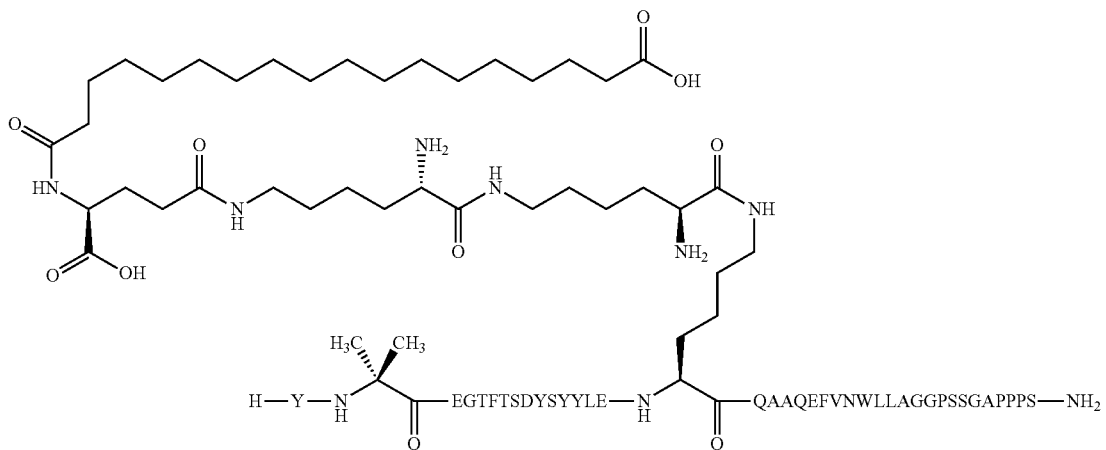

SEQ ID NO: 2 with C-terminal amide modification;
Substituent: B; Substituent position: K16
  Synthesis methods: SPPS_A; SC_B; CP_A
  Molecular weight (average) calculated: 4895.4 Da
  LCMS_A: Rt=5.7 min; found [M+3H]$^{3+}$1632.7, [M+4H]$^{4+}$1224.6
  Compound No. 4
  Y-Aib-EGTFTSDYSYYLE-K[(2S)-2-amino-6-[[(2S)-2-amino-6-[[(4S)-4-carboxy-4-(17-carboxyheptadecanoy-lamino)butanoyl]amino]hexanoyl]amino]hexanoyl]-QAAQAFVNWLLAGGPSSGAPPPS-NH$_2$

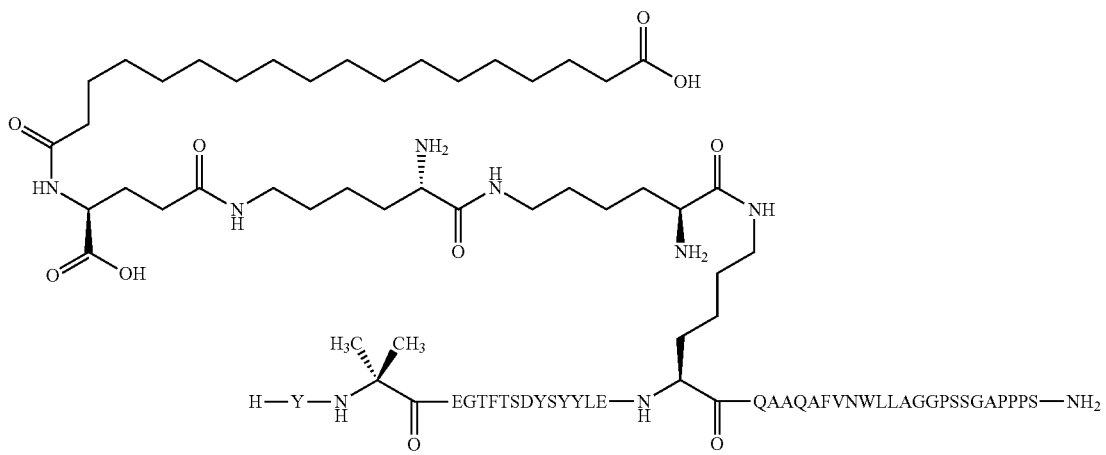

SEQ ID NO: 3 with C-terminal amide modification;
Substituent: B; Substituent position: K16
  Synthesis methods: SPPS_A; SC_B; CP_A
  Molecular weight (average) calculated: 4837.4 Da
  LCMS_A: Rt=5.7 min; found [M+3H]$^{3+}$1613.3, [M+4H]$^{4+}$1210.1
  Compound No. 5
  Y-Aib-EGTFTSDYSYYLE-K[(2S)-2-amino-6-[[(2S)-2-amino-6-[[(4S)-4-carboxy-4-(17-carboxyheptadecanoy-lamino)butanoyl]amino]hexanoyl]amino]hexanoyl]-QAAQAFVNWLLAGGPSSGAPPPS-OH

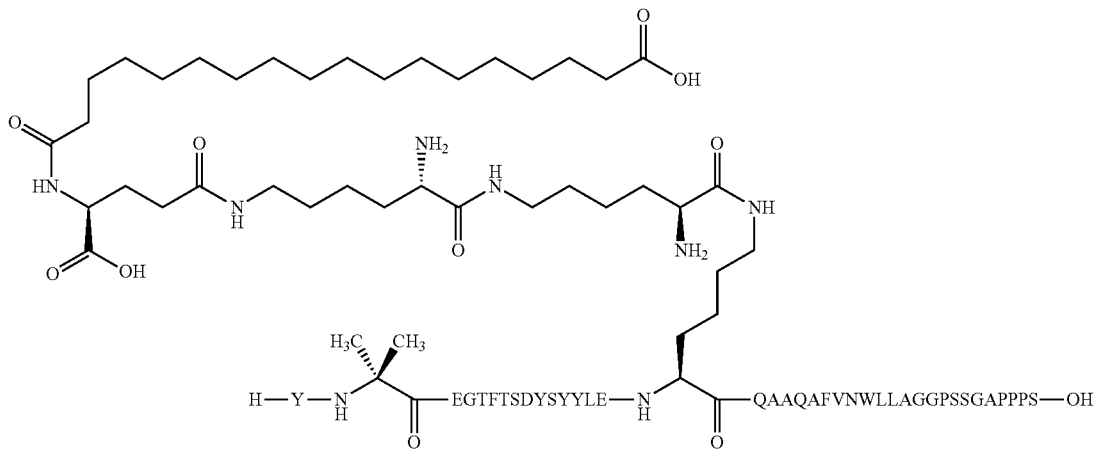

SEQ ID NO: 3; Substituent: B; Substituent position: K16
Synthesis methods: SPPS_B; SC_B; CP_A
Molecular weight (average) calculated: 4838.4 Da
LCMS_A: Rt=5.7 min; found [M+3H]$^{3+}$1613.6, [M+4H]$^{4+}$1210.4

Compound No. 6
Y-Aib-EGTFTSDYSIYLE-K[(2S)-2-amino-6-[[(2S)-2-amino-6[[(4S)-4-carboxy-4-(17-carboxyheptadecanoylamino)butanoyl]amino]hexanoyl]amino]hexanoyl]-QAAREFVNWLLAGGPSSGAPPPS-NH$_2$

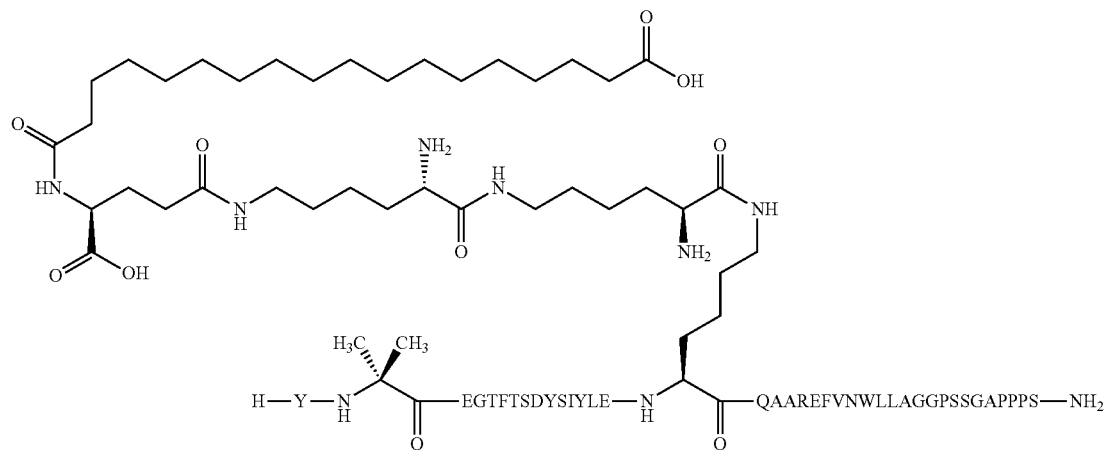

SEQ ID NO: 4 with C-terminal amide modification; Substituent: B; Substituent position: K16 Synthesis methods: SPPS_B; SC_B; CP_A
Molecular weight (average) calculated: 4873.5 Da
LCMS_A: Rt=5.6 min; found [M+3H]$^{3+}$1625.3, [M+4H]$^{4+}$1219.1

Compound No. 7
Y-Aib-EGTFTSDYSIYLE-K[2-[2-[2-[[2-[2-[2-[[(4S-carboxy-4-(17-carboxyheptadecanoylamino)butanoyl]amino]ethoxy]ethoxy]acetyl]amino]ethoxy]ethoxy]acetyl]-QAAREFVNWLLAGGPSSGAPPPS-NH$_2$

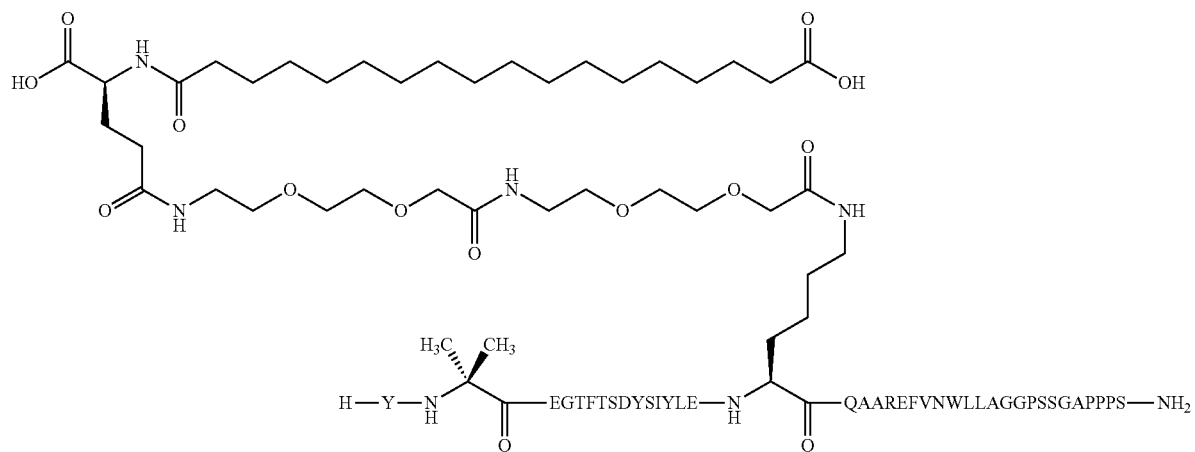

SEQ ID NO: 4 with C-terminal amide modification;
Substituent: A; Substituent position: K16
Synthesis methods: SPPS_B; SC_B; CP_A
Molecular weight (average) calculated: 4907.4 Da
LCMS_A: Rt=6.3 min; found[M+3H]$^{3+}$1636.5, [M+4H]$^{4+}$1227.9

Compound No. 8
Y-Aib-EGTFTSDYSIYLE-K[(2S)-2-amino-6-[[(2S)-2-amino-6-[[(4S)-4-carboxy-4-(17-carboxyheptadecanoylamino)butanoyl]amino]hexanoyl]amino]hexanoyl]-QAAREFINWLLAGGPSSGAPPPS-NH$_2$

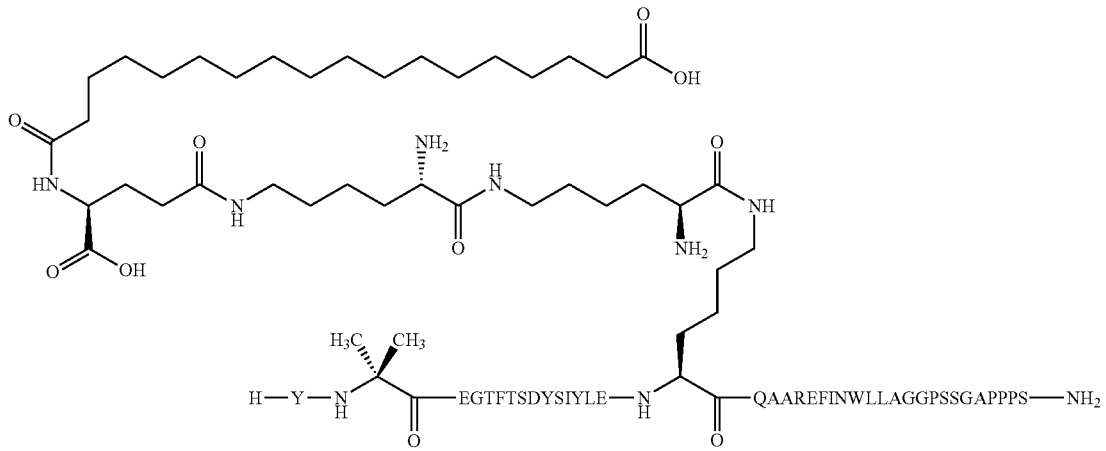

SEQ ID NO: 5 with C-terminal amide modification;
Substituent: B; Substituent position: K16
Synthesis methods: SPPS_A; SC_A; CP_A
Molecular weight (average) calculated: 4887.5 Da
LCMS_A: Rt=5.7 min; found [M+3H]$^{3+}$1629.8, [M+4H]$^{4+}$1222.8

Compound No. 9
Y-Aib-EGTFTSDYSIYLE-K[(2S)-2-amino-6-[[(2S)-2-amino-6-[[(4S)-4-carboxy-4-(17-carboxyheptadecanoylamino)butanoyl]amino]hexanoyl]amino]hexanoyl]-QAAREFIEWLLAGGPSSGAPPPS-OH

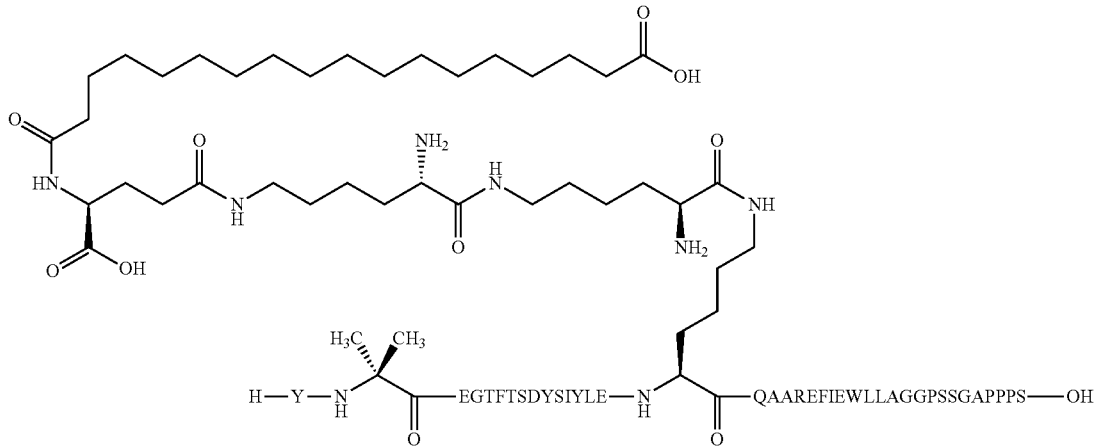

SEQ ID NO: 6; Substituent: B; Substituent position: K16
Synthesis methods: SPPS_A; SC_B; CP_A
Molecular weight (average) calculated: 4903.5 Da
LCMS_A: Rt=5.8 min; found [M+3H]$^{3+}$1635.2, [M+4H]$^{4+}$1226.8

Compound No. 10
Y-Aib-EGTFTSDYSIYLE-K[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-QAAREFIEWLLAGGPSSGAPPPS-OH

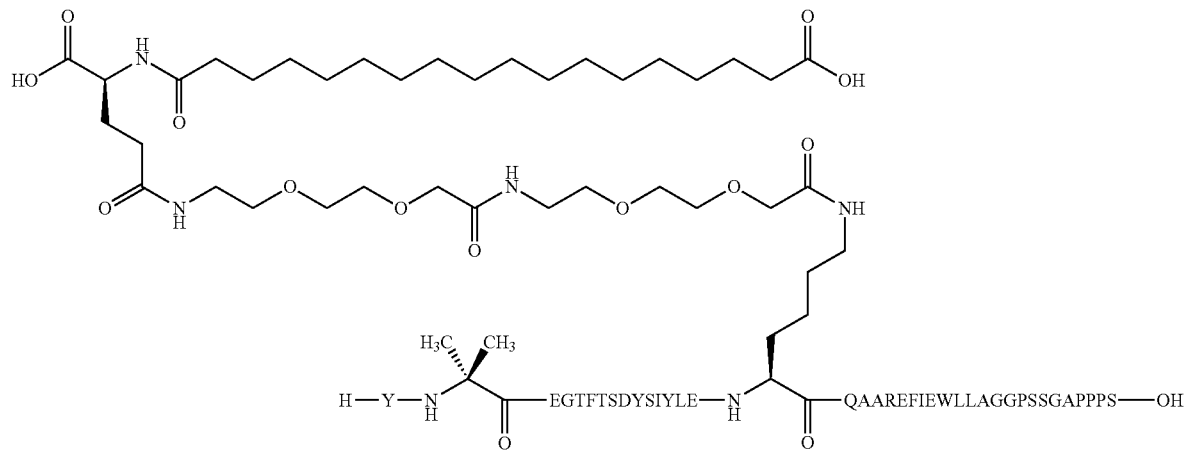

SEQ ID NO: 6; Substituent: A; Substituent position: K16
Synthesis methods: SPPS_A; SC_B; CP_A
Molecular weight (average) calculated: 4937.5 Da
LCMS_A: Rt=6.5 min; found [M+3H]$^{3+}$1646.6, [M+4H]$^{4+}$1235.1

Compound No. 11
Y-Aib-EGTFTSDYSIYLE-K[(2S)-2-amino-6-[[(2S)-2-amino-6-[[(4S)-4-carboxy-4-(17-carboxyheptadecanoylamino)butanoyl]amino]hexanoyl]amino]hexanoyl]-QAAREFINWLLAGGPSSGAPPPS-OH

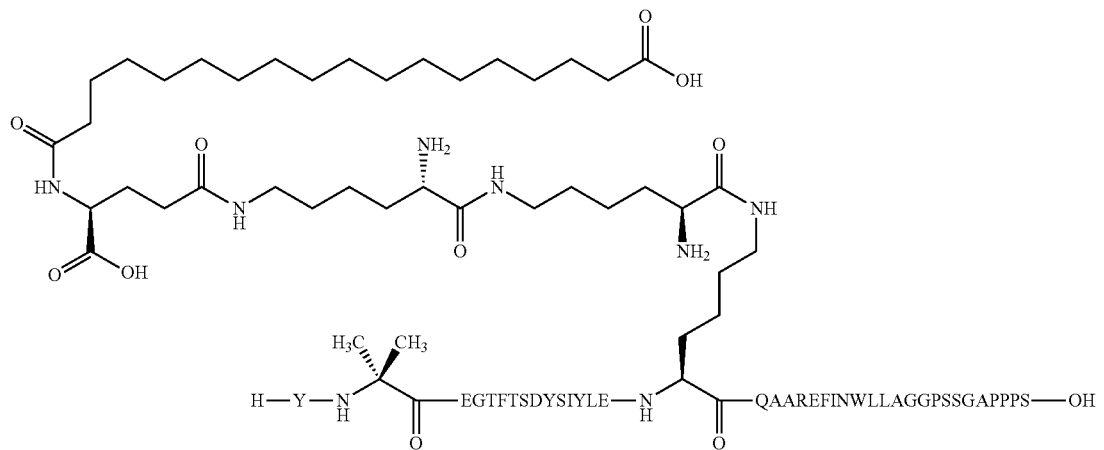

SEQ ID NO: 5; Substituent: B; Substituent position: K16
Synthesis methods: SPPS_A; SC_C; CP_A
Molecular weight (average) calculated: 4888.5 Da
LCMS_A: Rt=5.7 min; found [M+3H]$^{3+}$1630.2, [M+4H]$^{4+}$1222.9

Compound No. 12
Y-Aib-EGTFTSDYSIYLE-K[(2S)-2-amino-6-[[(2S)-2-amino-6-[[(4S)-4-carboxy-4-(17-carboxyheptadecanoy-lamino)butanoyl]amino]hexanoyl]amino]hexanoyl]-QAAREFIEWLLRGGPSSGAPPPS-OH

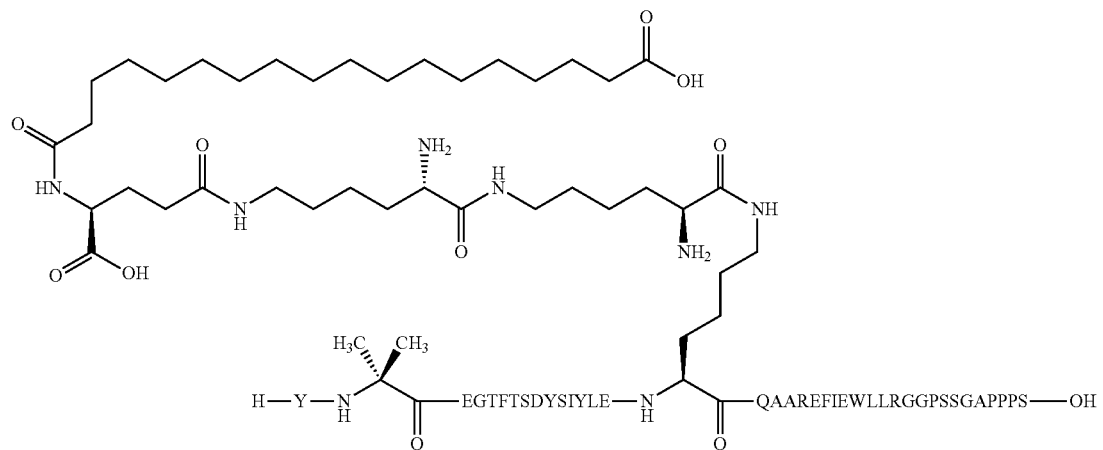

Synthesis methods: SPPS_A; SC_C; CP_A
SEQ ID NO: 7; Substituent: B; Substituent position: K16
Molecular weight (average) calculated: 4988.6 Da
LCMS_A: Rt=5.7 min; found [M+3H]$^{3+}$1663.6, [M+4H]$^{4+}$1248.0

Compound No. 13
Y-Aib-EGTFTSDYSIYLE-K[(2S)-2-amino-6-[[(2S)-2-amino-6-[[(4S)-4-carboxy-4-(17-carboxyheptadecanoy-lamino)butanoyl]amino]hexanoyl]amino]hexanoyl]-QAAREFIEWLLRGGPESGAPPPS-OH

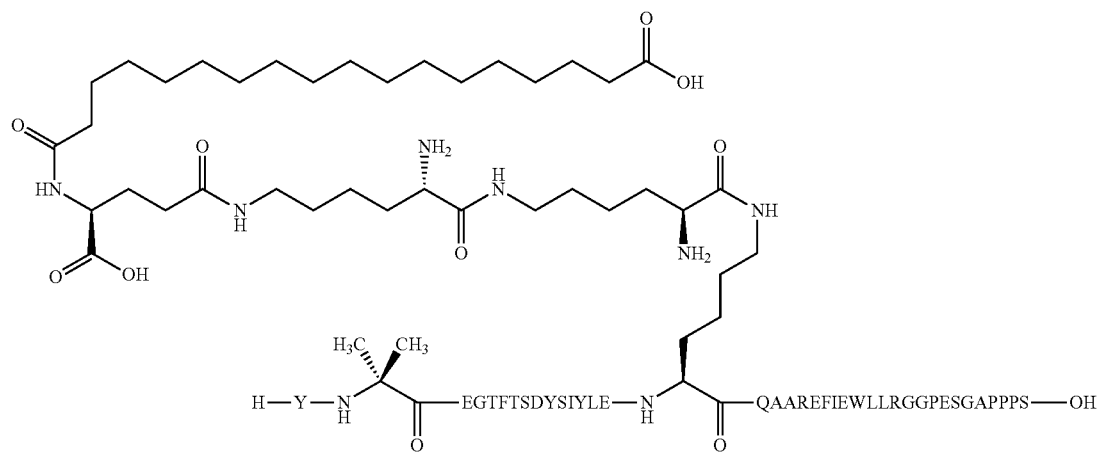

SEQ ID NO: 8; Substituent: B; Substituent position: K16
Synthesis methods: SPPS_A; SC_C; CP_A
Molecular weight (average) calculated: 5030.6 Da
LCMS_A: Rt=5.7 min; found [M+3H]$^{3+}$1677.7, [M+4H]$^{4+}$1258.4
Compound No. 14
Y-Aib-EGTFTSDYSIALE-K[(2S)-2-amino-6-[[(2S)-2-amino-6-[[(4S)-4-carboxy-4-(17-carboxyheptadecanoy-lamino)butanoyl]amino]hexanoyl]amino]hexanoyl]-QAAREFINWLLAGGPSSGAPPPS-OH

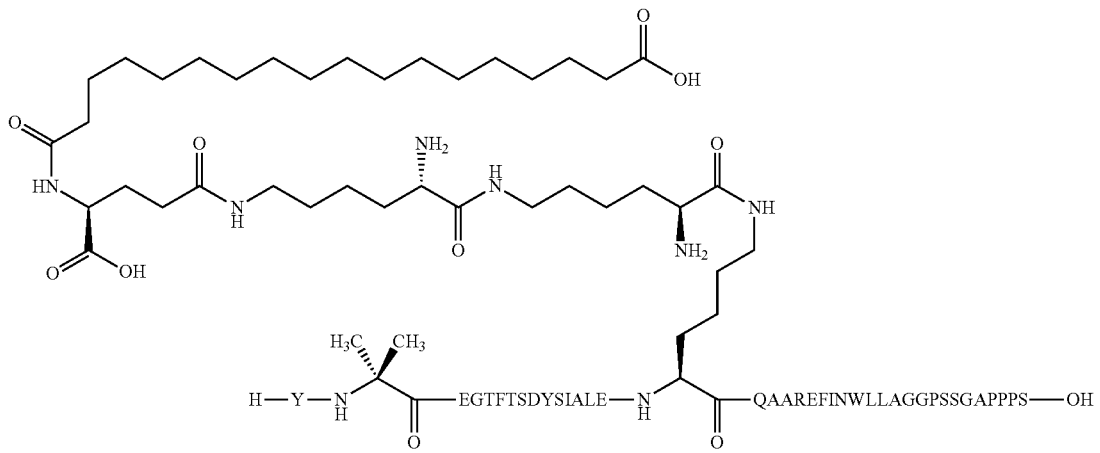

SEQ ID NO: 9; Substituent: B; Substituent position: K16
Synthesis methods: SPPS_A; SC_C; CP_A
Molecular weight (average) calculated: 4796.4 Da
LCMS_A: Rt=5.7 min; found [M+3H]$^{3+}$1599.6, [M+4H]$^{4+}$1199.8
Compound No. 15
Y-Aib-EGTFTSDYSILLE-K[(2S)-2-amino-6-[[(2S)-2-amino-6-[[(4S)-4-carboxy-4-(17-carboxyheptadecanoy-lamino)butanoyl]amino]hexanoyl]amino]hexanoyl]-QAAREFINWLLAGGPSSGAPPPS-OH

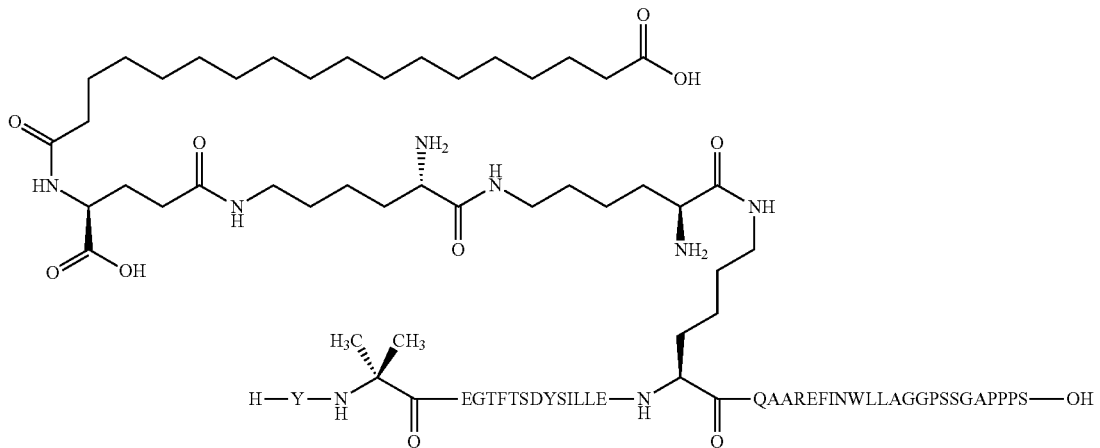

SEQ ID NO: 10; Substituent: B; Substituent position: K16
Synthesis methods: SPPS_A; SC_A; CP_A; SX_A
Molecular weight (average) calculated: 4838.5 Da
LCMS_A: Rt=5.8 min; found [M+3H]$^{3+}$1613.4, [M+4H]$^{4+}$1210.3

Compound No. 16
Y-Aib-EGTFTSDYSIYLE-K[(2S)-2-amino-6-[[(2S)-2-amino-6-[[(4S)-4-carboxy-4-(19-carboxynonadecanoy-lamino)butanoyl]amino]hexanoyl]amino]hexanoyl]-QAAREFINWLLAGGPSSGAPPPS-OH

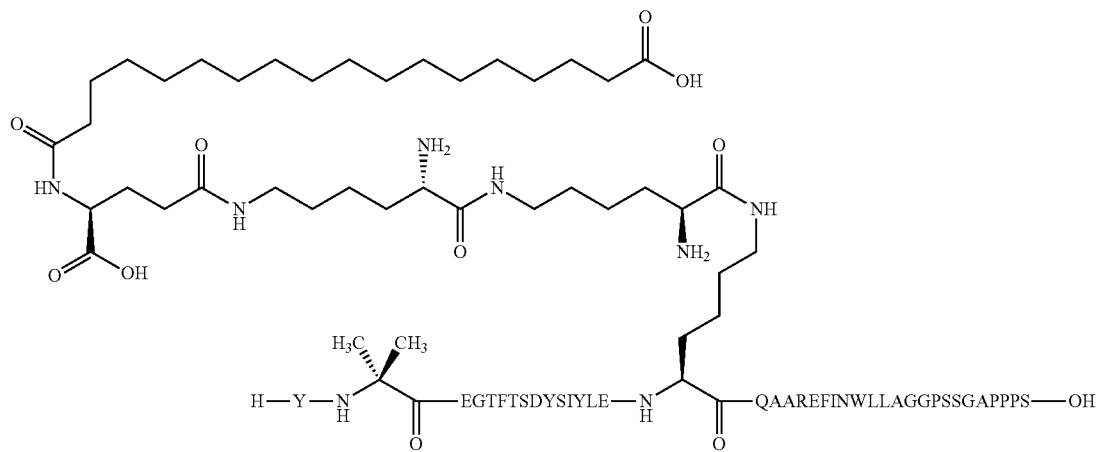

SEQ ID NO: 5; Substituent: C; Substituent position: K16
Synthesis methods: SPPS_A; SC_A; CP_A
Molecular weight (average) calculated: 4916.5 Da
LCMS_A: Rt=6.0 min; found [M+3H]$^{3+}$1639.6, [M+4H]$^{4+}$1229.9

Compound No. 17
YAEGTFTSDYSIYLE-K[(2S)-2-amino-6-[[(2S)-2-amino-6-[[(4S)-4-carboxy-4-(17-carboxyheptadecanoy-lamino)butanoyl]amino]hexanoyl]amino]hexanoyl]-QAAREFINWLLAGGPSSGAPPPS-OH

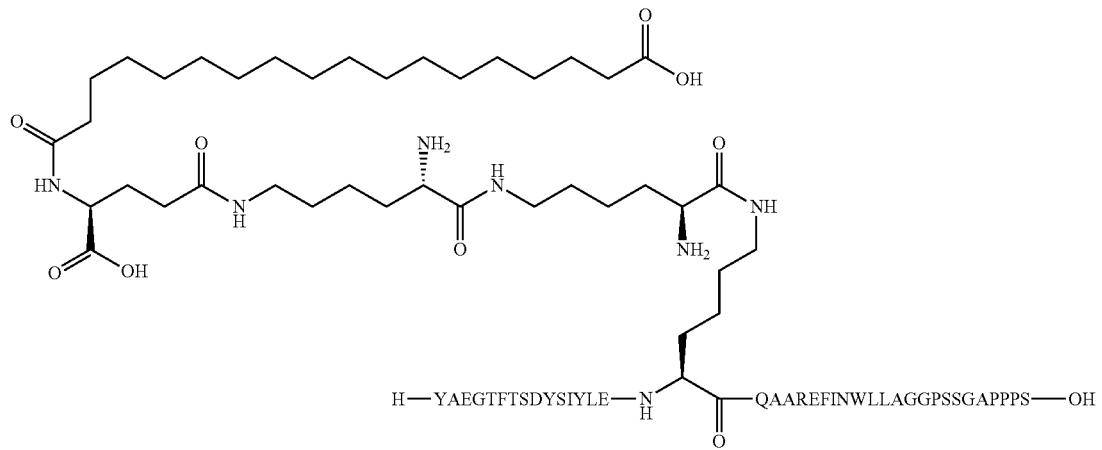

SEQ ID NO: 11; Substituent: B; Substituent position: K16
Synthesis methods: SPPS_C; SC_A; CP_A
Molecular weight (average) calculated: 4874.5 Da
LCMS_A: Rt=5.7 min; found [M+3H]³⁺1625.4, [M+4H]⁴⁺1219.4
Compound No. 18
Y-Aib-EGTFTSDYSILLE-K[(2S)-2-amino-6-[[(2S)-2-amino-6-[[(4S)-4-carboxy-4-(17-carboxyheptadecanoylamino)butanoyl]amino]hexanoyl]amino]hexanoyl]QAAREFINWLLAG-OH

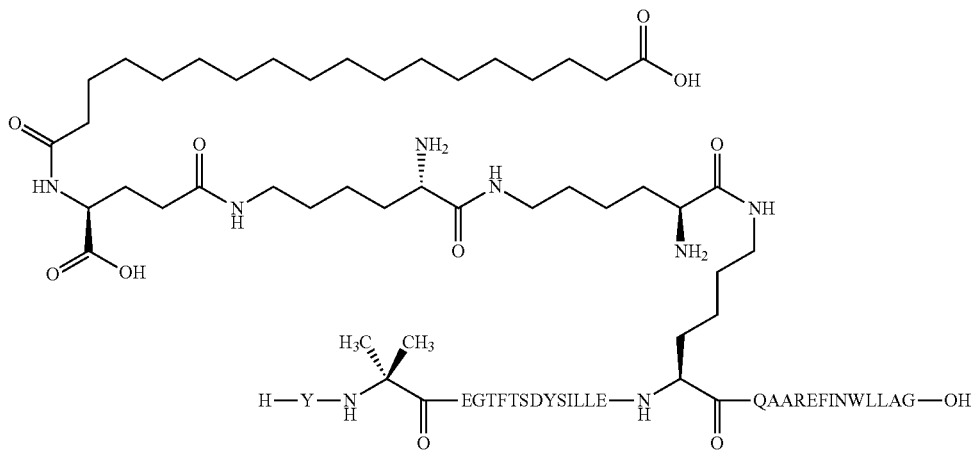

SEQ ID NO: 12; Substituent: B; Substituent position: K16
Synthesis methods: SPPS_A; SC_A; CP_A
Molecular weight (average) calculated: 4003.6 Da
LCMS_A: Rt=6.2 min; found [M+3H]³⁺1335.3, [M+4H]⁴⁺1001.7
Compound No. 19
Y-Aib-EGTFTSDYSILLE-K[(2S)-2-amino-6-[[(2S)-2-amino-6-[[(4S)-4-carboxy-4-(17-carboxyheptadecanoylamino)butanoyl]amino]hexanoyl]amino]hexanoyl]-QAAREFINWLLAGGP-OH

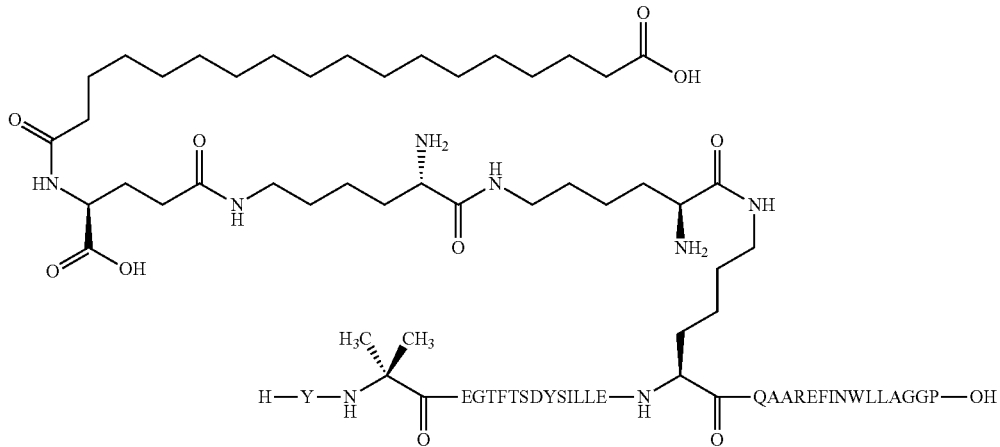

SEQ ID NO: 13; Substituent: B; Substituent position: K16
Synthesis methods: SPPS_A; SC_A; CP_A
Molecular weight (average) calculated: 4157.8 Da
LCMS_A: Rt=6.1 min; found [M+3H]$^{3+}$1386.6, [M+4H]$^{4+}$1040.3

Compound No. 20
Y-Aib-EGTFTSDYSILLE-K[(2S)-2-amino-6-[[(2S)-2-amino-6-[[(4S)-4-carboxy-4-(17-carboxyheptadecanoy-lamino)butanoyl]amino]hexanoyl]amino]hexanoyl]-QAAREFINWLLAGGPSS-OH

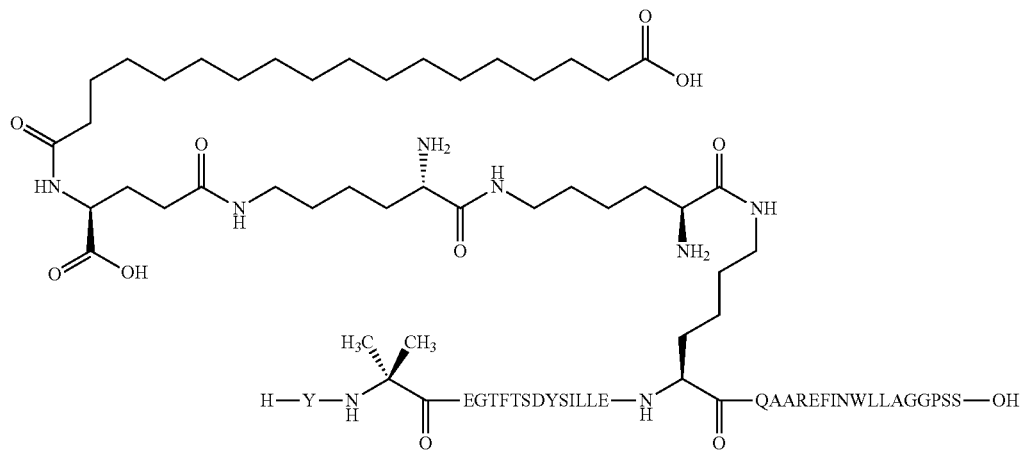

SEQ ID NO: 14; Substituent: B; Substituent position: K16
Synthesis methods: SPPS_A; SC_A; CP_A
Molecular weight (average) calculated: 4331.9 Da
LCMS_A: Rt=5.9 min; found [M+3H]$^{3+}$1444.7, [M+4H]$^{4+}$1083.7

Compound No. 21
Y-Aib-EGTFTSDYSILLE-K[(2S)-2-amino-6-[[(2S)-2-amino-6-[[(4S)-4-carboxy-4-(17-carboxyheptadecanoy-lamino)butanoyl]amino]hexanoyl]amino]hexanoyl]-QAAR-EFINWLLAGGPSSGA-OH

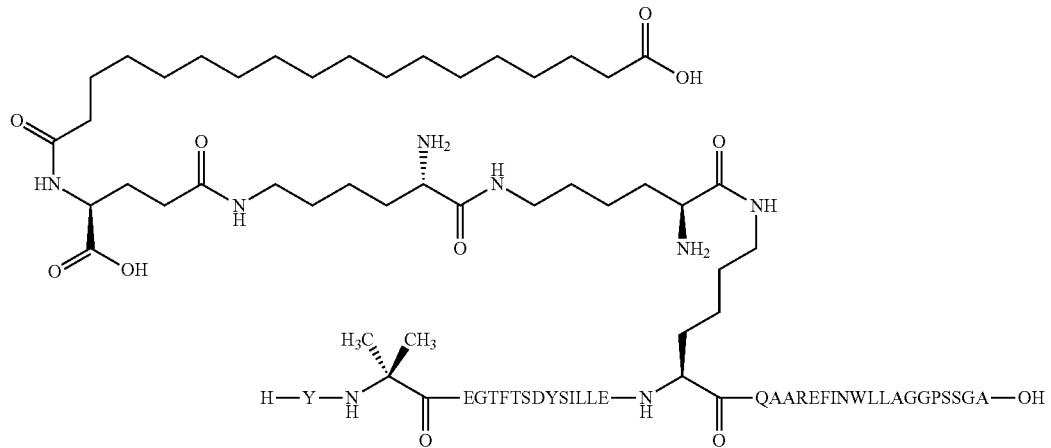

SEQ ID NO: 15; Substituent: B; Substituent position: K16
Synthesis methods: SPPS_A; SC_A; CP_A
Molecular weight (average) calculated: 4460.0 Da
LCMS_A: Rt=5.9 min; found [M+3H]$^{3+}$1487.5, [M+4H]$^{4+}$1116.1

Compound No. 22

Y-Aib-EGTFTSDYSILLE-K[(2S)-2-amino-6-[[(2S)-2-amino-6-[[(4S)-4-carboxy-4-(17-carboxyheptadecanoylamino)butanoyl]amino]hexanoyl]amino]hexanoyl]-QAAREFVNWLLAGGPSSGAPPPS-OH

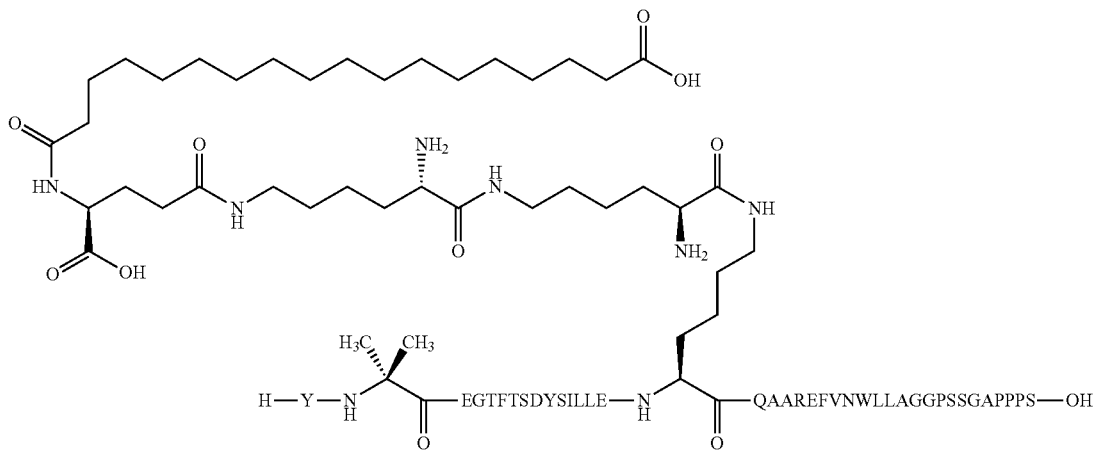

SEQ ID NO: 16; Substituent: B; Substituent position: K16
Synthesis methods: SPPS_A; SC_A; CP_A
Molecular weight (average) calculated: 4824.4 Da
LCMS_A: Rt=5.7 min; found [M+3H]$^{3+}$1608.9, [M+4H]$^{4+}$1206.9

Compound No. 23

Y-Aib-EGTFTSDYSILLE-K[(2S)-2-amino-6-[[(2S)-2-amino-6-[[(4S)-4-carboxy-4-(17-carboxyheptadecanoylamino)butanoyl]amino]hexanoyl]amino]hexanoyl]-QAAREFIQWLLAGGPSSGAPPPS-OH

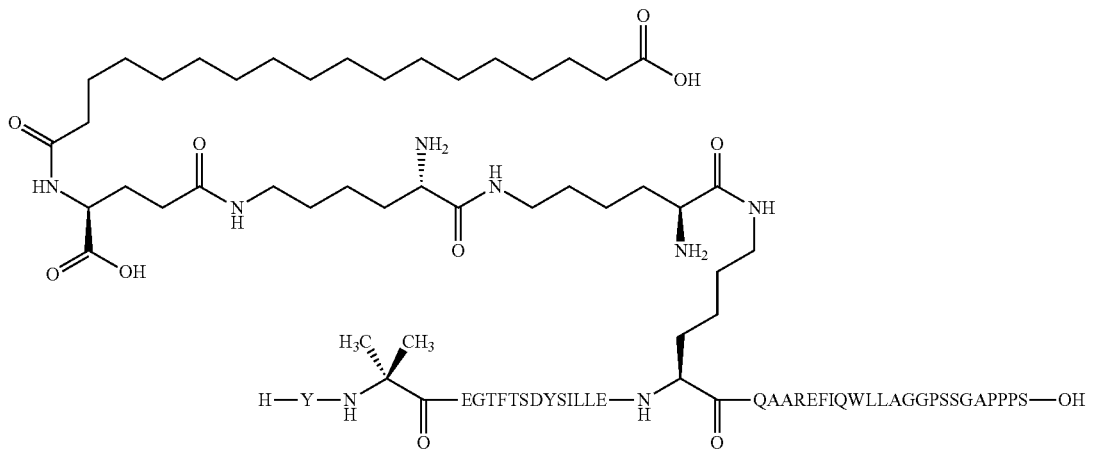

SEQ ID NO: 17; Substituent: B; Substituent position: K16
Synthesis methods: SPPS_A; SC_A; CP_A
Molecular weight (average) calculated: 4852.5 Da
LCMS_A: Rt=5.9 min; found [M+3H]$^{3+}$1618.4, [M+4H]$^{4+}$1214.1

Compound No. 24
Y-Aib-EGTFTSDYSILLE-K[(2S)-2-amino-6-[[(2S)-2-amino-6-[[(4S)-4-carboxy-4-(17-carboxyheptadecanoy-lamino)butanoyl]amino]hexanoyl]amino]hexanoyl]-QAAQEFINWLLAGGPSSGAPPPS-OH

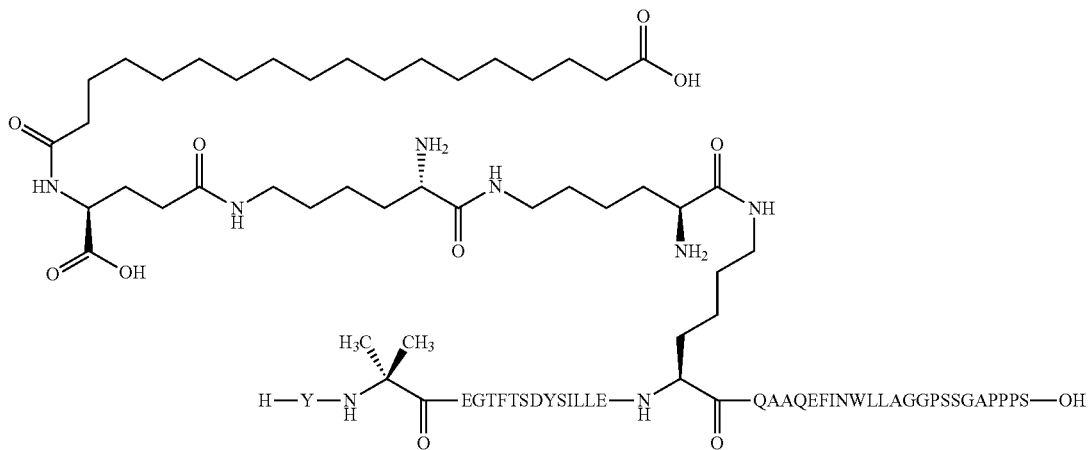

SEQ ID NO: 18; Substituent: B; Substituent position: K16
Synthesis methods: SPPS_A; SC_C; CP_A
Molecular weight (average) calculated: 4810.4 Da
LCMS_A: Rt=6.0 min; found [M+3H]$^{3+}$1604.0, [M+4H]$^{4+}$1203.4

Compound No. 25
Y-Aib-EGTFTSDYSILLE-K[(2S)-2-amino-6-[[(2S)-2-amino-6-[[(4S)-4-carboxy-4-(17-carboxyheptadecanoy-lamino)butanoyl]amino]hexanoyl]amino]hexanoyl]-QAAEEFINWLLAGGPSSGAPPPS-OH

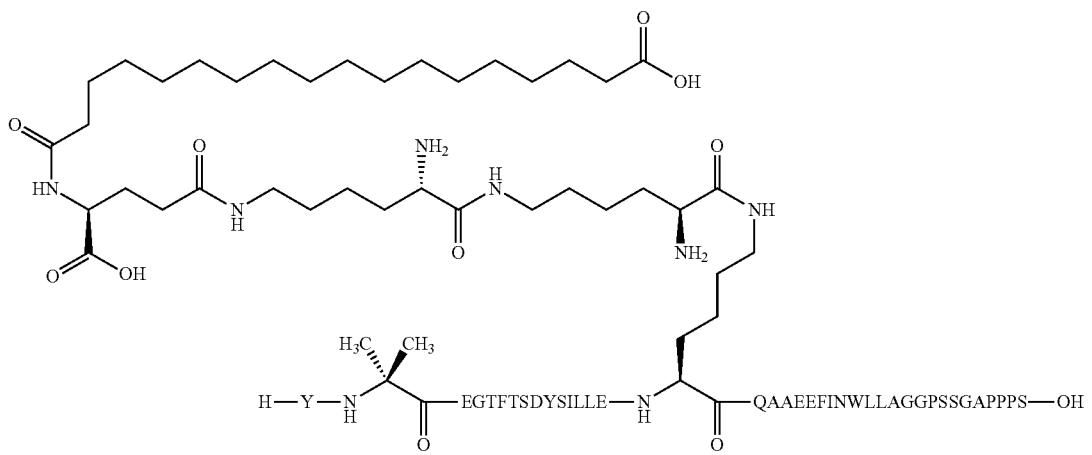

SEQ ID NO: 19; Substituent: B; Substituent position: K16
Synthesis methods: SPPS_A; SC_C; CP_A
Molecular weight (average) calculated: 4811.4 Da
LCMS_A: Rt=6.1 min; found [M+3H]$^{3+}$1604.4, [M+4H]$^{4+}$1203.6
Compound No. 26
Y-Aib-EGTFTSDYSILLE-K[(2S)-2-amino-6-[[(2S)-2-amino-6-[[(4S)-4-carboxy-4-(17-carboxyheptadecanoy-lamino)butanoyl]amino]hexanoyl]amino]hexanoyl]-QAA-HEFINWLLAGGPSSGAPPPS-OH

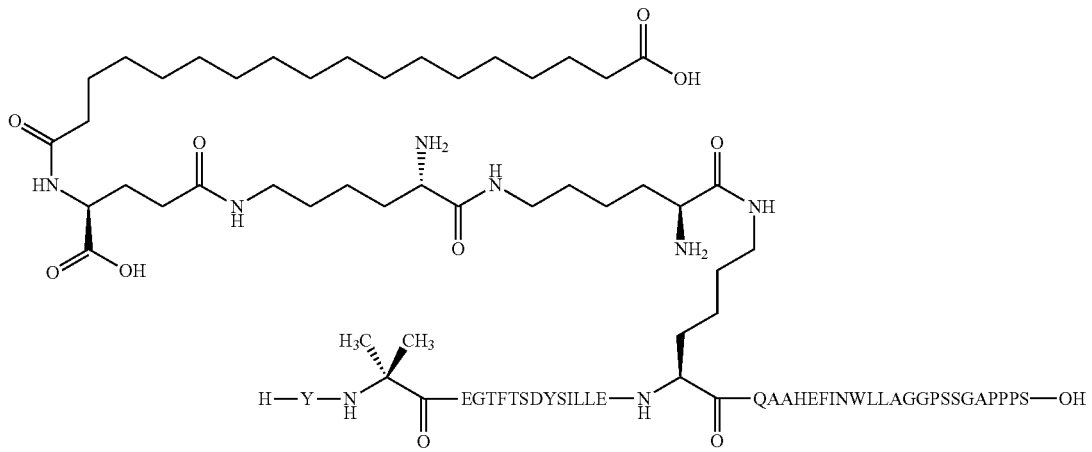

SEQ ID NO: 20; Substituent: B; Substituent position: K16
Synthesis methods: SPPS_A; SC_C; CP_A
Molecular weight (average) calculated: 4819.4 Da
LCMS_A: Rt=5.8 min; found [M+3H]$^{3+}$1607.1, [M+4H]$^{4+}$1205.5
Compound No. 27
Y-Aib-EGTFTSDYSILLE-K[(2S)-2-amino-6-[[(2S)-2-amino-6-[[(4S)-4-carboxy-4-(17-carboxyheptadecanoy-lamino)butanoyl]amino]hexanoyl]amino]hexanoyl]-QAAREFIEWLLRGGPSSGAPPPS-OH

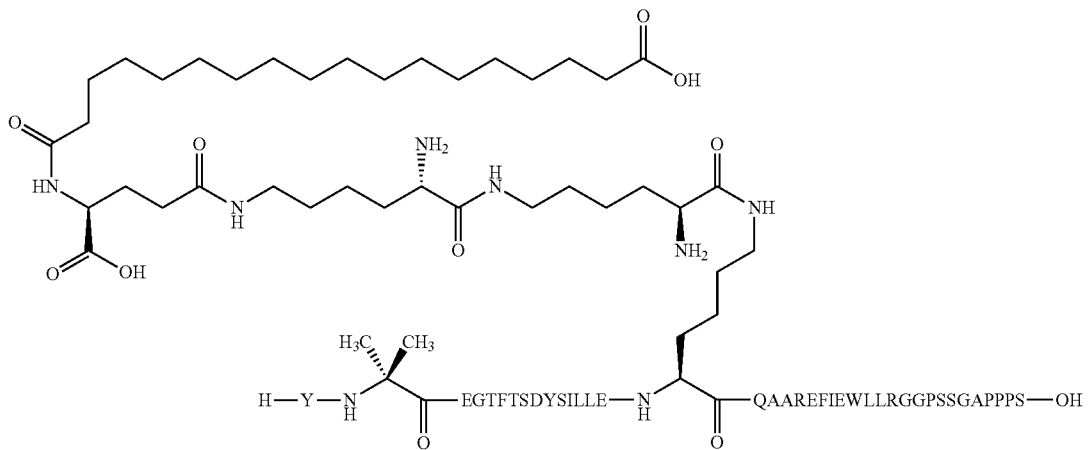

SEQ ID NO: 21; Substituent: B; Substituent position: K16
Synthesis methods: SPPS_A; SC_C; CP_A
Molecular weight (average) calculated: 4938.6 Da
LCMS_A: Rt=5.7 min; found [M+3H]$^{3+}$1646.9, [M+4H]$^{4+}$1235.4

Compound No. 28
Y-Aib-EGTFTSDYSILLE-K[(2S)-2-amino-6-[[(2S)-2-amino-6-[[(4S)-4-carboxy-4-(17-carboxyheptadecanoylamino)butanoyl]amino]hexanoyl]amino]hexanoyl]-QAAREFIEWLLRGGPESGAPPPS-OH

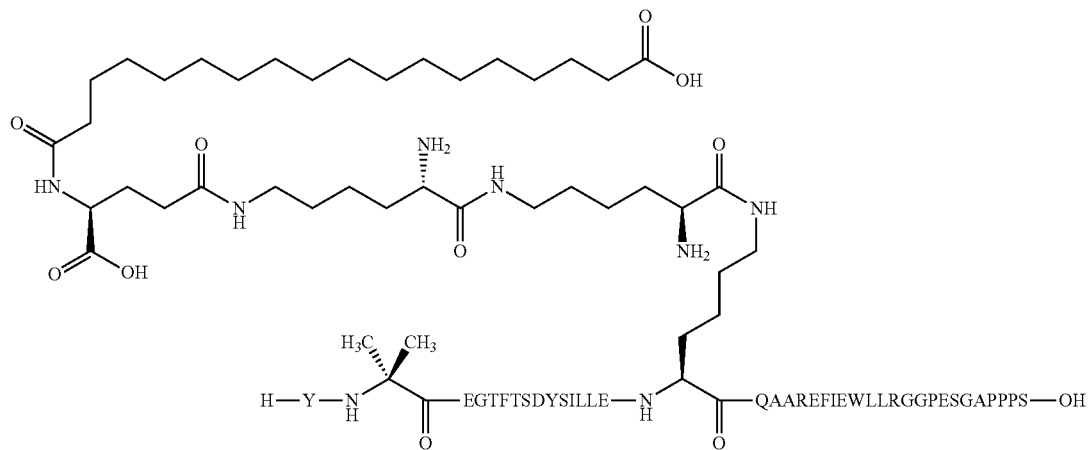

SEQ ID NO: 22; Substituent: B; Substituent position: K16
Synthesis methods: SPPS_A; SC_A; CP_A; SX_A
Molecular weight (average) calculated: 4980.6 Da
LCMS_A: Rt=5.8 min; found [M+3H]$^{3+}$1660.7, [M+4H]$^{4+}$1246.0

Compound No. 29
Y-Aib-EGTFTSDYSILLE-K[(2S)-2-amino-6-[[(2S)-2-amino-6-[[(4S)-4-carboxy-4-(17-carboxyheptadecanoylamino)butanoyl]amino]hexanoyl]amino]hexanoyl]-QAAQEFIEWLLAGGPSSGAPPPS-OH

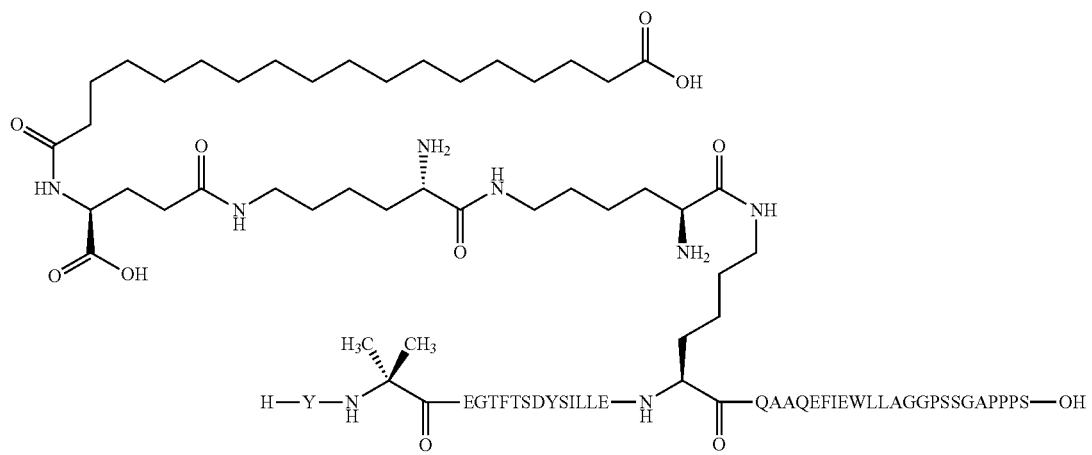

SEQ ID NO: 23; Substituent: B; Substituent position: K16
Synthesis methods: SPPS_A; SC_A; CP_A; SX_A
Molecular weight (average) calculated: 4825.4 Da
LCMS_A: Rt=6.1 min; found [M+3H]$^{3+}$1609.3, [M+4H]$^{4+}$1207.0

Compound No. 30
Y-Aib-EGTFTSDYSILLE-K[(2S)-2-amino-6-[[(2S)-2-amino-6-[[(4S)-4-carboxy-4-(17-carboxyheptadecanoylamino)butanoyl]amino]hexanoyl]amino]hexanoyl]-QAAHEFIEWLLAGGPSSGAPPPS-OH

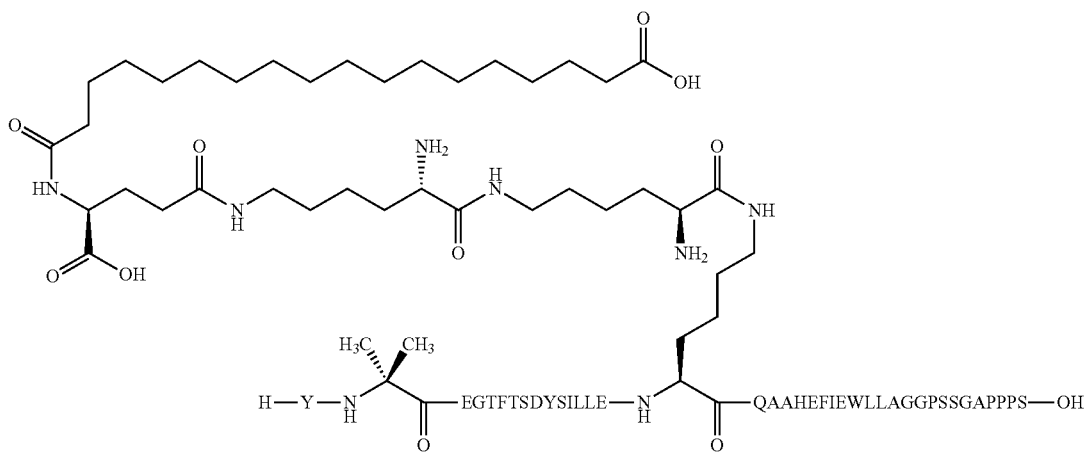

SEQ ID NO: 24; Substituent: B; Substituent position: K16
Synthesis methods: SPPS_A; SC_A; CP_A
Molecular weight (average) calculated: 4834.4 Da
LCMS_A: Rt=5.8 min; found [M+3H]$^{3+}$1612.1, [M+4H]$^{4+}$1209.3

Compound No. 31
Y-Aib-EGTFTSDYSILLE-K[(2S)-2-amino-6-[[(2S)-2-amino-6-[[(4S)-4-carboxy-4-(17-carboxyheptadecanoylamino)butanoyl]amino]hexanoyl]amino]hexanoyl]-QAAREFIEWLLAGGPSSGAPPPS-OH

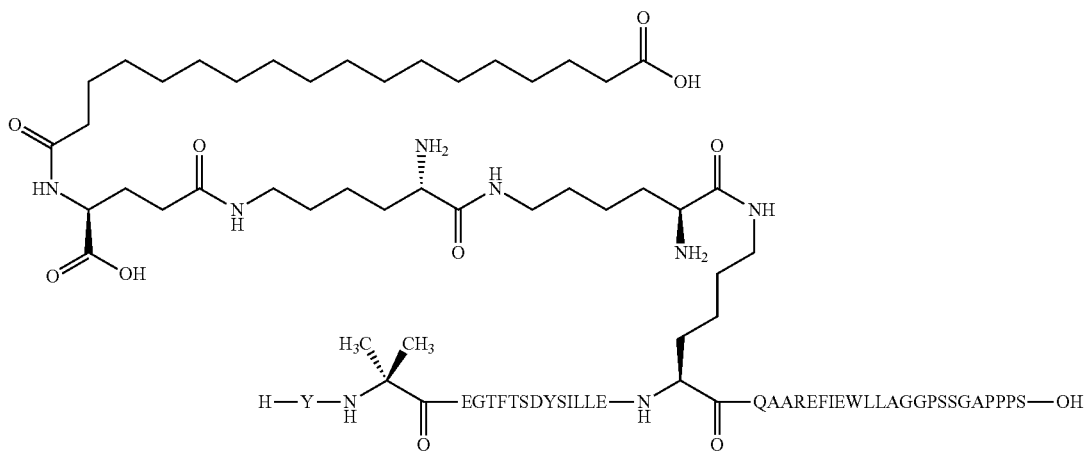

SEQ ID NO: 25; Substituent: B; Substituent position: K16
Synthesis methods: SPPS_A; SC_A; CP_A; SX_A
Molecular weight (average) calculated: 4853.5 Da
LCMS_A: Rt=5.9 min; found [M+3H]$^{3+}$1618.5, [M+4H]$^{4+}$1214.2

Compound No. 32
Y-Aib-EGTFTSDYSILLE-K[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy] acetyl]-QAAREFIEWLLAGGPSSGAPPPS-OH

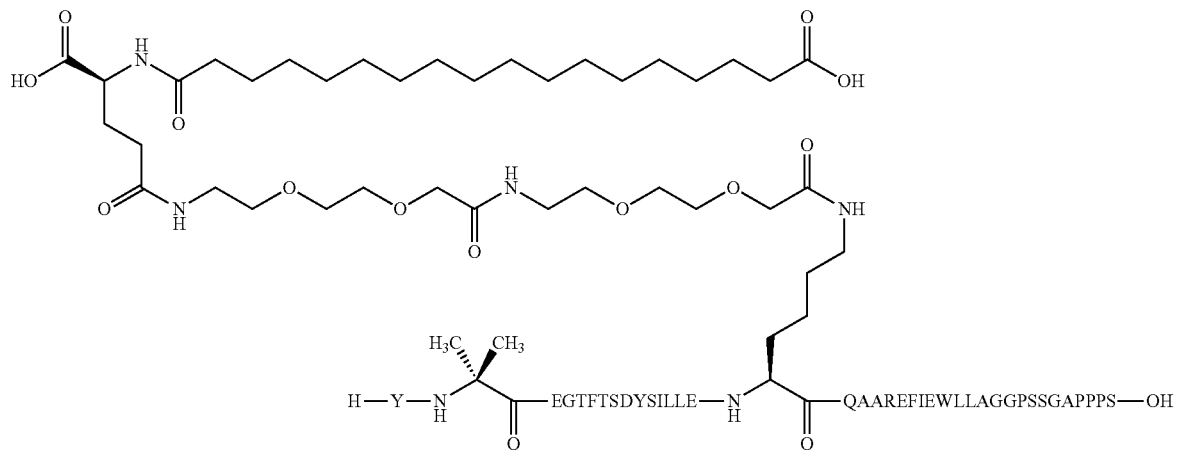

SEQ ID NO: 25; Substituent: A; Substituent position: K16
Synthesis methods: SPPS_A; SC_A; CP_A
Molecular weight (average) calculated: 4887.4 Da
LCMS_A: Rt=6.6 min; found [M+3H]$^{3+}$1629.8, [M+4H]$^{4+}$1222.8

Compound No. 33
Y-Aib-EGTVTSDYSILLE-K[(2S)-2-amino-6-[[(2S)-2-amino-6-[[(4S)-4-carboxy-4-(17-carboxyheptadecanoylamino)butanoyl]amino]hexanoyl]amino]hexanoyl]-QAAREFINWLLAGGPSSGAPPPS-OH

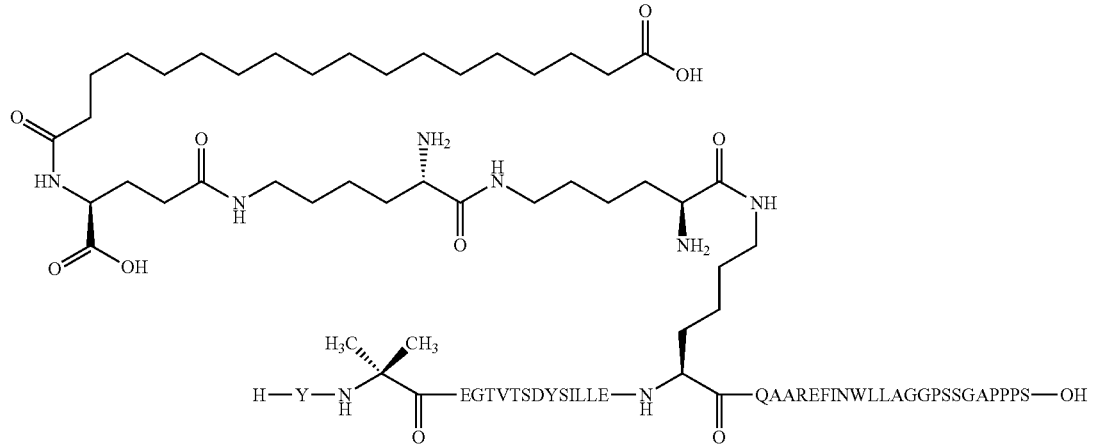

SEQ ID NO: 26; Substituent: B; Substituent position: K16
Synthesis methods: SPPS_A; SC_A; CP_A
Molecular weight (average) calculated: 4790.4 Da
LCMS_A: Rt=5.8 min; found [M+3H]$^{3+}$1597.4, [M+4H]$^{4+}$1198.3
Compound No. 34
Y-Aib-EGTFTSDYSIILE-K[(2S)-2-amino-6-[[(2S)-2-amino-6-[[(4S)-4-carboxy-4-(17-carboxyheptadecanoylamino)butanoyl]amino]hexanoyl]amino]hexanoyl]-QAAREFINWLLAGGPSSGAPPPS-OH

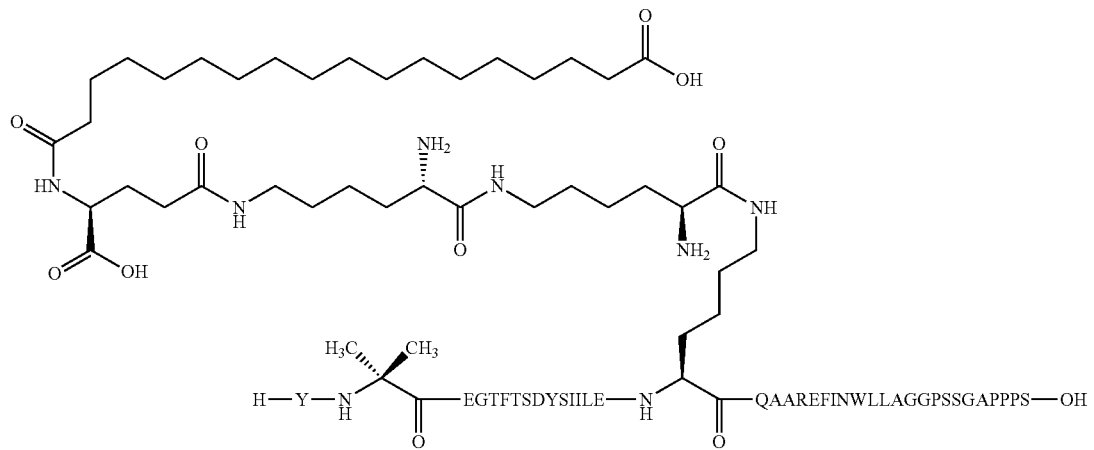

SEQ ID NO: 27; Substituent: B; Substituent position: K16
Synthesis methods: SPPS_A; SC_A; CP_A
Molecular weight (average) calculated: 4838.5 Da
LCMS_A: Rt=5.8 min; found [M+3H]$^{3+}$1613.4, [M+4H]$^{4+}$1210.3
Compound No. 35
Y-Aib-EGTFTSDYSILLE-K[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-QAAREFINWLLAGGPSSGAPPPS-OH

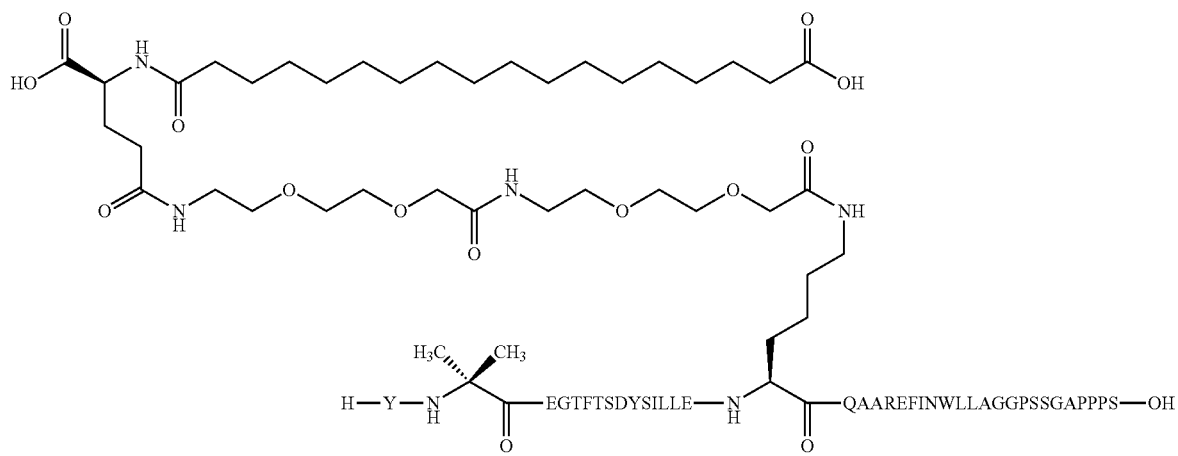

SEQ ID NO: 10; Substituent: A; Substituent position: K16
Synthesis methods: SPPS_A; SC_A; CP_A
Molecular weight (average) calculated: 4872.4 Da
LCMS_A: Rt=6.6 min; found [M+3H]$^{3+}$1624.9, [M+4H]$^{4+}$1218.9

Compound No. 36
Y-Aib-EGTFTSDYSIILE-K[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-QAAREFINWLLAGGPSSGAPPPS-OH

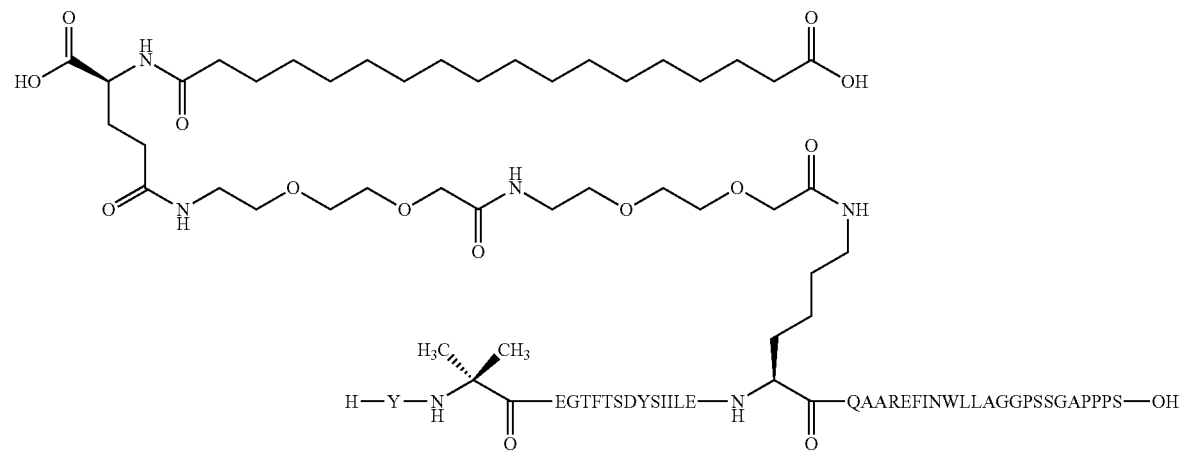

SEQ ID NO: 27; Substituent: A; Substituent position: K16
Synthesis methods: SPPS_A; SC_A; CP_A
Molecular weight (average) calculated: 4872.4 Da
LCMS_A: Rt=6.5 min; found [M+3H]$^{3+}$1624.8, [M+4H]$^{4+}$1218.9

Compound No. 37
Y-Aib-EGTFTSDYSIYLEEQAAR-K[(2S)-2-amino-6-[[(2S)-2-amino-6-[[(4S)-4-carboxy-4-(17-carboxyheptadecanoylamino)butanoyl]amino]hexanoyl]amino]hexanoyl]-FINWLLAGGPSSGAPPPS-OH

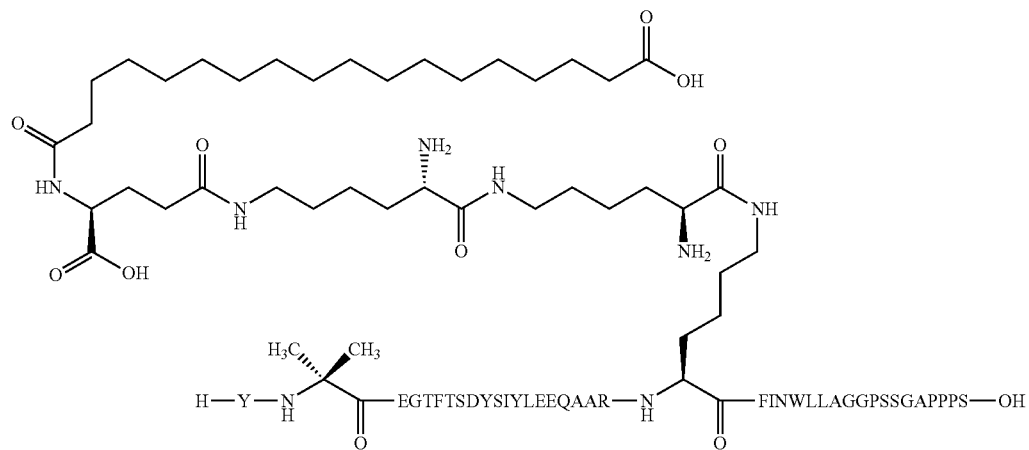

SEQ ID NO: 28; Substituent: B; Substituent position: K21
Synthesis methods: SPPS_A; SC_C; CP_A
Molecular weight (average) calculated: 4888.5 Da
LCMS_A: Rt=6.0 min; found [M+3H]$^{3+}$1630.3, [M+4H]$^{4+}$1223.0

Compound No. 38
Y-Aib-EGTFTSDYSIYLEE-K[(2S)-2-amino-6-[[(2S)-2-amino-6-[[(4S)-4-carboxy-4-(17-carboxyheptadecanoy-lamino)butanoyl]amino]hexanoyl]amino]hexanoyl]-AARE-FINWLLAGGPSSGAPPPS-OH

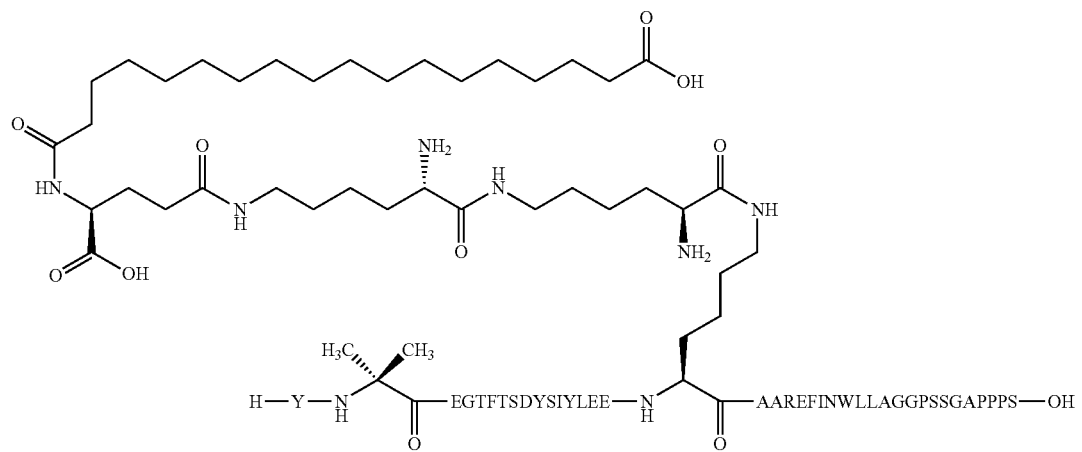

SEQ ID NO: 29; Substituent: B; Substituent position: K17
Synthesis methods: SPPS_C; SC_C; CP_A
Molecular weight (average) calculated: 4889.5 Da
LCMS_A: Rt=6.0 min; found [M+3H]$^{3+}$1630.6, [M+4H]$^{4+}$1223.2

Compound No. 39
Y-Aib-EGTFTSDYSILLEEQAAR-K[(2S)-2-amino-6-[[(2S)-2-amino-6-[[(4S)-4-carboxy-4-(17-carboxyheptade-canoylamino)butanoyl]amino]hexanoyl]amino]hexanoyl]-FINWLLAGGPSSGAPPPS-OH

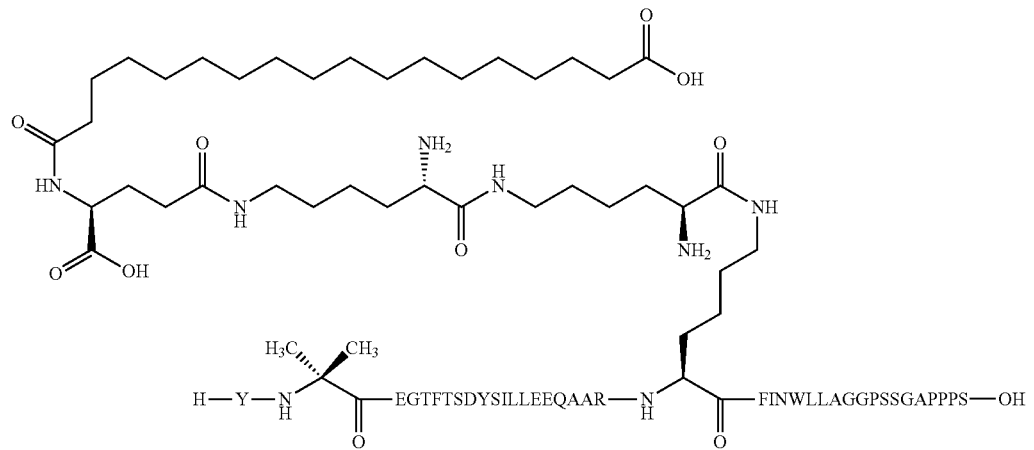

SEQ ID NO: 30; Substituent: B; Substituent position: K21
Synthesis methods: SPPS_A; SC_C; CP_A
Molecular weight (average) calculated: 4838.5 Da
LCMS_A: Rt=6.2 min; found [M+3H]$^{3+}$1613.5, [M+4H]$^{4+}$1210.4
Compound No. 40
Y-Aib-EGTFTSDYS-K[(2S)-2-amino-6-[[(2S)-2-amino-6-[[(4S)-4-carboxy-4-(17-carboxyheptadecanoylamino)butanoyl]amino]hexanoyl]amino]hexanoyl]-LLEEQAAREFIEWLLAGGPSSGAPPPS-OH

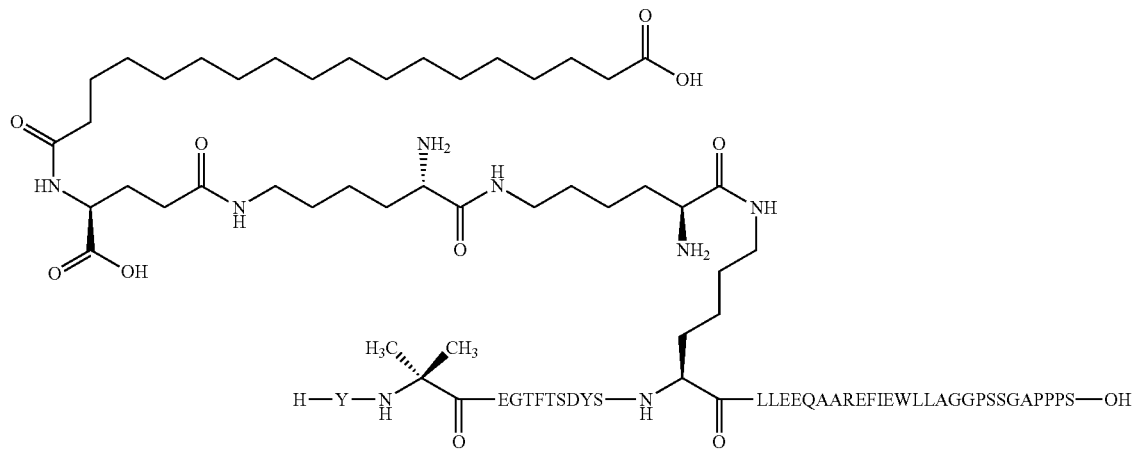

SEQ ID NO: 31; Substituent: B; Substituent position: K12
Synthesis methods: SPPS_A; SC_A; CP_A
Molecular weight (average) calculated: 4869.4 Da
LCMS_A: Rt=5.7 min; found [M+3H]$^{3+}$1623.8, [M+4H]$^{4+}$1218.2
Compound No. 41
Y-Aib-EGTFTSDYS-K[(2S)-2-amino-6-[[(2S)-2-amino-6-[[(4S)-4-carboxy-4-(17-carboxyheptadecanoylamino)butanoyl]amino]hexanoyl]amino]hexanoyl]-YLEEQAAREFINWLLAGGPSSGAPPPS-OH

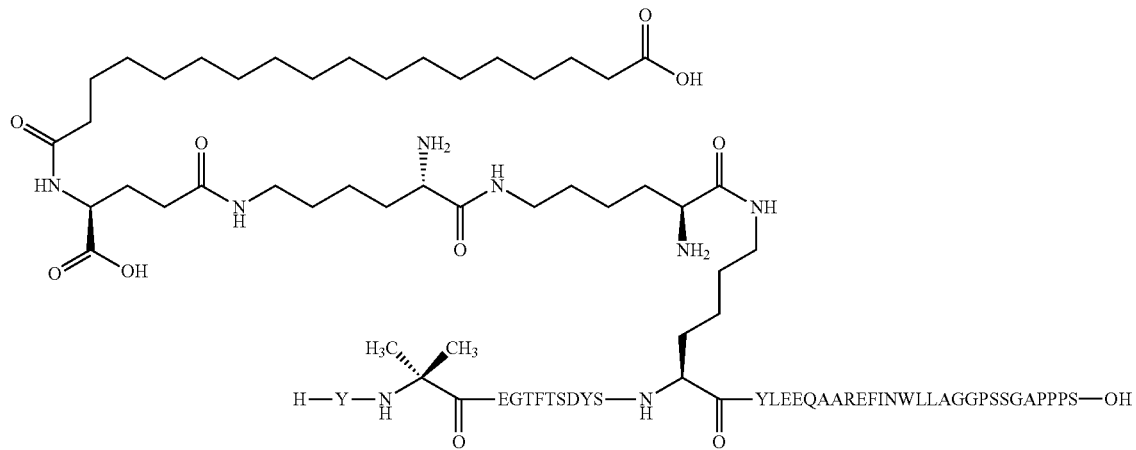

SEQ ID NO: 32; Substituent: B; Substituent position: K12
Synthesis methods: SPPS_A; SC_A; CP_A
Molecular weight (average) calculated: 4904.4 Da
LCMS_A: Rt=5.7 min; found [M+3H]$^{3+}$1635.4, [M+4H]$^{4+}$1226.7

Compound No. 42
Y-Aib-EGTFTSDYSIYLEEQAAREFINWLLAGGPS-K[(2S)-2-amino-6-[[(2S)-2-amino-6-[[(4S)-4-carboxy-4-(17-carboxyheptadecanoylamino)butanoyl]amino]hexanoyl]amino]hexanoyl]-GAPPPS-OH

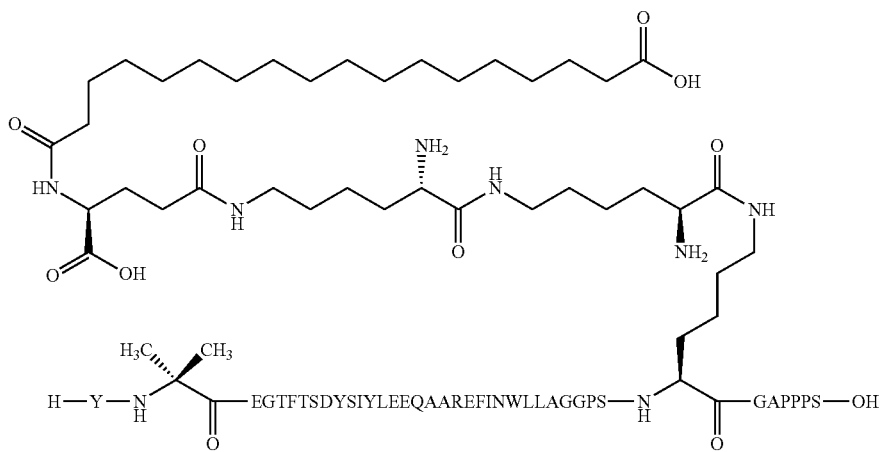

SEQ ID NO: 33; Substituent: B; Substituent position: K33
Synthesis methods: SPPS_A; SC_A; CP_A
Molecular weight (average) calculated: 4930.5 Da
LCMS_A: Rt=6.2 min; found [M+3H]$^{3+}$1644.2, [M+4H]$^{4+}$1233.4

Compound No. 43
Y-Aib-EGTFTSDYSILLEEQAAREFIEWLLAGGPS-K[(2S)-2-amino-6-[[(2S)-2-amino-6-[[(4S)-4-carboxy-4-(17-carboxyheptadecanoylamino)butanoyl]amino]hexanoyl]amino]hexanoyl]-GAPPPS-OH

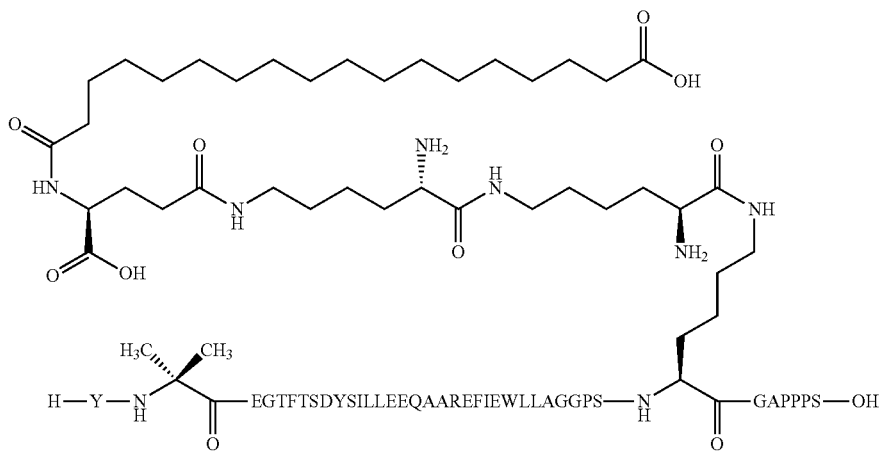

SEQ ID NO: 34; Substituent: B; Substituent position: K33
Synthesis methods: SPPS_A; SC_A; CP_A
Molecular weight (average) calculated: 4895.5 Da
LCMS_A: Rt=6.3 min; found [M+3H]$^{3+}$1632.4, [M+4H]$^{4+}$1224.6

Compound No. 44
Y-Aib-EGTFTSDYSILLEEQAAREFINWLLAGGPS-K[(2S)-2-amino-6-[[(2S)-2-amino-6-[[(4S)-4-carboxy-4-(17-carboxyheptadecanoylamino)butanoyl]amino]hexanoyl]amino]hexanoyl]-GAPPPS-OH

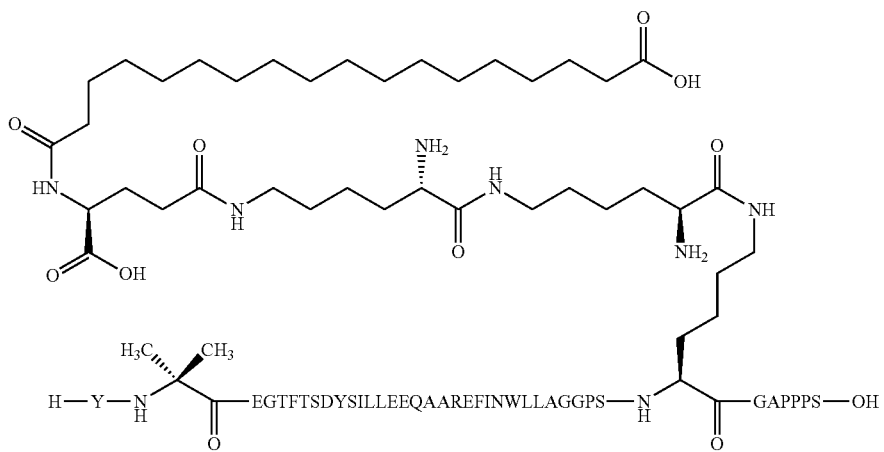

SEQ ID NO: 35; Substituent: B; Substituent position: K33
Synthesis methods: SPPS_A; SC_A; CP_A
Molecular weight (average) calculated: 4880.5 Da
LCMS_A: Rt=6.2 min; found [M+3H]$^{3+}$1627.5, [M+4H]$^{4+}$1220.9

Compound No. 45
Y-Aib-EGTFTSDYSILLEEQAAREFIEWLLAGGPS-K[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy] acetyl]-GAPPPS-OH

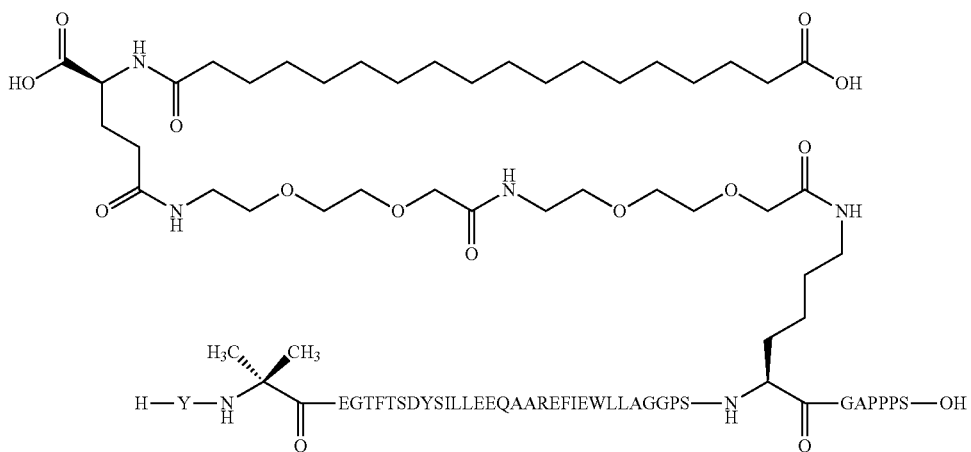

SEQ ID NO: 34; Substituent: A; Substituent position: K33
Synthesis methods: SPPS_A; SC_A; CP_A
Molecular weight (average) calculated: 4929.5 Da
LCMS_A: Rt=6.6 min; found [M+3H]$^{3+}$1643.8, [M+4H]$^{4+}$1233.1
Compound No. 46
Y-Aib-EGTFTSDYSILLEEQAAREFI EWLLAGGPS-K[(2S)-2-amino-6-[[(2S)-2-amino-6-[[(4S)-4-carboxy-4-(15-carboxypentadecanoylamino)butanoyl]amino]hexanoyl]amino]hexanoyl]-GAPPPS-OH

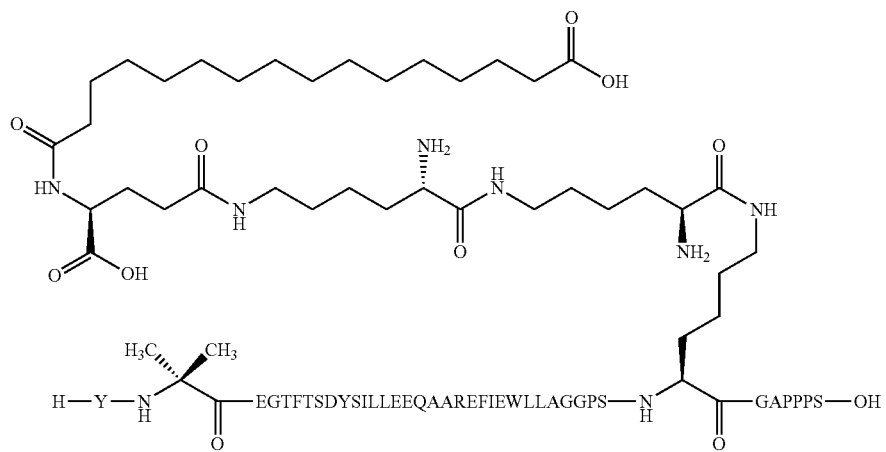

SEQ ID NO: 34; Substituent: E; Substituent position: K33
Synthesis methods: SPPS_A; SC_A; CP_A
Molecular weight (average) calculated: 4867.5 Da
LCMS_A: Rt=6.1 min; found [M+3H]$^{3+}$1623.1, [M+4H]$^{4+}$1217.6
Compound No. 47
Y-Aib-EGTFTSDYSILLEEQAAREFIEWLLAGGPS-K[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy] acetyl]-GAPPPS-OH

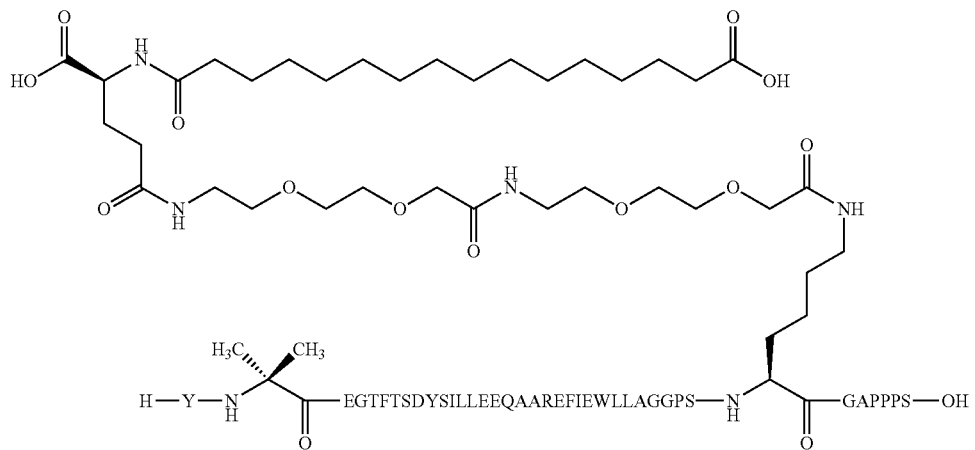

SEQ ID NO: 34; Substituent: D; Substituent position: K33

Synthesis methods: SPPS_A; SC_A; CP_A

Molecular weight (average) calculated: 4901.4 Da

LCMS_A: Rt=6.3 min; found $[M+3H]^{3+}1634.6$, $[M+4H]^{4+}1226.1$

Example 2

In Vitro Functional Potency (CRE Luciferase; Whole Cells)

The purpose of this example is to test the functional activity, or potency, of the compounds in vitro at the human GLP-1 and GIP receptors. The in vitro functional potency is the measure of target receptor activation in a whole cell assay. The potencies of derivatives of Example 1 were determined as described below. Human GLP-1(7-37) and human GIP were included in appropriate assays for comparison.

Principle

In vitro functional potency was determined by measuring the response of the target receptor in a reporter gene assay in individual cell lines. The assay was performed in stably transfected BHK cell lines that expresses one of the following G-protein coupled receptors: human GLP-1 receptor or human GIP receptor; and where each cell line contains the DNA for the cAMP response element (CRE) coupled to a promoter and the gene for firefly luciferase (CRE luciferase). When the respective receptor is activated, it results in the production of cAMP, which in turn results in expression of the luciferase protein. When assay incubation is completed, luciferase substrate (luciferin) is added resulting in the enzymatic conversion of luciferin to oxyluciferin and producing bioluminescence. The luminescence is measured as the readout for the assay.

Cell Culture and Preparation

The cells lines used in these assays were BHK cells with BHKTS13 as a parent cell line. The cell lines were derived from a clone containing the CRE luciferase element and were established by further transfection with the respective human receptor to obtain the relevant cell line: BHK CRE luc2P hGLP-1 R or BHK CRE luc2P hGIPR. The cells were cultured at 37° C. with 5% CO2 in Cell Culture Medium. They were aliquoted and stored in liquid nitrogen. The cells were kept in continuous culture and were seeded out the day before each assay.

Materials

The following chemicals were used in the assay: Pluronic F-68 10% (Gibco 2404), human serum albumin (HSA; Sigma A9511), 10% fetal bovine serum (FBS; Invitrogen 16140-071), chicken egg white ovalbumin (Sigma A5503), DMEM w/o phenol red (Gibco 21063-029), DMEM (Gibco 12430-054), 1 M Hepes (Gibco 15630), Glutamax 100× (Gibco 35050), G418 (Invitrogen 10131-027), hygromycin (Invitrogen 10687-010), and steadylite plus (PerkinElmer 6016757).

Buffers

GLP-1 R Cell Culture Medium consisted of DMEM medium with 10% FBS, 500 µg/mL G418, and 300 µg/mL hygromycin. GIPR Cell Culture Medium consisted of DMEM medium with 10% FBS, 400 µg/mL G418, and 300 µg/mL hygromycin. Assay Buffer consisted of DMEM w/o phenol red, 10 mM Hepes, 1x Glutamax. 1% ovalbumin, and 0.1% Pluronic F-68 with the addition of HSA at twice the final assay concentration. The Assay Buffer was mixed 1:1 with an equal volume of the test compound in Assay Buffer to give the final assay concentration of HSA.

Procedure

1) Cells were plated at 5000 cells/well and incubated overnight in the assay plate.
2) Cells were washed once in DPBS.
3) Stocks of the test compounds and reference compounds in concentrations ranging from 100-300 µM were diluted 1:150 in Assay Buffer. Compounds were then diluted 1:10 in column 1 of a 96 deep well dilution plate and then carried across the row creating a 3.5 fold, 12 point dilution curve.
4) Assay Buffer (50 µl aliquot) with or without HSA was added to each well in the assay plate.
5) A 50 µl aliquot of compound or blank was transferred from the dilution plate to the assay plate containing the Assay Buffer with or without HSA.
6) The assay plate was incubated for 3 h in a 5% CO2 incubator at 37° C. 7) The cells were washed once with DPBS.
8) A 100 µl aliquot of DPBS was added to each well of the assay plate.
9) A 100 µl aliquot of steadylite plus reagent (light sensitive) was added to each well of the assay plate.
10) Each assay plate was covered with aluminum foil to protect it from light and shaken at 250 RPM for 30 min at room temperature.
11) Each assay plate was read in a microtiter plate reader.

Calculations and Results

The data from the microtiter plate reader was first regressed in an Excel in order to calculate the x-axis, log scale concentrations based on the individual test compound's stock concentration and the dilutions of the assay. This data was then transferred to GraphPad Prism software for graphing and statistical analysis. The software performs a non-linear regression (log(agonist) vs response). $EC_{50}$ values which were calculated by the software and reported in pM are shown in Tables 1-3 below. A minimum of two replicates was measured for each sample. The reported values are averages of the replicates.

TABLE 1

Functional potencies at human GLP-1R and GIPR in the presence of 0% and 1% HSA.

| Compound No. | hGLP-1R, CRE Luc 0% HSA $EC_{50}$ (pM) | hGLP-1R, CRE Luc 1% HSA $EC_{50}$ (pM) | hGIPR, CRE Luc 0% HSA $EC_{50}$ (pM) | hGIPR, CRE Luc 1% HSA $EC_{50}$ (pM) |
|---|---|---|---|---|
| hGLP-1(7-37) | 8.4 | 6.7 | nd | nd |
| hGIP | nd | nd | 11.3 | 6.4 |
| 1 | 7.8 | 1659.0 | 2.8 | 172.5 |
| 2 | 6.0 | 899.7 | 3.8 | 275.4 |
| 3 | 8.5 | 626.3 | 6.9 | 229.2 |
| 4 | 6.6 | 484.3 | 8.5 | 293.8 |
| 5 | 9.4 | 624.8 | 14.2 | 362.4 |
| 6 | 3.4 | 242.7 | 18.5 | 434.0 |
| 7 | 4.2 | 513.2 | 28.7 | 686.8 |
| 8 | 2.3 | 82.1 | 6.7 | 191.1 |
| 9 | 3.8 | 278.8 | 10.8 | 508.2 |
| 10 | 3.9 | 939.9 | 11.3 | 1745.1 |
| 11 | 3.3 | 132.3 | 9.9 | 450.2 |
| 37 | 2.7 | 94.6 | 11.2 | 297.8 |
| 12 | 4.0 | 54.4 | 9.0 | 71.5 |
| 13 | 7.4 | 204.1 | 13.9 | 257.2 |
| 14 | 5.4 | 306.2 | 11.6 | 580.1 |
| 15 | 5.0 | 129.7 | 7.1 | 137.5 |
| 38 | 3.1 | 258.9 | 12.4 | 815.1 |
| 16 | 3.1 | 321.1 | 13.4 | 803.8 |
| 17 | 5.2 | 256.6 | 34.9 | 1319.0 |

TABLE 1-continued

Functional potencies at human GLP-1R and GIPR in the presence of 0% and 1% HSA.

| Compound No. | hGLP-1R, CRE Luc 0% HSA EC$_{50}$ (pM) | hGLP-1R, CRE Luc 1% HSA EC$_{50}$ (pM) | hGIPR, CRE Luc 0% HSA EC$_{50}$ (pM) | hGIPR, CRE Luc 1% HSA EC$_{50}$ (pM) |
|---|---|---|---|---|
| 18 | 19.7 | 226.2 | 20.9 | 285.1 |
| 19 | 8.6 | 364.8 | 6.5 | 275.4 |
| 20 | 4.2 | 256.0 | 7.1 | 247.4 |
| 21 | 5.7 | 118.2 | 5.4 | 130.9 |
| 22 | 2.8 | 170.5 | 6.2 | 168.9 |
| 23 | 4.1 | 117.8 | 6.7 | 134.3 |
| 24 | 12.1 | 490.2 | 3.9 | 115.1 |
| 25 | 15.5 | 740.2 | 7.2 | 263.0 |
| 26 | 7.4 | 594.6 | 4.9 | 153.0 |
| 39 | 8.2 | 135.4 | 28.4 | 365.2 |
| 27 | 4.6 | 127.0 | 6.3 | 131.8 |
| 28 | 6.2 | 139.1 | 6.6 | 86.5 |
| 29 | 16.8 | 378.5 | 3.8 | 101.7 |
| 30 | 7.3 | 267.5 | 3.2 | 185.0 |
| 41 | 1.2 | 31.4 | 4.9 | 79.3 |
| 42 | 2.3 | 83.5 | 5.9 | 305.7 |
| 40 | 6.4 | 333.6 | 9.5 | 500.6 |
| 31 | 4.2 | 202.0 | 4.7 | 188.5 |
| 32 | 5.0 | 981.9 | 7.1 | 678.7 |
| 43 | 4.0 | 359.5 | 5.6 | 444.5 |
| 44 | 4.2 | 240.9 | 5.7 | 365.3 |
| 33 | 14.8 | 360.7 | 2.9 | 102.8 |
| 34 | 6.0 | 186.4 | 8.3 | 212.8 |
| 35 | 3.0 | 412.6 | 5.2 | 303.0 |
| 36 | 4.7 | 413.8 | 5.5 | 356.5 |
| 45 | 3.9 | 1580.0 | 3.8 | 1220.0 |
| 46 | 1.5 | 110.8 | 1.8 | 97.0 |
| 47 | 2.1 | 154.5 | 3.1 | 155.7 | nd = not determined.

The compounds of the present invention display potent functional activation of the human GLP-1 R and human GIPR receptors under the given conditions. Alteration of the peptide and/or the substituent resulted in unpredictable changes in the measured potencies at each of the two receptors, as well as the ratio of potencies between the two receptors, for each compound.

Example 3

Pharmacokinetic Study in Minipigs

The purpose of this example is to determine the half-life in vivo of the derivatives of the present invention after i.v. administration to minipigs, i.e. the prolongation of their time in the body and thereby their time of action. This is done in a pharmacokinetic (PK) study, where the terminal half-life of the derivative in question is determined. By terminal half-life is generally meant the period of time it takes to halve a certain plasma concentration, measured after the initial distribution phase.

Study

Female Gottingen minipigs were obtained from Ellegaard Gottingen Minipigs (Dalmose, Denmark) approximately 7-14 months of age and weighing from approximately 16-35 kg were used in the studies. The minipigs were housed individually and fed restrictedly once daily with SDS minipig diet (Special Diets Services, Essex, UK).

After at 3 weeks of acclimatisation two permanent central venous catheters were implanted in vena cava caudalis in each animal. The animals were allowed 1 week recovery after the surgery, and were then used for repeated pharmacokinetic studies with a suitable wash-out period between successive derivative dosing.

The animals were fasted for approximately 18 hours before dosing and from 0 to 4 hours after dosing but had ad libitum access to water during the whole period.

The sodium salts of compounds of Examples 1 were dissolved to a concentration of 20-40 nmol/mL in a buffer containing 0.007% polysorbate 20, 50 mM sodium phosphate, 70 mM sodium chloride, pH 7.4. Intravenous injections (the volume corresponding to usually 1.5-2 nmol/kg, for example 0.1 mL/kg) of the compounds were given through one catheter, and blood was sampled at predefined time points for up to 14 days post dosing (preferably through the other catheter). Blood samples (for example 0.8 mL) were collected in 8 mM EDTA buffer and then centrifuged at 4° C. and 1942 g for 10 minutes.

Sampling and Analysis

Plasma was pipetted into Micronic tubes on dry ice and kept at −20° C. until analysed for plasma concentration of the compounds using ELISA, or a similar antibody-based assay, or LCMS. Individual plasma concentration-time profiles were analysed by a non-compartmental model in Phoenix WinNonLin ver. 6.4. (Pharsight Inc., Mountain View, CA, USA), and the resulting terminal half-lives (harmonic mean) determined.

Results

TABLE 2

Terminal half-life as measured after i.v. administration to minipigs

| Compound No. | t$_{1/2}$ (h) |
|---|---|
| 15 | 36 |
| 28 | 35 |
| 29 | 68 |
| 31 | 49 |

The tested compounds of the present invention have very long half-lives as compared to the half-lives of hGLP-1 and hGIP measured in man to be approximately 2-4 min and 5-7 min, respectively (Meier et al., Diabetes, 2004, 53(3): 654-662). The measured half-lives in minipigs predict half-lives in humans sufficient for at least once-weekly administration via liquid injection or at least once-daily administration via oral tablet. Unexpectedly, alterations to the peptide sequence led to appreciable differences in half-lives between co-agonists tested herein even though these co-agonists incorporate the same substituent.

Example 5

Pharmacokinetic Study in Dogs

The purpose of this example is to determine the half-life and plasma exposure in vivo of the compounds of the present invention after p.o. administration to beagle dogs, i.e. the terminal half-life and concentration of test substance that reaches circulation with time.

This is done in a pharmacokinetic (PK) study, where these parameters of the compound in question are determined. By terminal half-life is generally meant the period of time it takes to halve a certain plasma concentration, measured after the initial distribution phase.

Preparation of Tablet Compositions

Tablet compositions comprising the test substance and SNAC (sodium N-(8-(2-hydroxybenzoyl)amino)caprylate) were prepared according to methods known to the person skilled in the art by mixing test substance with roller compacted SNAC and magnesium stearate as e.g. described in WO 2019/149880. The amount of SNAC in the tablet composition was 100-300 mg, the amount of magnesium stearate in the tablet composition was 7.7 mg, and the target amount of each test substance in the tablet composition was 3-4 mg.

Animals, Dosing, and Sampling

Male beagle dogs, 1-7 years of age and weighing 9-17 kg during the study period, were included in the study. The dogs were dosed in a fasting state. The dogs were group housed in pens (12 hours light: 12 hours dark), and fed individually and restrictedly once daily with Royal Canin Medium Adult dog food (Royal Canin Products, China Branch, or Brogaarden A/S, Denmark). The dogs were used for repeated PK studies with a suitable wash-out period between successive dosing. An appropriate acclimatization period was given prior to initiation of the first PK study. All handling, dosing, and blood sampling of the animals were performed by trained and skilled staff. Before the studies, the dogs were fasted overnight and from 0 to 4 hours after dosing. The dogs were restricted to water 1 hour before dosing until 4 hours after dosing, but otherwise had ad libitum access to water during the whole period.

The compositions were administered by a single oral dosing to the dogs in groups of 6-8 dogs. The tablets were administered in the following manner: 10 min prior to tablet administration, the dogs may be dosed subcutaneously with approximately 3 nmol/kg of SEQ ID NO: 48, then tablets were placed in the back of the mouth of the dog to prevent chewing. The mouth was then closed, and 10 mL of tap water was given by syringe or gavage to facilitate swallowing of the tablet.

One blood sample was drawn before dosing, and additional samples were drawn at predefined time points after dosing for up to 240 hours, such as up to 10 hours, to adequately cover the full plasma concentration-time absorption profile of the test substance. For each blood sample time point, approximately 0.8 mL of whole blood was collected in a 1.5 mL EDTA-coated tube, which was gently turned to mix the sample with EDTA. Blood samples were collected in EDTA buffer (8 mM) and then centrifuged at 4° C. 2000 g for 10 minutes. Plasma was pipetted into Micronic tubes on dry ice, and kept at −20° C. or lower until analysis. Blood samples were taken as appropriate, for example from a venflon in the cephalic vein in the front leg for the first 2 hours and then with syringe from the jugular vein for the rest of the time points. The first few drops were allowed to drain from the venflon to avoid heparin saline from the venflon in the sample.

All blood samples were collected into test tubes containing EDTA for stabilisation and kept on ice until centrifugation. Plasma was separated from whole blood by centrifugation and the plasma was stored at −20° C. or lower until analysis.

Analysis and Calculations

The plasma was analysed for test substance using LC-MS (Liquid Chromatography-Mass Spectrometry) as known to the person skilled in the art. The system consisted of either: a Thermo Fisher QExactive mass spectrometer equipped with a 10-valve interface module TurboFlow system, CTC HTS PAL autosampler, Accela 1250 pumps, and Hot Pocket column oven; or a Thermo Fisher QExactive Plus mass spectrometer equipped with a valve interface module TurboFlow system, TriPlus RSI autosampler, Dionex UltiMate 3000 pumps, and Hot Pocket column oven. RP-HPLC separation was achieved using a linear gradient of 1:1 acetonitrile/methanol in 1% aqueous formic acid using either: a Phenomenex Onyx Monolithic C18 column (50× 2.0 mm) and a flow rate of 0.8 mL/min at 30° C.; or an Agilent Poroshell 120 SB-C18 column (50×2.1 mm, 2.7 pm) at a flow rate of 0.4 mL/min at 60° C. The mass spectrometer was operated in either positive ionization SIM mode or positive ionization PRM mode.

For each individual animal, a plasma concentration-time profile was analysed by a non-compartmental model in Pharsight Phoenix WinNonLin ver. 6.4 software or other relevant software for PK analysis, and the resulting terminal half-life ($t_{1/2}$), maximum plasma concentration per dose ($C_{max}$/D), time for maximum plasma concentration ($t_{max}$), and area under the curve to infinity per dose (AUC/D) were determined. Summary statistics of pharmacokinetic results were presented as median (for $t_{max}$), hormonic mean ($t_{1/2}$), or arithmetic mean ($C_{max}$, AUC).

Results

TABLE 3

Pharmacokinetic parameters following oral dosing of tablet compositions of test substance and SNAC to Beagle dogs.

| Compound No. | Amount of SNAC (mg) | Target amount of test substance (mg) | $T_{max}$ (h) | $t_{1/2}$ (h) | $C_{max}$/Dose (kg/L) | AUC/Dose (kg*h/L) |
|---|---|---|---|---|---|---|
| 9 | 100 | 4 | 2.0 | 50 | 0.24 | 12.1 |
| 10 | 100 | 4 | 1.0 | 36 | 0.20 | 8.4 |
| 11 | 100 | 4 | 1.4 | 34 | 0.19 | 7.1 |
| 13 | 100 | 3 | 1.5 | 60 | 0.29 | 14.8 |
| 15 | 100 | 3 | 1.5 | 59 | 0.24 | 11.9 |
| 15 | 300 | 3 | 2.0 | 46 | 0.28 | 11.6 |
| 16 | 100 | 3 | 1.3 | 47 | 0.21 | 8.6 |
| 20 | 100 | 3 | 2.0 | 56 | 0.21 | 10.8 |
| 24 | 300 | 3 | 1.8 | 74 | 0.29 | 16.4 |
| 25 | 300 | 3 | 1.8 | 43 | 0.30 | 15.2 |
| 26 | 300 | 3 | 1.2* | 70* | 0.49* | 27.4* |
| 28 | 300 | 3 | 1.3** | 67** | 0.36** | 18.6** |
| 29 | 300 | 3 | 1.2** | 69** | 0.26** | 16.6** |
| 30 | 300 | 3 | 0.8 | 81 | 0.24 | 6.5 |
| 40 | 300 | 3 | 2.0 | 61 | 0.48 | 27.0 |

TABLE 3-continued

Pharmacokinetic parameters following oral dosing of tablet compositions of test substance and SNAC to Beagle dogs.

| Compound No. | Amount of SNAC (mg) | Target amount of test substance (mg) | $T_{max}$ (h) | $t_{1/2}$ (h) | $C_{max}$/Dose (kg/L) | AUC/Dose (kg*h/L) |
|---|---|---|---|---|---|---|
| 31 | 300 | 3 | 1.3** | 56** | 0.35** | 17.9** |
| 32 | 300 | 3 | 1.8* | 80* | 0.45* | 25.3* |
| 43 | 300 | 3 | 1.5 | 131 | 0.22 | 21.4 |

*averaged data from two experiments under same formulation conditions;
**averaged data from three experiments under same formulation conditions.

The tested compounds of the present invention demonstrate oral bioavailability in this model, as concentrations of the compound in plasma were detected ($C_{max}$/D>0 and AUC/D>0) following oral administration. Furthermore, the tested compounds of the present invention further have very long half-lives as compared to the half-lives of hGLP-1 and hGIP measured in man to be approximately 2-4 min and 5-7 min, respectively (Meier et al., Diabetes, 2004, 53(3): 654-662). Alterations to the peptide sequence led to unpredictable differences in $t_{1/2}$, $C_{max}$/D and AUC/D between co-agonists even when the same substituent was incorporated.

Additionally, an unexpectedly large difference in $t_{1/2}$ was observed depending on the position of the amino acid attached to the substituent, such as eg., Compound No. 43 compared to all other compounds tested herein.

While certain features of the invention have been illustrated and described herein, many modifications, substitutions, changes, and equivalents will now occur to those of ordinary skill in the art. It is, therefore, to be understood that the appended embodiments are intended to cover all such modifications and changes as fall within the true spirit of the invention.

The invention claimed is:

1. A compound of the following structure:

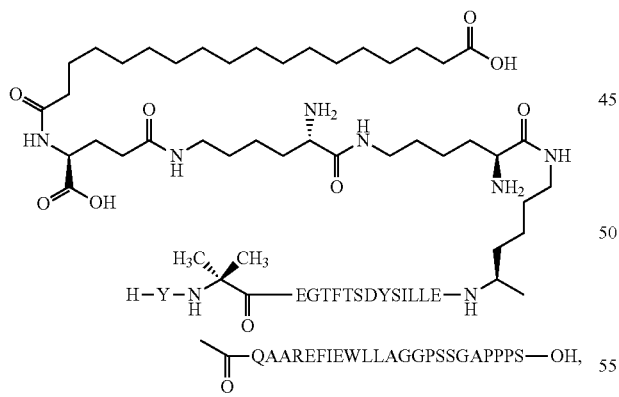

wherein the amino acid sequence of the compound is SEQ ID NO:25;
or a pharmaceutically acceptable salt thereof.

* * * * *

SEQUENCE LISTING

```
<160> NUMBER OF SEQ ID NOS: 48

<210> SEQ ID NO 1
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 1

Tyr Xaa Glu Gly Thr Phe Thr Ser Asp Tyr Ser Ile Tyr Leu Glu Lys
1               5                   10                  15

Gln Ala Ala Gln Glu Phe Val Asn Trp Leu Leu Ala Gly Gly Pro Ser
            20                  25                  30

Ser Gly Ala Pro Pro Pro Ser
        35

<210> SEQ ID NO 2
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 2

Tyr Xaa Glu Gly Thr Phe Thr Ser Asp Tyr Ser Tyr Tyr Leu Glu Lys
1               5                   10                  15

Gln Ala Ala Gln Glu Phe Val Asn Trp Leu Leu Ala Gly Gly Pro Ser
            20                  25                  30
```

Ser Gly Ala Pro Pro Pro Ser
        35

<210> SEQ ID NO 3
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 3

Tyr Xaa Glu Gly Thr Phe Thr Ser Asp Tyr Ser Tyr Leu Glu Lys
1               5                   10                  15

Gln Ala Ala Gln Ala Phe Val Asn Trp Leu Leu Ala Gly Gly Pro Ser
            20                  25                  30

Ser Gly Ala Pro Pro Pro Ser
        35

<210> SEQ ID NO 4
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 4

Tyr Xaa Glu Gly Thr Phe Thr Ser Asp Tyr Ser Ile Tyr Leu Glu Lys
1               5                   10                  15

Gln Ala Ala Arg Glu Phe Val Asn Trp Leu Leu Ala Gly Gly Pro Ser
            20                  25                  30

Ser Gly Ala Pro Pro Pro Ser
        35

<210> SEQ ID NO 5
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 5

Tyr Xaa Glu Gly Thr Phe Thr Ser Asp Tyr Ser Ile Tyr Leu Glu Lys
1               5                   10                  15

Gln Ala Ala Arg Glu Phe Ile Asn Trp Leu Leu Ala Gly Gly Pro Ser
            20                  25                  30

Ser Gly Ala Pro Pro Pro Ser
        35

<210> SEQ ID NO 6
<211> LENGTH: 39
<212> TYPE: PRT
<213> ORGANISM: Artificial Sequence
<220> FEATURE:
<223> OTHER INFORMATION: Synthetic

```
<220> FEATURE:
<221> NAME/KEY: MOD_RES
<222> LOCATION: (2)..(2)
<223> OTHER INFORMATION: Aib

<400> SEQUENCE: 6

Tyr Xaa Glu Gly Thr Phe Thr Ser Asp Tyr Ser Ile Tyr Leu Glu Lys
1               5                   10                  15

Gln Ala Ala Arg Glu Phe Ile Glu Trp Leu Leu Ala Gly Gly Pro Ser
            20                  25                  30

Ser Gly Ala Pro Pro Pro Ser
        35

<210> SEQ ID NO 7
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 7

Tyr Xaa Glu Gly Thr Phe Thr Ser Asp Tyr Ser Ile Tyr Leu Glu Lys
1               5                   10                  15

Gln Ala Ala Arg Glu Phe Ile Glu Trp Leu Leu Arg Gly Gly Pro Ser
            20                  25                  30

Ser Gly Ala Pro Pro Pro Ser
        35

<210> SEQ ID NO 8
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 8

Tyr Xaa Glu Gly Thr Phe Thr Ser Asp Tyr Ser Ile Tyr Leu Glu Lys
1               5                   10                  15

Gln Ala Ala Arg Glu Phe Ile Glu Trp Leu Leu Arg Gly Pro Glu
            20                  25                  30

Ser Gly Ala Pro Pro Pro Ser
        35

<210> SEQ ID NO 9
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 9

Tyr Xaa Glu Gly Thr Phe Thr Ser Asp Tyr Ser Ile Ala Leu Glu Lys
1               5                   10                  15
```

Gln Ala Ala Arg Glu Phe Ile Asn Trp Leu Leu Ala Gly Gly Pro Ser
            20                  25                  30

Ser Gly Ala Pro Pro Pro Ser
            35

<210> SEQ ID NO 10
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 10

Tyr Xaa Glu Gly Thr Phe Thr Ser Asp Tyr Ser Ile Leu Leu Glu Lys
1               5                   10                  15

Gln Ala Ala Arg Glu Phe Ile Asn Trp Leu Leu Ala Gly Gly Pro Ser
            20                  25                  30

Ser Gly Ala Pro Pro Pro Ser
            35

<210> SEQ ID NO 11
<211> LENGTH: 39
<212> TYPE: PRT
<213> ORGANISM: Artificial Sequence
<220> FEATURE:
<223> OTHER INFORMATION: Synthetic

<400> SEQUENCE: 11

Tyr Ala Glu Gly Thr Phe Thr Ser Asp Tyr Ser Ile Tyr Leu Glu Lys
1               5                   10                  15

Gln Ala Ala Arg Glu Phe Ile Asn Trp Leu Leu Ala Gly Gly Pro Ser
            20                  25                  30

Ser Gly Ala Pro Pro Pro Ser
            35

<210> SEQ ID NO 12
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 12

Tyr Xaa Glu Gly Thr Phe Thr Ser Asp Tyr Ser Ile Leu Leu Glu Lys
1               5                   10                  15

Gln Ala Ala Arg Glu Phe Ile Asn Trp Leu Leu Ala Gly
            20                  25

<210> SEQ ID NO 13
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 13

Tyr Xaa Glu Gly Thr Phe Thr Ser Asp Tyr Ser Ile Leu Leu Glu Lys
1               5                   10                  15

Gln Ala Ala Arg Glu Phe Ile Asn Trp Leu Leu Ala Gly Gly Pro
            20                  25                  30

<210> SEQ ID NO 14
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 14

Tyr Xaa Glu Gly Thr Phe Thr Ser Asp Tyr Ser Ile Leu Leu Glu Lys
1               5                   10                  15

Gln Ala Ala Arg Glu Phe Ile Asn Trp Leu Leu Ala Gly Gly Pro Ser
            20                  25                  30

Ser

<210> SEQ ID NO 15
<211> LENGTH: 35
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 15

Tyr Xaa Glu Gly Thr Phe Thr Ser Asp Tyr Ser Ile Leu Leu Glu Lys
1               5                   10                  15

Gln Ala Ala Arg Glu Phe Ile Asn Trp Leu Leu Ala Gly Gly Pro Ser
            20                  25                  30

Ser Gly Ala
        35

<210> SEQ ID NO 16
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 16

Tyr Xaa Glu Gly Thr Phe Thr Ser Asp Tyr Ser Ile Leu Leu Glu Lys
1               5                   10                  15

Gln Ala Ala Arg Glu Phe Val Asn Trp Leu Leu Ala Gly Gly Pro Ser
            20                  25                  30

Ser Gly Ala Pro Pro Ser
        35

<210> SEQ ID NO 17

```
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 17

Tyr Xaa Glu Gly Thr Phe Thr Ser Asp Tyr Ser Ile Leu Leu Glu Lys
 1               5                  10                  15

Gln Ala Ala Arg Glu Phe Ile Gln Trp Leu Leu Ala Gly Gly Pro Ser
             20                  25                  30

Ser Gly Ala Pro Pro Pro Ser
         35

<210> SEQ ID NO 18
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 18

Tyr Xaa Glu Gly Thr Phe Thr Ser Asp Tyr Ser Ile Leu Leu Glu Lys
 1               5                  10                  15

Gln Ala Ala Gln Glu Phe Ile Asn Trp Leu Leu Ala Gly Gly Pro Ser
             20                  25                  30

Ser Gly Ala Pro Pro Pro Ser
         35

<210> SEQ ID NO 19
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 19

Tyr Xaa Glu Gly Thr Phe Thr Ser Asp Tyr Ser Ile Leu Leu Glu Lys
 1               5                  10                  15

Gln Ala Ala Glu Glu Phe Ile Asn Trp Leu Leu Ala Gly Gly Pro Ser
             20                  25                  30

Ser Gly Ala Pro Pro Pro Ser
         35

<210> SEQ ID NO 20
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib
```

-continued

<400> SEQUENCE: 20

Tyr Xaa Glu Gly Thr Phe Thr Ser Asp Tyr Ser Ile Leu Leu Glu Lys
1               5                   10                  15

Gln Ala Ala His Glu Phe Ile Asn Trp Leu Leu Ala Gly Gly Pro Ser
            20                  25                  30

Ser Gly Ala Pro Pro Pro Ser
            35

<210> SEQ ID NO 21
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 21

Tyr Xaa Glu Gly Thr Phe Thr Ser Asp Tyr Ser Ile Leu Leu Glu Lys
1               5                   10                  15

Gln Ala Ala Arg Glu Phe Ile Glu Trp Leu Leu Arg Gly Gly Pro Ser
            20                  25                  30

Ser Gly Ala Pro Pro Pro Ser
            35

<210> SEQ ID NO 22
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 22

Tyr Xaa Glu Gly Thr Phe Thr Ser Asp Tyr Ser Ile Leu Leu Glu Lys
1               5                   10                  15

Gln Ala Ala Arg Glu Phe Ile Glu Trp Leu Leu Arg Gly Gly Pro Glu
            20                  25                  30

Ser Gly Ala Pro Pro Pro Ser
            35

<210> SEQ ID NO 23
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 23

Tyr Xaa Glu Gly Thr Phe Thr Ser Asp Tyr Ser Ile Leu Leu Glu Lys
1               5                   10                  15

Gln Ala Ala Gln Glu Phe Ile Glu Trp Leu Leu Ala Gly Gly Pro Ser
            20                  25                  30

Ser Gly Ala Pro Pro Pro Ser
            35

```
<210> SEQ ID NO 24
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 24

Tyr Xaa Glu Gly Thr Phe Thr Ser Asp Tyr Ser Ile Leu Leu Glu Lys
1               5                   10                  15

Gln Ala Ala His Glu Phe Ile Glu Trp Leu Leu Ala Gly Gly Pro Ser
            20                  25                  30

Ser Gly Ala Pro Pro Pro Ser
        35

<210> SEQ ID NO 25
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 25

Tyr Xaa Glu Gly Thr Phe Thr Ser Asp Tyr Ser Ile Leu Leu Glu Lys
1               5                   10                  15

Gln Ala Ala Arg Glu Phe Ile Glu Trp Leu Leu Ala Gly Gly Pro Ser
            20                  25                  30

Ser Gly Ala Pro Pro Pro Ser
        35

<210> SEQ ID NO 26
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 26

Tyr Xaa Glu Gly Thr Val Thr Ser Asp Tyr Ser Ile Leu Leu Glu Lys
1               5                   10                  15

Gln Ala Ala Arg Glu Phe Ile Asn Trp Leu Leu Ala Gly Gly Pro Ser
            20                  25                  30

Ser Gly Ala Pro Pro Pro Ser
        35

<210> SEQ ID NO 27
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
```

```
<222> LOCATION: (2)..(2)
<223> OTHER INFORMATION: Aib

<400> SEQUENCE: 27

Tyr Xaa Glu Gly Thr Phe Thr Ser Asp Tyr Ser Ile Ile Leu Glu Lys
1               5                   10                  15

Gln Ala Ala Arg Glu Phe Ile Asn Trp Leu Leu Ala Gly Gly Pro Ser
            20                  25                  30

Ser Gly Ala Pro Pro Pro Ser
            35

<210> SEQ ID NO 28
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 28

Tyr Xaa Glu Gly Thr Phe Thr Ser Asp Tyr Ser Ile Tyr Leu Glu Glu
1               5                   10                  15

Gln Ala Ala Arg Lys Phe Ile Asn Trp Leu Leu Ala Gly Gly Pro Ser
            20                  25                  30

Ser Gly Ala Pro Pro Pro Ser
            35

<210> SEQ ID NO 29
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 29

Tyr Xaa Glu Gly Thr Phe Thr Ser Asp Tyr Ser Ile Tyr Leu Glu Glu
1               5                   10                  15

Lys Ala Ala Arg Glu Phe Ile Asn Trp Leu Leu Ala Gly Gly Pro Ser
            20                  25                  30

Ser Gly Ala Pro Pro Pro Ser
            35

<210> SEQ ID NO 30
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 30

Tyr Xaa Glu Gly Thr Phe Thr Ser Asp Tyr Ser Ile Leu Leu Glu Glu
1               5                   10                  15

Gln Ala Ala Arg Lys Phe Ile Asn Trp Leu Leu Ala Gly Gly Pro Ser
            20                  25                  30
```

```
Ser Gly Ala Pro Pro Ser
        35

<210> SEQ ID NO 31
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 31

Tyr Xaa Glu Gly Thr Phe Thr Ser Asp Tyr Ser Lys Leu Leu Glu Glu
1               5                   10                  15

Gln Ala Ala Arg Glu Phe Ile Glu Trp Leu Leu Ala Gly Gly Pro Ser
            20                  25                  30

Ser Gly Ala Pro Pro Ser
        35

<210> SEQ ID NO 32
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 32

Tyr Xaa Glu Gly Thr Phe Thr Ser Asp Tyr Ser Lys Tyr Leu Glu Glu
1               5                   10                  15

Gln Ala Ala Arg Glu Phe Ile Asn Trp Leu Leu Ala Gly Gly Pro Ser
            20                  25                  30

Ser Gly Ala Pro Pro Ser
        35

<210> SEQ ID NO 33
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 33

Tyr Xaa Glu Gly Thr Phe Thr Ser Asp Tyr Ser Ile Tyr Leu Glu Glu
1               5                   10                  15

Gln Ala Ala Arg Glu Phe Ile Asn Trp Leu Leu Ala Gly Gly Pro Ser
            20                  25                  30

Lys Gly Ala Pro Pro Ser
        35

<210> SEQ ID NO 34
<211> LENGTH: 39
<212> TYPE: PRT
<213> ORGANISM: Artificial Sequence
<220> FEATURE:
```

```
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 34

Tyr Xaa Glu Gly Thr Phe Thr Ser Asp Tyr Ser Ile Leu Leu Glu Glu
1               5                   10                  15

Gln Ala Ala Arg Glu Phe Ile Glu Trp Leu Leu Ala Gly Gly Pro Ser
            20                  25                  30

Lys Gly Ala Pro Pro Pro Ser
        35

<210> SEQ ID NO 35
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 35

Tyr Xaa Glu Gly Thr Phe Thr Ser Asp Tyr Ser Ile Leu Leu Glu Glu
1               5                   10                  15

Gln Ala Ala Arg Glu Phe Ile Asn Trp Leu Leu Ala Gly Gly Pro Ser
            20                  25                  30

Lys Gly Ala Pro Pro Pro Ser
        35

<210> SEQ ID NO 36
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is Aib or Ala
<220> FEATURE:
<221> NAME/KEY: MISC_FEATURE
<222> LOCATION: (6)..(6)
<223> OTHER INFORMATION: Xaa is Phe or Val
<220> FEATURE:
<221> NAME/KEY: MISC_FEATURE
<222> LOCATION: (12)..(12)
<223> OTHER INFORMATION: Xaa is Ile or Tyr
<220> FEATURE:
<221> NAME/KEY: MISC_FEATURE
<222> LOCATION: (13)..(13)
<223> OTHER INFORMATION: Xaa is Tyr, Ala, Leu or Ile
<220> FEATURE:
<221> NAME/KEY: MISC_FEATURE
<222> LOCATION: (16)..(16)
<223> OTHER INFORMATION: Xaa is Lys or Glu
<220> FEATURE:
<221> NAME/KEY: MISC_FEATURE
<222> LOCATION: (20)..(20)
<223> OTHER INFORMATION: Xaa is Gln, Arg, Glu or His
<220> FEATURE:
<221> NAME/KEY: MISC_FEATURE
<222> LOCATION: (21)..(21)
<223> OTHER INFORMATION: Xaa is Ala or Glu
<220> FEATURE:
<221> NAME/KEY: MISC_FEATURE
<222> LOCATION: (23)..(23)
<223> OTHER INFORMATION: Xaa is Ile or Val
```

-continued

```
<220> FEATURE:
<221> NAME/KEY: MISC_FEATURE
<222> LOCATION: (24)..(24)
<223> OTHER INFORMATION: Xaa is Glu, Gln or Asn
<220> FEATURE:
<221> NAME/KEY: MISC_FEATURE
<222> LOCATION: (28)..(28)
<223> OTHER INFORMATION: Xaa is Ala or Arg
<220> FEATURE:
<221> NAME/KEY: MISC_FEATURE
<222> LOCATION: (32)..(32)
<223> OTHER INFORMATION: Xaa is Glu, Ser or absent
<220> FEATURE:
<221> NAME/KEY: MISC_FEATURE
<222> LOCATION: (33)..(33)
<223> OTHER INFORMATION: Xaa is Ser, Lys or absent
<220> FEATURE:
<221> NAME/KEY: MISC_FEATURE
<222> LOCATION: (34)..(34)
<223> OTHER INFORMATION: Xaa is Gly or absent
<220> FEATURE:
<221> NAME/KEY: MISC_FEATURE
<222> LOCATION: (35)..(35)
<223> OTHER INFORMATION: Xaa is Ala or absent
<220> FEATURE:
<221> NAME/KEY: MISC_FEATURE
<222> LOCATION: (36)..(36)
<223> OTHER INFORMATION: Xaa is Pro or absent
<220> FEATURE:
<221> NAME/KEY: MISC_FEATURE
<222> LOCATION: (37)..(37)
<223> OTHER INFORMATION: Xaa is Pro or absent
<220> FEATURE:
<221> NAME/KEY: MISC_FEATURE
<222> LOCATION: (38)..(38)
<223> OTHER INFORMATION: Xaa is Pro or absent
<220> FEATURE:
<221> NAME/KEY: MISC_FEATURE
<222> LOCATION: (39)..(39)
<223> OTHER INFORMATION: Xaa is Ser or absent

<400> SEQUENCE: 36

Tyr Xaa Glu Gly Thr Xaa Thr Ser Asp Tyr Ser Xaa Xaa Leu Glu Xaa
1               5                   10                  15

Gln Ala Ala Xaa Xaa Phe Xaa Xaa Trp Leu Leu Xaa Gly Gly Pro Xaa
                20                  25                  30

Xaa Xaa Xaa Xaa Xaa Xaa Xaa
            35

<210> SEQ ID NO 37
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is Aib or Ala
<220> FEATURE:
<221> NAME/KEY: MISC_FEATURE
<222> LOCATION: (6)..(6)
<223> OTHER INFORMATION: Xaa is Phe or Val
<220> FEATURE:
<221> NAME/KEY: MISC_FEATURE
<222> LOCATION: (12)..(12)
<223> OTHER INFORMATION: Xaa is Ile or Tyr
<220> FEATURE:
<221> NAME/KEY: MISC_FEATURE
<222> LOCATION: (13)..(13)
<223> OTHER INFORMATION: Xaa is Tyr, Ala, Leu or Ile
<220> FEATURE:
<221> NAME/KEY: MISC_FEATURE
<222> LOCATION: (16)..(16)
<223> OTHER INFORMATION: Xaa is Lys or Glu
```

```
<220> FEATURE:
<221> NAME/KEY: MISC_FEATURE
<222> LOCATION: (20)..(20)
<223> OTHER INFORMATION: Xaa is Gln, Arg, Glu or His
<220> FEATURE:
<221> NAME/KEY: MISC_FEATURE
<222> LOCATION: (21)..(21)
<223> OTHER INFORMATION: Xaa is Ala or Glu
<220> FEATURE:
<221> NAME/KEY: MISC_FEATURE
<222> LOCATION: (23)..(23)
<223> OTHER INFORMATION: Xaa is Ile or Val
<220> FEATURE:
<221> NAME/KEY: MISC_FEATURE
<222> LOCATION: (24)..(24)
<223> OTHER INFORMATION: Xaa is Glu, Gln or Asn
<220> FEATURE:
<221> NAME/KEY: MISC_FEATURE
<222> LOCATION: (28)..(28)
<223> OTHER INFORMATION: Xaa is Ala or Arg

<400> SEQUENCE: 37

Tyr Xaa Glu Gly Thr Xaa Thr Ser Asp Tyr Ser Xaa Xaa Leu Glu Xaa
 1               5                  10                  15

Gln Ala Ala Xaa Xaa Phe Xaa Xaa Trp Leu Leu Xaa Gly Gly Pro Ser
            20                  25                  30

Ser Gly Ala Pro Pro Ser
        35

<210> SEQ ID NO 38
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is Aib or Ala
<220> FEATURE:
<221> NAME/KEY: MISC_FEATURE
<222> LOCATION: (6)..(6)
<223> OTHER INFORMATION: Xaa is Phe or Val
<220> FEATURE:
<221> NAME/KEY: MISC_FEATURE
<222> LOCATION: (12)..(12)
<223> OTHER INFORMATION: Xaa is Ile or Tyr
<220> FEATURE:
<221> NAME/KEY: MISC_FEATURE
<222> LOCATION: (13)..(13)
<223> OTHER INFORMATION: Xaa is Tyr, Ala, Leu or Ile
<220> FEATURE:
<221> NAME/KEY: MISC_FEATURE
<222> LOCATION: (16)..(16)
<223> OTHER INFORMATION: Xaa is Lys or Glu
<220> FEATURE:
<221> NAME/KEY: MISC_FEATURE
<222> LOCATION: (20)..(20)
<223> OTHER INFORMATION: Xaa is Gln, Arg, Glu or His
<220> FEATURE:
<221> NAME/KEY: MISC_FEATURE
<222> LOCATION: (21)..(21)
<223> OTHER INFORMATION: Xaa is Ala or Glu
<220> FEATURE:
<221> NAME/KEY: MISC_FEATURE
<222> LOCATION: (23)..(23)
<223> OTHER INFORMATION: Xaa is Ile or Val
<220> FEATURE:
<221> NAME/KEY: MISC_FEATURE
<222> LOCATION: (24)..(24)
<223> OTHER INFORMATION: Xaa is Glu, Gln or Asn
<220> FEATURE:
<221> NAME/KEY: MISC_FEATURE
<222> LOCATION: (28)..(28)
<223> OTHER INFORMATION: Xaa is Ala or Arg
```

```
<400> SEQUENCE: 38

Tyr Xaa Glu Gly Thr Xaa Thr Ser Asp Tyr Ser Xaa Xaa Leu Glu Xaa
1               5                   10                  15

Gln Ala Ala Xaa Xaa Phe Xaa Xaa Trp Leu Leu Xaa Gly Gly Pro Glu
            20                  25                  30

Ser Gly Ala Pro Pro Ser
        35

<210> SEQ ID NO 39
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is Aib or Ala
<220> FEATURE:
<221> NAME/KEY: MISC_FEATURE
<222> LOCATION: (6)..(6)
<223> OTHER INFORMATION: Xaa is Phe or Val
<220> FEATURE:
<221> NAME/KEY: MISC_FEATURE
<222> LOCATION: (12)..(12)
<223> OTHER INFORMATION: Xaa is Ile or Tyr
<220> FEATURE:
<221> NAME/KEY: MISC_FEATURE
<222> LOCATION: (13)..(13)
<223> OTHER INFORMATION: Xaa is Tyr, Ala, Leu or Ile
<220> FEATURE:
<221> NAME/KEY: MISC_FEATURE
<222> LOCATION: (16)..(16)
<223> OTHER INFORMATION: Xaa is Lys or Glu
<220> FEATURE:
<221> NAME/KEY: MISC_FEATURE
<222> LOCATION: (20)..(20)
<223> OTHER INFORMATION: Xaa is Gln, Arg, Glu or His
<220> FEATURE:
<221> NAME/KEY: MISC_FEATURE
<222> LOCATION: (21)..(21)
<223> OTHER INFORMATION: Xaa is Ala or Glu
<220> FEATURE:
<221> NAME/KEY: MISC_FEATURE
<222> LOCATION: (23)..(23)
<223> OTHER INFORMATION: Xaa is Ile or Val
<220> FEATURE:
<221> NAME/KEY: MISC_FEATURE
<222> LOCATION: (24)..(24)
<223> OTHER INFORMATION: Xaa is Glu, Gln or Asn
<220> FEATURE:
<221> NAME/KEY: MISC_FEATURE
<222> LOCATION: (28)..(28)
<223> OTHER INFORMATION: Xaa is Ala or Arg

<400> SEQUENCE: 39

Tyr Xaa Glu Gly Thr Xaa Thr Ser Asp Tyr Ser Xaa Xaa Leu Glu Xaa
1               5                   10                  15

Gln Ala Ala Xaa Xaa Phe Xaa Xaa Trp Leu Leu Xaa Gly Gly Pro Ser
            20                  25                  30

Lys Gly Ala Pro Pro Ser
        35

<210> SEQ ID NO 40
<211> LENGTH: 4
<212> TYPE: PRT
<213> ORGANISM: Artificial Sequence
<220> FEATURE:
<223> OTHER INFORMATION: Synthetic
```

```
<400> SEQUENCE: 40

Ser Ser Gly Ala
1

<210> SEQ ID NO 41
<211> LENGTH: 4
<212> TYPE: PRT
<213> ORGANISM: Artificial Sequence
<220> FEATURE:
<223> OTHER INFORMATION: Synthetic

<400> SEQUENCE: 41

Glu Ser Gly Ala
1

<210> SEQ ID NO 42
<211> LENGTH: 4
<212> TYPE: PRT
<213> ORGANISM: Artificial Sequence
<220> FEATURE:
<223> OTHER INFORMATION: Synthetic

<400> SEQUENCE: 42

Ser Lys Gly Ala
1

<210> SEQ ID NO 43
<211> LENGTH: 12
<212> TYPE: PRT
<213> ORGANISM: Artificial Sequence
<220> FEATURE:
<223> OTHER INFORMATION: Synthetic

<400> SEQUENCE: 43

Leu Leu Glu Lys Gln Ala Ala Arg Glu Phe Ile Asn
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Synthetic

<400> SEQUENCE: 44

Leu Leu Glu Lys Gln Ala Ala Arg Glu Phe Ile Glu
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Synthetic

<400> SEQUENCE: 45

Leu Leu Glu Lys Gln Ala Ala Gln Glu Phe Ile Glu
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Synthetic

<400> SEQUENCE: 46
```

Leu Leu Glu Glu Gln Ala Ala Arg Glu Phe Ile Glu
1               5                   10

<210> SEQ ID NO 47
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (2)..(2)
<223> OTHER INFORMATION: Xaa is Aib or Ala
<220> FEATURE:
<221> NAME/KEY: MISC_FEATURE
<222> LOCATION: (6)..(6)
<223> OTHER INFORMATION: Xaa is Phe or Val
<220> FEATURE:
<221> NAME/KEY: MISC_FEATURE
<222> LOCATION: (12)..(12)
<223> OTHER INFORMATION: Xaa is Ile or Tyr
<220> FEATURE:
<221> NAME/KEY: MISC_FEATURE
<222> LOCATION: (13)..(13)
<223> OTHER INFORMATION: Xaa is Tyr, Ala, Leu or Ile
<220> FEATURE:
<221> NAME/KEY: MISC_FEATURE
<222> LOCATION: (16)..(16)
<223> OTHER INFORMATION: Xaa is Lys or Glu
<220> FEATURE:
<221> NAME/KEY: MISC_FEATURE
<222> LOCATION: (20)..(20)
<223> OTHER INFORMATION: Xaa is Gln, Arg, Glu or His
<220> FEATURE:
<221> NAME/KEY: MISC_FEATURE
<222> LOCATION: (21)..(21)
<223> OTHER INFORMATION: Xaa is Ala or Glu
<220> FEATURE:
<221> NAME/KEY: MISC_FEATURE
<222> LOCATION: (23)..(23)
<223> OTHER INFORMATION: Xaa is Ile or Val
<220> FEATURE:
<221> NAME/KEY: MISC_FEATURE
<222> LOCATION: (24)..(24)
<223> OTHER INFORMATION: Xaa is Glu, Gln or Asn
<220> FEATURE:
<221> NAME/KEY: MISC_FEATURE
<222> LOCATION: (28)..(28)
<223> OTHER INFORMATION: Xaa is Ala or Arg
<220> FEATURE:
<221> NAME/KEY: MISC_FEATURE
<222> LOCATION: (30)..(30)
<223> OTHER INFORMATION: Xaa is Gly or absent
<220> FEATURE:
<221> NAME/KEY: MISC_FEATURE
<222> LOCATION: (31)..(31)
<223> OTHER INFORMATION: Xaa is Pro or absent
<220> FEATURE:
<221> NAME/KEY: MISC_FEATURE
<222> LOCATION: (32)..(32)
<223> OTHER INFORMATION: Xaa is Glu, Ser or absent
<220> FEATURE:
<221> NAME/KEY: MISC_FEATURE
<222> LOCATION: (33)..(33)
<223> OTHER INFORMATION: Xaa is Ser, Lys or absent
<220> FEATURE:
<221> NAME/KEY: MISC_FEATURE
<222> LOCATION: (34)..(34)
<223> OTHER INFORMATION: Xaa is Gly or absent
<220> FEATURE:
<221> NAME/KEY: MISC_FEATURE
<222> LOCATION: (35)..(35)
<223> OTHER INFORMATION: Xaa is Ala or absent

```
<220> FEATURE:
<221> NAME/KEY: MISC_FEATURE
<222> LOCATION: (36)..(36)
<223> OTHER INFORMATION: Xaa is Pro or absent
<220> FEATURE:
<221> NAME/KEY: MISC_FEATURE
<222> LOCATION: (37)..(37)
<223> OTHER INFORMATION: Xaa is Pro or absent
<220> FEATURE:
<221> NAME/KEY: MISC_FEATURE
<222> LOCATION: (38)..(38)
<223> OTHER INFORMATION: Xaa is Pro or absent
<220> FEATURE:
<221> NAME/KEY: MISC_FEATURE
<222> LOCATION: (39)..(39)
<223> OTHER INFORMATION: Xaa is Ser or absent

<400> SEQUENCE: 47

Tyr Xaa Glu Gly Thr Xaa Thr Ser Asp Tyr Ser Xaa Xaa Leu Glu Xaa
1               5                   10                  15

Gln Ala Ala Xaa Xaa Phe Xaa Xaa Trp Leu Leu Xaa Gly Xaa Xaa Xaa
            20                  25                  30

Xaa Xaa Xaa Xaa Xaa Xaa Xaa
        35

<210> SEQ ID NO 48
<211> LENGTH: 29
<212> TYPE: PRT
<213> ORGANISM: Homo sapiens

<400> SEQUENCE: 48

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25
```